US006489454B1

(12) United States Patent
Liu et al.

(10) Patent No.: US 6,489,454 B1
(45) Date of Patent: Dec. 3, 2002

(54) ENGULFMENT GENE AND USES THEREOF

(75) Inventors: Qiong Liu, Hauppauge, NY (US); Michael O. Hengartner, Cold Spring Harbor, NY (US); Thierry Andre Oliver Eddy Bogaert, Kortrijk (BE); Wim Maria Rene Van Criekinge, Kontich (BE)

(73) Assignees: deVGen nv, Ghent-Zwijnaarde; Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 09/096,731

(22) Filed: Jun. 11, 1998

Related U.S. Application Data

(60) Provisional application No. 60/072,324, filed on Jan. 23, 1998.

(51) Int. Cl.[7] .............................................. C07H 21/02
(52) U.S. Cl. .................... 536/23.1; 536/23.1; 435/69.1; 435/6; 435/243; 435/183; 435/7.1; 435/7.2; 435/7.24; 435/7.8; 435/320.1; 530/350; 530/300
(58) Field of Search .......................... 435/69.1, 6, 243, 435/183, 7.1, 7.2, 7.24, 7.8, 320.1; 536/23.1; 530/350, 300

(56) References Cited

U.S. PATENT DOCUMENTS 5,837,478 A * 11/1998 Gallatin et al. ............. 435/7.24
5,897,992 A    4/1999 Fearnhead et al. ............ 435/29

FOREIGN PATENT DOCUMENTS

WO    WO 93 20237       10/1993
WO    WO 01/36458 A2    5/2001

OTHER PUBLICATIONS

Adams et al., Nature, vol. 377 (6547 Suppl.), pp. 3–178, Sep. 28, 1995.*
Abstract and Slides presented by Dr. Liu on June 1, 1997 at the 11th International *C. elegans* Meeting, Madison, Misconsin.
Abstract from 1996 East coast Meeting on Jun. 9–11, New Jersey.
Abstract from an AACR Special Conference on Programmed Cell Death, Oct. 19–23 (1996).
Hengartner, *Cell Death in C. elegans II, Plain View*, Cold Spring Harbour Laboratory Press, pp. 383–415 (1997).
Liu, et al., "Candidate adaptor protein CED–6 promotes the engulfment of apoptotic cells in *C–elegans*," *Cell*, 93(6):961–972 (1988).
Ellis, et al., "Genes Required for the Engulfment of Cell Corpses During Programmed Cell Death in *Caernorhabditis elegans*", *Genetics* 129:79–94 (1991).

Horvitz, et al., "The Genetics of Programmed Cell Death in the Nematode *Caenorhabditis elegans*", *Cold Spring Harbour Symp. Quant Biol.* 59:377–385 (1994).
Botto, M. et al., "Homozygous C1q deficiency causes glomerulonephritis associated with multiple apoptotic bodies", *Nature Genetics,* 19:56–59 (1998).
Blaikie, et al., "Region in She Distinct from the SH2 Domain Can Bind Tyrosine–phosphorylated Growth Factor Receptors", *J. Biol. Chem* 269:32031–32034 (1994).
Bork and Margolis,"A Phosphotyrosine Interaction Domain" *Cell* 80:693–694 (1995).
Kohara, Y., et al., "Expression Map of the C. Elegans Genome," *EMBL Sequence Data Library*, Accession No. C44233, (Sep. 8, 1997).
Duvall, et al., "Macrophage recognition of cells undergoing programmed cell death (apoptosis)", *Immunology* 56:351–358 (1985).
Duvall and Wyllie, "Death and the cell", *Immunol Today* 7:115–119 (1986).
Carroll, M., "The lupus paradox", *Nature Genetics,* 19:3–4 (1988).
Gout, et al., "The GTPase Dynamin Binds to and Is Activated by a Subset of SH3 Domains", *Cell* 75:25–36 (1993).
Greenberg, S., "Signal transduction of phagocytosis", *Trends in Cell Biol* 5:93–99 (1995).
Greenberg, et al., "Tyrosine Phosphorylation Is Required for Fc Receptor–mediated Phagocytosis in Mouse Macrophages", *J. Exp. Med.* 177:529–534 (1993).
Hedgecock, et al., "Mutations Affecting Programmed Cell Deaths in the Nematode *Caenorhabditis elegans*", *Science* 222:1277–1279 (1983).
Bianco, et al., "Studies of the Macrophage Complement Receptor", *J. Exp. Med.* 141:1278–1290 (1975).
Huang and Hirsh, "A second trans–splice RNA leader sequence in the nematode *Caenorhabditis elegans*", *Proc. Natl. Acad. Sci. USA* 88:8640–8644 (1989).
Kavanaugh and Williams, "An Alternative to SH2 Domains for Binding Tyrosine–Phosphorylated Proteins" *Science* 266 (1994).
Koch, et al., "SH2 and SH3 Domains: Elements That Control Interactions of Cytoplasmic Signaling Protiens", *Science* 252:252–673 (1991).
Pawson, et al., "SH2 and SH3 domains", *Current Biology*, 3:434–42 (1993).

(List continued on next page.)

*Primary Examiner*—Christopher S. F. Low
*Assistant Examiner*—Hope A. Robinson
(74) *Attorney, Agent, or Firm*—Hamilton, Brook, Smith & Reynolds, P.C.

(57) ABSTRACT

The invention relates to a signal transduction pathway which promotes phagocytosis of apoptotic cells and in particular relates to a protein known as CED-6 in the nematode worm *C. elegans*, human equivalents of CED-6 protein and nucleic acids encoding them. The invention also relates to use of the proteins and encoding nucleic acids in assay methods for detecting compounds which enhance or inhibit the signal transduction pathway and use of the proteins, nucleic acids and identified enhancer or inhibitor compounds in methods of treatment of human or animal disease.

15 Claims, 35 Drawing Sheets

OTHER PUBLICATIONS

Rosenshine and Finlay, "Exploitation of Host Signal Transduction Pathways and Cytoskeletal Functions by Invasive Bacteria", *BioEssays 15:*17–24 (1993).

Spieth, et al., "Operons in *C. elegans* : Polycistronic mRNA Precursors are Processed by Trans–Splicing of SL2 to Downstream Coding Regions", *Cell 73:*521–532 (1993).

Hillier, L., et al., "WashU–Merck EST project 1997," *EMBL Sequence Data Library,* Accession No. AA431753, (May 25, 1997).

Thompson, C.B., "Apoptosis in the Pathogenesis and Treatment of Disease", *Science,* 267:1456–1462 (1995).

Vaux, D.L., "CED–4–The Third Horseman of Apoptosis", *Cell,* 90:389–390 (1997).

Wilson, R., et al., "2.2 Mb of contiguous nucleotide sequence from chromosome III of *C. elegans"*, *Nature,* 368:32–38 (1994).

Wu, Y.C., et al., "*C. elegans* phagocytosis and cell–migration protein CED–5 is similar to human Dock 180", *Nature,* 392(2):501–504 (1998).

Wyllie, A.H., et al., "Cell Death: The Significance of Apoptosis", *International Review of Cytology,* 86:251–306.

Zhou, M.M., et al., "Structure and ligand recognition of the phosphotyrosine binding domain of Shc", *Nature,* 378:584–592 (1995).

Zorio, D.A.R., et al., Operons as a common form of chromosomal organization in *C. elegans, Nature,* 372:270–272 (1994).

Driscoll, M., "Cell Death in *C Elegans:* Molecular Insights into Mechanisms conserved between nematodes and mammals," Brain Pathology, 6:411–425 (1996).

Ramesh, N., et al., "WIP, a Protein Associated with Wiskott–Aldrich syndrome protein, induces actin polymerisation and redistribution in lympoid cells," Proc. Natl. Acad. Sci., 94:14671–14676 (Dec. 1997).

Nagase, T., et al., "Prediction of the Coding Sequences of Unidentified Human Genes. VI. The Coding Sequences of 80 New Genes (KIAA0201–KIAA0280) Deduced by Analysis of cDNA Clones from Cell Line KG–1 and Brain," DNA Research, 3:321–329 (Jan. 1, 1996).

\* cited by examiner

FIG. 2A

```
                        αααααααα      ββββββ ββ                         αααααααααααααααααααααα
CED-6        (49)       HPPDYLINGHVEYVARFLGCVETPKA-----NGSDVAREAIHAIRFQRDLKRSE---
C. briggsae EST (39)    HPPDFLINGHVEYGARFLGCVETAKE-----NGTAVAREAIHAIRFQRDLKRSE---
Human EST    (1)                                                     FARHIKKSE---
Human SHC    (40)       HPNDKVMGPGVSYLVRYMGCVEVLQSMRALDFNTRT-QVTREAISLVCEAVPGAKGATRR
Drosophila SHC (22)     YPDDVIMGVGVAFNVRYTGCVEVKTSMKSLDFETRT-QLARECINRVCEAAG-LKSAGKR
Drosophila Numb (71)    ADEEAVRSATCSFSVKYLGCVEVFES-----RGMQVCEEALKVLRQ------SRR
Mouse p96    (38)       YLLARFKGDGVKYKAKLIGLIDDVPDA-----RGDKMSQDSMMKLKGMAAAGRS
Drosophila Disabled (39) NDPGRFFGDGVQFKAKLIGILEVGEA-----RGDRMCQEALQDLKMAIRAA---
C. elegans M110.5 (98)  SDPFRFQNNGISYKGKLIGEQDVDKA-----RGDAMCAEAMRTAKSIIKAA---

βββ                          βββ βββββ                    ββ ββββ               βββββ
CED-6                   ---QTRETAKLQKVEVRISIDNVIIADIKTKAPMYTFP---LGRISFCAD
C. briggsae EST         ---QTRETAKLQKVEVRISIDYYVRVDDAKTMMYQFQ---LPRISFCAD
Human EST               ---EGQKIPKVELQISIYGVKILEPKTKEVQXQLPNCQLHRISFCAD
Drosophila EST (1)      RKPCSRPLSSILGRSNLKFAGMPHTLTVSTSLNLMAADCKQIIANHH---MQSISFASG
Human SHC               RLT----NFISDRPSMQHAGTNHIENVSSRALSLSNVETGEVIANHN---MPRISFASG
Drosophila Numb         RP-----VRGLLHVSGDGLRVVDDETFKLIVDQT---IEKVSFCAP
Mouse p96               ---QGQHKQRIWVNISLSGIKIIDEKTGVIEHEHP---VNKISFIAR
Drosophila Disabled     ---GEHKQRITHVTIDGLRLRDEKTGDSLYHHP---VHKISFIAQ
C. elegans M110.5       ---GAHKTRITLQENIDGIKVLDEKSGAVLHNFP---VSRISFIAR ββββ                                          αααααααααααααααααα
CED-6                   ---SCYAFTSEK---LAEDITLTIGEAFDLAYKRFLDKNR
Human EST               ---LCYVEDSEK---CAEEITLTIGQAFXLAYRKFLESGG
Drosophila EST          ---GVKKFESFIA--(31)---ECFVEISNK---LASDITLTIGQAFDLAYRKYMD
Human SHC               --GDPDTAEYVAVAKDPVNQR-ACHILECPEG---LAQDVISTIGQAFELRFKQYLRNPP
Drosophila SHC          --GDNDTLDFLAYIAKNEDEWR-ACYVLECAGG---QSEDLIVEIGKAFALRFNALSRLND
Drosophila Numb         --DRNHERGFSFAKCRDGTTRRWMCHGFLACKD---SGERLSHAVGCAFVCLERKQRRDK
Mouse p96               --DVTDNRAEGYVCGGE---GQHQFFAIKTGQQAEPLVVDLKDLFQVIYNVKKKEED
Drosophila Disabled     --DMTDSRAFGYIFGSPD---SGHRFFGIKTDKAASQVVLAMRDLEQVVFELKKKIE
C. elegans M110.5       --SSDARAFGLVYGEPG---GKYKFEYGIKTAQAADQAVLAIRDMFQVVFEMKKKQIE
```

FIG. 3A

Table: The genetic mosaic analysis of ced-6

| # animal | Progeny phenotype | sheath cells phenotype | | cell corpses in gonad | |
|---|---|---|---|---|---|
| | | anterior arm | posterior arm | anterior arm | posterior arm |
| 1 | DPY UNC | wt | wt | No | No |
| 2 | DPY UNC | wt | wt | No | No |
| 3 | DPY UNC | wt | wt | No | No |
| 4 | DPY UNC | wt | wt | No | No |
| 5 | DPY UNC | wt | wt | No | No |
| 6 | wt | Ncl | wt | Yes | No |
| 7 | wt | Ncl | wt | Yes | No |
| 8 | wt | Ncl | wt | Yes | No |
| 9 | wt | wt | Ncl | No | Yes |

| # Cell Corpses in Young L1 Larvae | Genotype | Heat Shock | Mean of Cell Corpses |
|---|---|---|---|
| | N2 | − | 0 |
| | ced-6(n1813) | − | 13 |
| | ced-6(n1813) | + | 10 |
| | ced-6(n1813);hs::ced-6 | − | 14 |
| | ced-6(n1813);hs::ced-6 | + | 3 |
| | ced-6(n1813);hs::lacZ | + | 11 |
| | ced-6(n1813);hs::ced-6 | + | .5 |
| | ced-6(n1813);hs::lacZ | + | 13 |

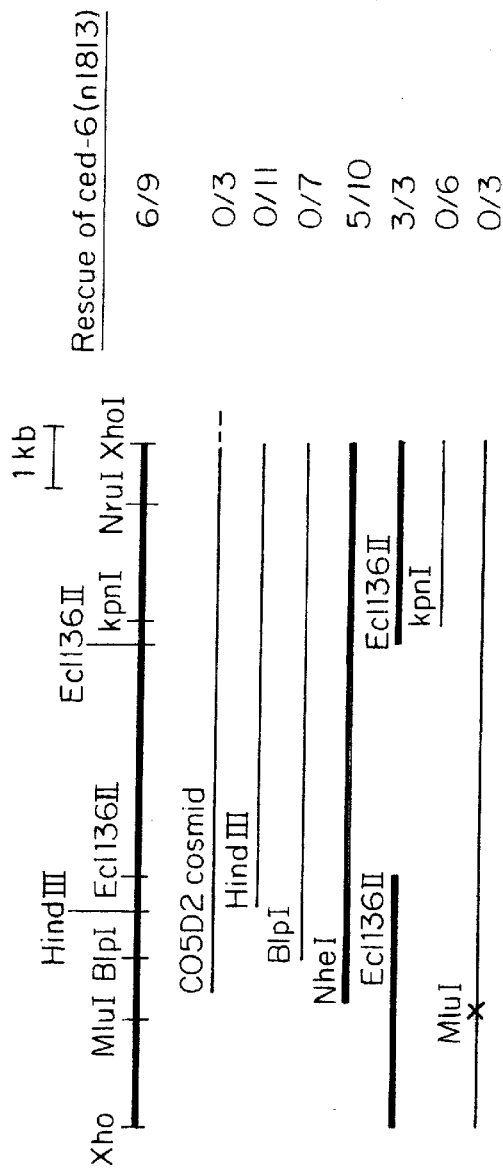
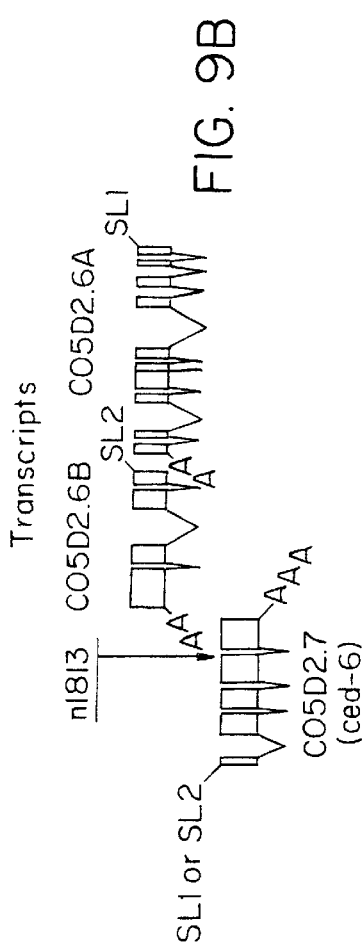
FIG. 9A
FIG. 9B

```
GGTGATGAGCCCTTGGGTTCTCGCTCCGACTGCTAAATTCGCTTGGCCGGGTCCACCTTCTCGT
GGCCTCACTCGCCACACGGATCAGAATCCGGAGCAGGCAGTTCTCTCTATTCTGAGGCTCCTG
CGGCTGCCGCGCTGACTTCCCTGTGTGGNGGAGGGAACTCTGGGCAGGCTGGTTTTCTTGGAA
TGTGTTTACGATGTTGAATGGGACTTGAACAGGAAGCTGGACGCTGCAGCTGGAACTAGCGTG
CCAAGTTATTTATGATTCCATCTGATATACATAGGAGAGAAACTGATAGAAGAATTCTGATGG
CAACTGTATGATAGAAGCTATATAAAGTCAAGTGTCCATTTTCTTTCAACTATATTTGAGCATA
CCCAGGATTTAAGTCGTGGAACTGAACATTTATTTGGCTGATCCTCATCATGAACCGTGCTTTT
AGCAGGAAGAAAGACAAAACATGGATGCATACACCTGAAGCTTTATCAAAACATTTCATTCC
CTATAATGCAAAGTTTCTTGGCAGTACAGAAGTGGAACAGCCAAAAGGAACAGAAGTTGTGA
GAGATGCTGTAAGGAAACTAAAGTTTGCAAGACATATCAAGAAATCTGAAGGCCAGAAAATT
CCTAAAGTGGAGTTGCAAATATCAATTTATGGAGTAAAAATTCTAGAACCCAAAACAAAGGA
AGTTCAACACAATTGCCAGCTTCATAGAATATCTTTTTGTGCAGATGATAAAACTGACAAGAG
GATATTCACTTTCATATGCAAAGATTCTGAGTCAAATAAACATTTGTGCTATGTATTTGACAGC
GAAAAGTGTGCTGAAGAGATCACTTTAACAATTGGCCAAGCATTTGACCTGGCATACAGGAA
ATTTCTAGAATCAGGAGGAAAAGATGTTGAAACAAGAAAACAGATCGCAGGGTTACAAAAAA
GAATCCAAGACTTAGAAACAGAAAATATGGAACTTAAAAATAAAGTACAAGATTTGGAAAAC
CAACTGAGAATAACTCAAGTATCAGCACCTCCAGCAGGCAGTATGACACCTAAGTCGCCCTCC
ACTGACATCTTTGATATGATTCCATTTTCTCCAATATCACACCAGTCTTCGATGCCTACTCGCA
ATGGCACACAGCCACCTCCAGTACCTAGTAGATCTACTGAGATTAAACGGGACCTGTTTGGAG
CAGAACCTTTTGACCCATTTAACTGTGGAGCAGCAGATTTCCCTCCAGATATTCAATCAAAAT
TAGATGAGATGCAGGAGGGGTTCAAAATGGGACTAACTCTTGAAGGCACAGTATTTGTCTCG
ACCCGTTAGACAGTAGGTGCTGACATCAAGAACAAGAAATCCTGATTCATGTTAAATGTGTTT
GTATACACATGTCATTTATTATTATTACTTTAAGATAGGTATTATTCATGTGTCAATGTTTTGA
ATATTTTAATATTTTGAAAATTTTCTCAGTTAAATTTCCTCACCTTCACTATTGATCTGTAATTT
TTATTTTAAAAACAGCTTACTGTAAAGTAGATCATACTTTTATGTTCCTTTCTGTTTCTACTGTA
GATGAATTTGTAATTGAAAGACATATTATACAAATACCTGCCTTGTGTCTGAGTTCTATTTAGT
TAGCATCTTGAAATTTGTATTCATTTTCCAGATGGCTAGTTTATTAATGATTTCCCAAAAGCCA
TACCTTAAAGATAACTTTTTAAATTCTGAAGAGACATGCCAATGTCAAACTAAACATGTTCTG
TTTTTAAACCAACAAACATGTTACTATTCATTGGACAGATATCATTTTATGTATAAATACTGTT
CACATCACTGGGAAAATGTAAACTTTAAACATAATGCCACAAGGTCACTAATTTCTAGCAGGT
AAAATTATAAGGATATAAATTCCAATAATAAACCAAATGTATTTAGAGTATTTATTAGTAAAT
GCAAGGTGATGTTAGTTATGATCAGTTATACTCTAAATATTTAATTTGTTTTATAAAGGTAGTG
AAAAAATGAAAATTTGCTATTTATTAAAAAACATTAAATTTCATTCCAAATGAGATAAGTGAT
ATTACTATAACATCTAAGCATCATCTGATTTGATATTCCCTAAAAAACATTTGGAATATATGCT
ATCTATAGATTCAGTATCTACTACCCATATTTACTTTACCAAATATATTTCTCCTCACTGCATA
AGGACTACTCTTCTCATATTTTCTTCTTTGATGAAGATATTTTTCACCAAAGTTTATTTTGTGAT
GCCCTCTTGGTTTTGATACTTTAAAAATCTGTGGCACCCGTTCTACATGAATTATCAATATTTGG
TAAATTCAATCTGTATTTGTTTTGTTAAAGTCAAAAATCTCATTTTCCAAAAAAAAAAAAAAA
AAACTCGAG
```

FIG. 18

```
GGTGATGAGCCCTTGGGTTCTCGCTCCGACTGCTAAATTCGCTTGGCCGGGTCCACCTTCTCGT
GGCCTCACTCGCCACACGGATCAGAATCCGGAGCAGGCAGTTCTCTCTATTCTGAGGCTCCTG
CGGCTGCCGCGCTGACTTCCCTGTGTGGNGGAGGGAACTCTGGGCAGGCTGGTTTTCTTGGAA
TGTGTTTACGATGTTGAATGGGACTTGAACAGGAAGCTGGACGCTGCAGCTGGAACTAGCGTG
CCAAGTTATTTATGATTCCATCTGATATACATAGGAGAGAAACTGATAGAAGAATTCTGATGG
CAACTGTATGATAGAAGCTATATAAAGTCAAGTGTCCATTTTCTTTCAACTATATTTGAGCATA
CCCAGGATTTAAGTCGTGGAACTGAACATTTATTTGGCTGATCCTCATCATGAACCGTGCTTTT
AGCAGGAAGAAAGACAAAACATGGATGCATACACCTGAAGCTTTATCAAAACATTTCATTCC
CTATAATGCAAAGTTTCTTGGCAGTACAGAAGTGGAACAGCCAAAAGGAACAGAAGTTGTGA
GAGATGCTGTAAGGAAACTAAAGTTTGCAAGACATATCAAGAAATCTGAAGGCCAGAAAATT
CCTAAAGTGGAGTTGCAAATATCAATTTATGGAGTAAAAATTCTAGAACCCAAAACAAAGGC
TGAAGAGATCACTTTAACAATTGGCCAAGCATTTGACCTGGCATACAGGAAATTTCTAGAATC
AGGAGGAAAAGATGTTGAAACAAGAAAACAGATCGCAGGGTTACAAAAAAGAATCCAAGAC
TTAGAAACAGAAAATATGGAACTTAAAAATAAAGTACAAGATTTGGAAAACCAACTGAGAAT
AACTCAAGTATCAGCACCTCCAGCAGGCAGTATGACACCTAAGTCGCCCTCCACTGACATCTT
TGATATGATTCCATTTTCTCCAATATCACACCAGTCTTCGATGCCTACTCGCAATGGCACACAG
CCACCTCCAGTACCTAGTAGATCTACTGAGATTAAACGGGACCTGTTTGGAGCAGAACCTTTT
GACCCATTTAACTGTGGAGCAGCAGATTTCCCTCCAGATATTCAATCAAAATTAGATGAGATG
CAGGAGGGGTTCAAAATGGGACTAACTCTTGAAGGCACAGTATTTTGTCTCGACCCGTTAGAC
AGTAGGTGCTGACATCAAGAACAAGAAATCCTGATTCATGTTAAATGTGTTTGTATACACATG
TCATTTATTATTATTACTTTAAGATAGGTATTATTCATGTGTCAATGTTTTGAATATTTTAATA
TTTTGAAAATTTTCTCAGTTAAATTTCCTCACCTTCACTATTGATCTGTAATTTTATTTTAAAA
ACAGCTTACTGTAAAGTAGATCATACTTTTATGTTCCTTTCTGTTTCTACTGTAGATGAATTTGT
AATTGAAAGACATATTATACAAATACCTGCCTTGTGTCTGAGTTCTATTTAGTTAGCATCTTGA
AATTTGTATTCATTTTCCAGATGGCTAGTTTATTAATGATTTCCCAAAAGCCATACCTTAAAGA
TAACTTTTTAAATTCTGAAGAGACATGCCAATGTCAAACTAAACATGTTCTGTTTTAAACCAA
CAAACATGTTACTATTCATTGGACAGATATCATTTTATGTATAAATACTGTTCACATCACTGGG
AAAATGTAAACTTTAAACATAATGCCACAAGGTCACTAATTTCTAGCAGGTAAAATTATAAGG
ATATAAATTCCAATAATAAACCAAATGTATTTAGAGTATTTATTAGTAAATGCAAGGTGATGT
TAGTTATGATCAGTTATACTCTAAATATTTAATTTGTTTTATAAAGGTAGTGAAAAAATGAAA
ATTTGCTATTTATTAAAAAACATTAAATTTCATTCCAAATGAGATAAGTGATATTACTATAACA
TCTAAGCATCATCTGATTTGATATTCCCTAAAAAACATTTGGAATATATGCTATCTATAGATTC
AGTATCTACTACCCATATTTACTTTACCAAATATATTTCTCCTCACTGCATAAGGACTACTCTT
CTCATATTTTCTTCTTTGATGAAGATATTTTTCACCAAAGTTTATTTTGTGATGCCCTCTTGGTT
TTGATACTTTAAAATCTGTGGCACCCGTTCTACATGAATTATCAATATTTGGTAAATTCAATCT
GTATTTGTTTTGTTAAAGTCAAAAATCTCATTTTCCAAAAAAAAAAAAAAAAAACTCGAG
```

FIG. 19

MNRAFSRKKDKTWMHTPEALSKHFIPYNAKFLGSTEVEQPKGTEVVRDAVRKLKFARHIKKS
EGQKIPKVELQISIYGVKILEPKTK<u>EVQHNCQLHRISF</u>C<u>ADDKTDKRIFTF</u>IC<u>KDSESNKHLCYV</u>
<u>FDSEK</u>CAEEITLTIGQAFDLAYRKFLESGGKDVETRKQIAGLQKRIQDLETENMELKNKVQDLE
NQLRITQVSAPPAGSMTPKSPSTDIFDMIPFSPISHQSSMPTRNGTQPPPVPSRSTEIKRDLFGAEP
FDPFNCGAADFPPDIQSKLDEMQEGFKMGLTLEGTVFCLDPLDSRC*

FIG. 20

MNRAFSRKKDKTWMHTPEALSKHFIPYNAKFLGSTEVEQPKGTEVVRDAVRKLKFARHIKKS
EGQKIPKVELQISIYGVKILEPKTKAEEITLTIGQAFDLAYRKFLESGGKDVETRKQIAGLQKRIQDL
ETENMELKNKVQDLENQLRITQVSAPPAGSMTPKSPSTDIFDMIPFSPISHQSSMPTRNGTQPPPVPS
RSTEIKRDLFGAEPFDPFNCGAADFPPDIQSKLDEMQEGFKMGLTLEGTVFCLDPLDSRC*

FIG. 21

```
GGTGATGAGC CCTTGGGTTC TCGCTCCGAC TGCTAAATTC GCTTGGCCGG GTCCACCTTC TCGTGGCCTC ACTCGCCACA CGGATCAGAA TCCGGAGCAG    100
GCAGTTCTCT CTATTCTGAG GCTCCTGCGG CTGCCGGCTG ACTTCCCTGT GTGCGGGAGG GAACTCTGGG CAGGCTGGTT TTCTTGGAAT GTGTTTACGA    200
TGTTGAATGG GACTTGAACA GGAAGCTGGA CGCTGCAGCT GGAACTAGCG TGCCAAGTTA TTTATGATTC CATCTGATAT ACATAGGAGA GAAACTGATA    300
GAAGAATTCT GATGGCAACT GTATGATAGA AGCTACTATA AAGTCAAGTG TCCATTTTCT TTCAACTATA TTTGAGCATA CCCAGGATTT AAGTCGTGGA    400
ACTGAACATT TATTTGGCTG ATCCTCATCA TGAACCGTGC TTTTAGCAGG AAGAAAGACA AAACATGGAT GCATACACCT GAAGCTTTAT CAAAACATTT    500
                                                                          M  N  R  A   F  S  K  K  K  D  K   T  W  M  H  T  P  E  A  L  S   K  H  F
CATTCCCTAT AATGCAAAGT TTCTTGGCAG TACAGAAGTG GAACAGCCAA AAGGAACAGA AGTTGTGAGA GATGCTGTAA GGAAACTAAA GTTTGCAAGA    600
 I  P  Y    N  A  K  F   L  G  S   T  E  V   E  Q  P  K    G  T  E   V  V  R   D  A  V   R  K  L  K   F  A  R
                                                                PTB domain
CATATCAAGA AATCTGAAGG CCAGAAAATT CCTAAAGTGG AGTGCAAAT ATCAATTTAT GGACTAAAAA TTCTAGAACC CAAAACAAAG GAAGTTCAAC    700
 H  I  K     K  S  E  G   Q  K  I    P  K  V   E  C  K    I  S  I  Y   G  V  K  I   L  E  P    K  T  K   E  V  Q  H
ACAAATTGCCA GCTTCATAGA ATATCTTTTT GTGCAGATGA TAAAACTGAC AAGAGGATAT TCACTTTCAT ATGCAAAGAT TCTGAGTCAA ATAAACATTT    800
 N  C  Q   L  H  R    I  S  F  C   R  D  D    K  K  D  K   P  I  F   T  F  I   C  K  D    S  F  S  N   K  H  L
GTGCTATGTA TTTGACAGCG AAAAGTGTGC TGAAGAGATA ACTTTAACAA TTGGCCAAGC ATTTGACCTG GCATACAGGA AATTCTAGA ATCAGGAGGA    900
 C  Y  V   F  D  S  F    K  C  A    E  E  I    T  L  T  I    L  G  Q   A  F  D  L   A  Y  R  K   F  L  E   S  G  G
AAAGATGTTG AAACAAGAAA ACAGATGCGA GGGTTACAAA AAAGAATCCA AGATTAGAA ACAGAAAATA TGGAACTTAA AAATAAAGTA CAAGATTTGG    1000
 K  D  V  E   T  R  K    Q  I  A   G  L  K    R  I  Q    D  L  E    T  E  N  M   L  L  K   N  K  V   Q  D  L  E
                       charged region
AAAACCAACT GAGAATAACT CAAGTATCAG CACCTGCAGC AGGCAGTATG ACACCTAAGT CGCCCTCCAC TGACATCTTT GATATGATTC CATTTTCTCC    1100
 N  Q  L   R  I  T   Q  V  S  A    P  E  A   G  S  M   T  P  K  S    P  S  T    D  I  F    D  M  I  P   F  S  P
AATATACAC CAGTCTTCGA TGCCTACTCG CAATGGCACA CAGCCACCTC CAGTACCTAG TACATCTACT GAGATTAAAC GGGACCTGTT TGGAGCAGAA    1200
 I  S  H   Q  S  S  M    P  T  R    E  C  T   Q  P  P   P  V  P  S    R  S  T   E  I  K  R   D  L  F   G  A  E
                                                                proline/serine rich region (potential SH3 binding domain)
CCTTTTGACC CATTTAACTG TGGAGCAGGA GATTCCCCTC CAGATATTCA ATCAAAATTA GATGAGATGC AGGAGGGGTT CAAAATGGGA CTAACTCTTG    1300
 P  F  D  P    F  N  C    G  A  A   D  F  P    P  D  I  S    S  K  L   D  E  M  Q   D  G  F   K  M  G   L  T  L  E
AAGGCACAGT ATTTTGTCTC GACCCGTTAG ACAGTAGGTG CTGACATCAA GAACAAGAAA TCCTGATTCA TGTTAAATGT GTTTCTATAC ACATGTCATT    1400
 G  T  V   F  C  L   D  P  L  D   S  R  C   *
TATTATTATT ACTTTAAGAT AGGTATTATT CATGTGTCAA TGTTTTGAA TATTTTAATA TTTGAAAAT TTTCTCAGTT AAATTCCCTC ACCTTCACTA    1500
TTGATCTGTA ATTTTTATTT TAAAAACAGC TTACTGTAAA GTAGATCATA CTTTTACGTT CCTTTCTGTT TCTACTGTAG ATGAATTTGT AATTGAAAGA    1600
CATATTATAC AAATACCTGC CTTGTGTCTG AGTTCTATTT AGTTAGCATC TTGAAATTTG TATTCATTTT CCAGATGGCT AGTTATTAA TGATTTCCCA    1700
AAAGCCATAC CTTAAAGATA ACTTTTTAAA TTCTGAAGAG ACATGCCAAT GTCAAACTAA ACATGTCCTG TTTTTAAACC AACAAACATG TTACTATTCA    1800
TTGGACAGAT ATCATTTTAT GTATAAATAC TGTTCACATC ACTGGGAAAA TGTAAACTTT AAACATAATG CCACAAGGTC ACTAATTTCT AGCAGGTAAA    1900
ATTATAAGGA TATAAATTCC AATAATAAAC CAAATGTATT TAGAGTATTA ATTAGTAAAT GCAAGGTGAT GTTAGTTATG ATCAGTTATA CTCTAAATAT    2000
TTAATTTGTT TTATAAGGT AGTGAAAAAA TGAAAATTTG CTATTTATTA AAAACATTA AATTTCATTC CAAATGAGAT AAGTGATATT ACTATAACAT    2100
CTAAGCATCA TCTGATTTGA TATTCCCTAA AAAACATTTG GAATATATGC TATCTATAGA TTCAGTATCT ACTACCCATA TTTACTTTAC CAAATATATT    2200
TCTCCTCACT GCATAAGGAC TACTCTTCTC ATATTTTCTT CTTTGATGAA GATATTTTTC ACCAAGTTT ATTTGTGAT GCCCTCTTGG TTTTGATACT    2300
TTAAAATCTG TGGCACCCGT TCTACATGAA TTATCAATAT TTGGTAAATT CAATCTGTAT TTGTTTGTT AAGTCAAAA ATCTCATTTT CCAAAAAAAA    2400
AAAAAAAAAA AC                                                                                                 2412
```

FIG. 22

```
Sequence 1: CED-6,    492 residues
Sequence 2: hCED6,    304 residues

List of local alignments with score >= 350

47 5% identity in 184 residues overlap; Score: 3860; Gap frequency: 27%

CED-6,   45  RTWIHPPDYLINGHVEYVARFLGCVETPKANGSDVAREAIHAIRFQRDLKRSEQTRETAK
hCED6,   11  KTWMHTPEALSKHFIPYNAKFLGSTEVEQPKGTEVVRDAVRKIKFARHIKKSE----GQK
              ** *  *  *  * * *** **  ** *   *    ***** ** *         *

CED-6,  105  LQKVEIRISIDNVIIADIKTKAPMYTFPLGRISFCADDKDDKRMFSFIARAEGASGKPSC
hCED6,   67  IPKVELQISIYGVKILEPKTKEVQHNCQLHRISFCADDKTDKRIFTFICK-DSESNKHLC
              *** * **  *   * *** *       ******* *** * * *  *  *    *

CED-6,  165  YAFTSEKLAEDITLTIGEAFDLAYKRFLDKNRTSLENQKQIYILKKKIVELETENQVLIE
hCED6,  126  YVFDSEKCAEEITLTIGQAFDLAYTKFLESGGKDVETRKQIAGLQKRIQDLETENMELKN
              * * *** ** ****** ******  ***      * ***  * ** ***** * *

CED-6,  225  RLAE
hCED6,  186  KVQD
              *

--------
31 6% identity in 38 residues overlap; Score: 380; Gap frequency: 00%

CED-6,  265  PNIPPSSIYSMPRANDLPPTEMAPTLPQISTSSNGASP
hCED6,  221  PFSPISHQSSMPTRNGTQPPVPSRSTEIKRDLFGAEP
              *  *    ***    * ** *       * * * *
```

FIG. 24

| length (kb) | Expression level | |
|---|---|---|
| 3,6 | + | heart |
| | | brain |
| 3,6 | +++ | placenta |
| 3,6 | + | lung |
| | | liver |
| 3,6 | ++ | skeletal muscle |
| 3,6 | + | kidney |
| 3,6 | + | pancreas |
| 3,6 | + | spleen |
| | | thymus |
| 3,6 | + | prostate |
| 3,9 | ++ | testis |
| 3,6 | + | ovary |
| 3,6 | + | small intestine |
| 3,6 | + | colon (mucosal lining) |
| | | peripheral blood leukocyte |
| | | promyelocytic leukemia HL-60 |
| 3,6 | ++ | HeLa cell S3 |
| 3,6 | +++ | chronic myelogenous leukemia K562 |
| | | lymphoblastic leukemia MOLT-4 |
| | | Burkitt's lymphoma Raji |
| 3,6 | +++ | colorectal adenocarcinoma SW480 |
| 3,6 | +++ | lung carcinoma A549 |
| 3,6 | + | melanoma G361 |

FIG. 25

Untitled-1 Formatted Alignment

```
The PCR fragment      ---------- ---------- ---------- ---------- ----------
hbc3123 EST clone.    ---------- ---------- ---------- ---------- ----------
hced-6 cDNA           GGTGATGAGC CCTTGGGTTC TCGCTCCGAC TGCTAAATTC GCTTGGCCGG   50
5'/R65882/genbank     ---------- ---------- ---------- -GCTAAATTC GCTTGGCCGG   19
5'/AA159394/genbank copy  GGTGATGAGC CCTTGGGTTC TCGCTCCGAC TGCTAAATTC GCTTGGCCGG   50
R65983 complement/genbank ---------- ---------- ---------- ---------- ----------
Consensus             GGTGATGAGC CCTTGGGTTC TCGCTCCGAC TGCTAAATTC GCTTGGCCGG   50

The PCR fragment      ---------- ---------- ---------- ---------- ----------
hbc3123 EST clone.    ---------- ---------- ---------- ---------- ----------
hced-6 cDNA           GTCCACCTTC TCGTGGCCTC ACTCGCCACA CGGATCAGAA TCCGGAGCAG  100
5'/R65882/genbank     GTCCACCTTC TCGTGGCCTC ACTCGCCACA CGGATCAGAA TCCGGAGCAG   69
5'/AA159394/genbank copy  GTCCACCTTC TCGTGGCCTC ACTCGCCACA CGGATCAGAA TCCGGAGCAG  100
R65983 complement/genbank ---------- ---------- ---------- ---------- ----------
Consensus             GTCCACCTTC TCGTGGCCTC ACTCGCCACA CGGATCAGAA TCCGGAGCAG  100

The PCR fragment      ---------- ---------- ---------- ---------- ----------
hbc3123 EST clone.    ---------- ---------- ---------- ---------- ----------
hced-6 cDNA           GCAGTTCTCT CTATTCTGAG GCTCCTGCGG C-TGCCGGC- TGACTTCCC-  147
5'/R65882/genbank     GCAGTTCTCT CTATTCTGAG GCTCCTGCGG C-TGCCGGC- TGACTTCCC-  116
5'/AA159394/genbank copy  GCAGTTCTCT CTATTCTGAG GCTCCTGCGG CNTGCCNGCG TGACTTCCCG  150
R65983 complement/genbank ---------- ---------- ---------- ---------- ----------
Consensus             GCAGTTCTCT CTATTCTGAG GCTCCTGCGG CNTGCCNGCG TGACTTCCCG  150

The PCR fragment      ---------- ---------- ---------- ---------- ----------
hbc3123 EST clone.    ---------- ---------- ---------- ---------- ----------
hced-6 cDNA           TGTGTGCGGG AGGGAACTCT GGGCAGGCTG GTTTTCTTGG AATGTGTTTA  197
5'/R65882/genbank     TGTGTGCGGG AGGGAACTCT GGGCAGGCTG GTTTTCTTGG AATGTGTTTA  166
5'/AA159394/genbank copy  TGTGTGGNGG AGGGAACTCT GGGCAGGCTG GTTTTCTTGG AATGTGTTTA  200
R65983 complement/genbank ---------- ---------- ---------- ---------- ----------
Consensus             TGTGTGSNGG AGGGAACTCT GGGCAGGCTG GTTTTCTTGG AATGTGTTTA  200

The PCR fragment      ---------- ---------- ---------- ---------- ----------
hbc3123 EST clone.    ---------- ---------- ---------- ---------- ----------
hced-6 cDNA           CGATGTTGAA TGGGACTTGA ACAGGAAGCT GGACGCTGCA GCTGGAACTA  247
5'/R65882/genbank     CGATGTTGAA TGGGACTTGA ACAGGAAGCT GGACGCTGCA GCTGGAACTA  216
5'/AA159394/genbank copy  CGATGTTGAA TGGGACTTGA ACAGGAAGCT GGACGCTGCA GCTGGAACTA  250
R65983 complement/genbank ---------- --CTTGAAAC GGGNAACCGG GCCNCTGCAA GCNGGAACTA   38
Consensus             CGATGTTGAA TGSKWSWWRM RSRNRAMSSK GSMNSYKSMA GCNGGAACTA  250

The PCR fragment      ---------- ---------- ---------- ---------- ----------
hbc3123 EST clone.    ---------- ---------- ---------- ---------- ----------
hced-6 cDNA           GCGTG-CCAA GTTATTTATG A-TTCCATCT GATATACATA GGAGAGAAAC  295
5'/R65882/genbank     GCGTG-CCAA GTTATTTATG A-TTCCATCT GATATACATA GGAGAGAAAC  264
5'/AA159394/genbank copy  GCGTG-CCAA GTTATTTATG A-TTCCATCT GNTATACATA GGAGAGAAAC  298
R65983 complement/genbank CCGTGCCCAA GTTATTTATG ANCCCCACCT GATATACATG GGAGAGAAAC   88
Consensus             SCGTGCCCAA GTTATTTATG ANYYCCAYCT GNTATACATR GGAGAGAAAC  300

The PCR fragment      ------AAGA ATTTCTGATG GCAACTGTAT GATAGAAGCT A-TATAAAGT   43
hbc3123 EST clone.    ---------- ---------- ---------- ---------- ----------
hced-6 cDNA           T-GATAGAAG AATTCTGATG GCAACTGTAT GATAGAAGCT ATTATAAAGT  344
5'/R65882/genbank     T-GATAGAAG AATTCTGATG GCAACTGTAT GATAGAAGCT AT-ATAAAGT  312
5'/AA159394/genbank copy  TTGATAGAAG AATTCTGATG GCAACTGTAT GATAGAAGCT A-TATAAAGT  347
R65983 complement/genbank -TGATAGAAG AATTCTGATG GCAACTGTAT GATAGAAGCT A-TATAAAGT  136
Consensus             TTGATARARR AWTTCTGATG GCAACTGTAT GATAGAAGCT ATTATAAAGT  350

The PCR fragment      CAAGTGTCCA TTTTCTTTCA ACTATATTTG AGCATACCCA GGATTTAAGT   93
hbc3123 EST clone.    ---------- ---------- ---------- ---------- ----------
hced-6 cDNA           CAAGTGTCCA TTTTCTTTCA ACTATATTTG AGCATACCCA GGATTTAAGT  394
5'/R65882/genbank     CAAGTGTCCA TTTTCTTTCA ACTATATTTG AGCATACCCA GGGTTTAAGT  362
5'/AA159394/genbank copy  CAAGTGTCCA TTTTCTTTCA ACTATATTTG AGCATACCCA GGATTTAAGT  397
R65983 complement/genbank CAAGTGTCCA TTTTCTTTCA ACTATATTTG AGCATACCCA GGATTAAAGT  186
Consensus             CAAGTGTCCA TTTTCTTTCA ACTATATTTG AGCATACCCA GGRTTAAGT   400

The PCR fragment      CGTGGAACTG AACATTTATT TGGCTGATCC CTCATTCATG AACCGTGCTT  143
hbc3123 EST clone.    ---------- ---------- ---------- ---------- ----------
hced-6 cDNA           CGTGGAACTG AACATTTATT TGGCTGATCC -TCATCATG- AACCGTGCTT  442
5'/R65882/genbank     CGTGGAACTG AACATTTATT TGGCTGATCC -TCATCATGG AACCGTGCTT  411
5'/AA159394/genbank copy  CGTGGAACTG AACATT---- ---------- ---------- ----------  413
R65983 complement/genbank CGTGGAACTG AACATTTATT TGGCTGATCC -TCATCAT-G AACCGTGCTT  234
Consensus             CGTGGAACTG AACATTTATT TGGCTGATCC CTCATYMWKG AACCGTGCTT  450
```

FIG. 28A hced-6 alignment Formatted Alignment

```
//R65983/genbank.      TTTTAGCAGG AAGAAAGACA AAACATGGAT GCATACACCT GAAGCTTTAT  282
//hced-6 cDNA          TTTTAGCAGG AAGAAAGACA AAACATGGAT GCATACACCT GAAGCTTTAT  490
//The PCR fragment     TTTTAGCAGG AAGAAAGACA AAACATGGAT GCATACACCT GAAGCTTTAT  199
  hbc3123 EST clone    ---------- ---------- ---------- ---------- ----------
//5'/R65882/genbank    TTTTAGCAGG AAGAAAGACA AAACATGGGT GCTNACACCT GAAG-NTTAT  458
  5'/AA159394/genbank  ---------- ---------- ---------- ---------- ----------  415
  Consensus            TTTTAGCAGG AAGAAAGACA AAACATGGRT GCWNACACCT GAAGCNTTAT  500

//R65983/genbank.      CAAAACATTT CATTCCCTAT AATGCAAAGT TTCTTGGCAG TACAGAAGTG  332
//hced-6 cDNA          CAAAACATTT CATTCCCTAT AATGCAAAGT TTCTTGGCAG TACAGAAGTG  540
//The PCR fragment     CAAAACATTT CATTCCCTAT AATGCAAAGT TTCTTGGCAG TACAGAAGTG  239
  hbc3123 EST clone    ---------- ---------- ---------- ---------- ----------
//5'/R65882/genbank    CAAAACNTT- C-TTTCC--- NAT------- ---TT----- ----------  478
  5'/AA159394/genbank  ---------- ---------- ---------- ---------- ----------  415
  Consensus            CAAAACNTTT CATTYCCTAT NATGCAAAGT TTCTTGGCAG TACAGAAGTG  550

//R65983/genbank.      GAACAGCCAA AAGGAACAGA AGTTGTGAGA GATGCTGTAA GGAAACTAAA  362
//hced-6 cDNA          GAACAGCCAA AAGGAACAGA AGTTGTGAGA GATGCTGTAA GGAAACTAAA  590
//The PCR fragment     GAACAGCCAA AAGGAACAGA AGTTGTGAGA GATGCTGTAA GGAAACTAAA  289
  hbc3123 EST clone    ---------- ---------- ---------- ---------- ----------
  5'/R65882/genbank    ---------- ---------- ---------- ---------- ----------  478
  5'/AA159394/genbank  ---------- ---------- ---------- ---------- ----------  415
  Consensus            GAACAGCCAA AAGGAACAGA AGTTGTGAGA GATGCTGTAA GGAAACTAAA  600

//R65983/genbank.      GTTTGCAAGA CATNTCAAGA AATCTGAAGG CCAAAAAA-- ----------  420
//hced-6 cDNA          GTTTGCAAGA CATATCAAGA AATCTGAAGG CCAGAAAATT CCTAAAGTGG  640
//The PCR fragment     GTTTGCAAGA CATATCAAGA AATCTGAAGG CCAGAAAATT CCTAAAGTGG  339
  hbc3123 EST clone    ---------- ---------- ---------- ---------- ----------
  5'/R65882/genbank    ---------- ---------- ---------- ---------- ----------  478
  5'/AA159394/genbank  ---------- ---------- ---------- ---------- ----------  415
  Consensus            GTTTGCAAGA CATNTCAAGA AATCTGAAGG CCARAAAATT CCTAAAGTGG  650

R65983/genbank.      ---------- ---AA----- -----AAAAA ----AG---- ----------  429
//hced-6 cDNA          AGTTGCAAAT ATCAATTTAT GGAGTAAAAA TTCTAGAACC CAAAACAAAG  690
//The PCR fragment     AGTTGCAAAT ATCAATTTAT GGAGTAAAAA TTCTAGAACC CAAAACAAAG  389
  hbc3123 EST clone    ---------- ---------- ---------- ---------- ----------
  5'/R65882/genbank    ---------- ---------- ---------- ---------- ----------  478
  5'/AA159394/genbank  ---------- ---------- ---------- ---------- ----------  415
  Consensus            AGTTGCAAAT ATCAATTTAT GGAGTAAAAA TTCTAGAACC CAAAACAAAG  700

R65983/genbank.      ---------- ---------- ---------- ---------- ----------  429
//hced-6 cDNA          GAAGTTCAAC ACAATTGCCA GCTTCATAGA ATATCTTTTT GTGCAGATGA  740
//The PCR fragment     GAAGTTCAAC ACAATTGCCA GCTTCATAGA ATATCTTTTT GTGCAGATGA  439
//hbc3123 EST clone    ---------- //CAATTGCCA GCTTCATAGA ATATCTTTTT GTGCAGATGA   39
  5'/R65882/genbank    ---------- ---------- ---------- ---------- ----------  478
  5'/AA159394/genbank  ---------- ---------- ---------- ---------- ----------  415
  Consensus            GAAGTTCAAC ACAATTGCCA GCTTCATAGA ATATCTTTTT GTGCAGATGA  750

R65983/genbank.      ---------- ---------- ---------- ---------- ----------  429
//hced-6 cDNA          TAAAACTGAC AAGAGGATAT TCACTTTCAT ATGCAAAGAT TCTGAGTCAA  790
//The PCR fragment     TAAAACTGAC AAGAGGATAT TCACTTTCAT ATGCAAAGAT TCTGAGTCAA  489
//hbc3123 EST clone    TAAAACTGAC AAGAGGATAT TCACTTTCAT ATGCAAAGAT TCTGAGTCAA   89
  5'/R65882/genbank    ---------- ---------- ---------- ---------- ----------  478
  5'/AA159394/genbank  ---------- ---------- ---------- ---------- ----------  415
  Consensus            TAAAACTGAC AAGAGGATAT TCACTTTCAT ATGCAAAGAT TCTGAGTCAA  800

R65983/genbank.      ---------- ---------- ---------- ---------- ----------  429
//hced-6 cDNA          ATAAACATTT GTGCTATGTA TTTGACAGCG AAAAGTGTGC TGAAGAGATC  840
//The PCR fragment     ATAAACATTT GTGCTATGTA TTTGACAGCG AAAAGTGTGC TGAAGAGATC  539
//hbc3123 EST clone    ATAAACATTT GTGCTATGTA TTTGACAGCG AAAAGTGTGC TGAAGAGATC  139
  5'/R65882/genbank    ---------- ---------- ---------- ---------- ----------  478
  5'/AA159394/genbank  ---------- ---------- ---------- ---------- ----------  415
  Consensus            ATAAACATTT GTGCTATGTA TTTGACAGCG AAAAGTGTGC TGAAGAGATC  850

R65983/genbank.      ---------- ---------- ---------- ---------- ----------  429
//hced-6 cDNA          ACTTTAACAA TTGGCCAAGC ATTTGACCTG GCATACAGGA AATTTCTAGA  890
//The PCR fragment     ACTTTAACAA TTGGCCAAGC ATTTGACCTG GCATACAGGA AATTTCTAGA  589
//hbc3123 EST clone    ACTTTAACAA TTGGCCAAGC ATTTGACCTG GCATACAGGA AATTTCTAGA  189
  5'/R65882/genbank    ---------- ---------- ---------- ---------- ----------  478
  5'/AA159394/genbank  ---------- ---------- ---------- ---------- ----------  415
  Consensus            ACTTTAACAA TTGGCCAAGC ATTTGACCTG GCATACACGA AATTCTAGA   900
```

FIG. 28B

Untitled-1 Formatted Alignment

```
The PCR fragment           ---------- ---------- ---------- ---------- ----------    583
hbc3123 EST clone.         GAATCAGGAG GAAAAGATGT TGAAACAAGA AAACAGATCG CAGGGTTACA     237
hced-6 cDNA                GAATCAGGAG GAAAAGATGT TGAAACAAGA AAACAGATCG CAGGGTTACA     938
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  GAATCAGGAG GAAAAGATGT TGAAACAAGA AAACAGATCG CAGGGTTACA     950

The PCR fragment           ---------- ---------- ---------- ---------- ----------    583
hbc3123 EST clone.         AAAAAGAATC CAAGACTTAG AAACAGAAAA TATGGAACTT AAAAATAAAG     287
hced-6 cDNA                AAAAAGAATC CAAGACTTAG AAACAGAAAA TATGGAACTT AAAAATAAAG     988
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  AAAAAGAATC CAAGACTTAG AAACAGAAAA TATGGAACTT AAAAATAAAG    1000

The PCR fragment           ---------- ---------- ---------- ---------- ----------    583
hbc3123 EST clone.         TACAAGATTT GGAAAACCAA CTGAGAATAA CTCAAGTATC AGCACCTCCA     337
hced-6 cDNA                TACAAGATTT GGAAAACCAA CTGAGAATAA CTCAAGTATC AGCACCTCCA    1038
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  TACAAGATTT GGAAAACCAA CTGAGAATAA CTCAAGTATC AGCACCTCCA    1050

The PCR fragment           ---------- ---------- ---------- ---------- ----------    583
hbc3123 EST clone.         GCAGGCAGTA TGACACCTAA GTCGCCCTCC ACTGACATCT TTGATATGAT     387
hced-6 cDNA                GCAGGCAGTA TGACACCTAA GTCGCCCTCC ACTGACATCT TTGATATGAT    1088
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  GCAGGCAGTA TGACACCTAA GTCGCCCTCC ACTGACATCT TTGATATGAT    1100

The PCR fragment           ---------- ---------- ---------- ---------- ----------    583
hbc3123 EST clone.         TCCATTTTCT CCAATATCAC ACCAGTCTTC GATGCCTACT CGCAATGGCA     437
hced-6 cDNA                TCCATTTTCT CCAATATCAC ACCAGTCTTC GATGCCTACT CGCAATGGCA    1138
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  TCCATTTTCT CCAATATCAC ACCAGTCTTC GATGCCTACT CGCAATGGCA    1150

The PCR fragment           ---------- ---------- ---------- ---------- ----------    583
hbc3123 EST clone.         CACAGCCACC TCCAGTACCT AGTAGATCTA CTGAGATTAA ACGGGACCTG     487
hced-6 cDNA                CACAGCCACC TCCAGTACCT AGTAGATCTA CTGAGATTAA ACGGGACCTG    1188
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  CACAGCCACC TCCAGTACCT AGTAGATCTA CTGAGATTAA ACGGGACCTG    1200

The PCR fragment           ---------- ---------- ---------- ---------- ---------C    584
hbc3123 EST clone.         TTTGGAGCAG AACCTTTTGA CCCATTTAAC TGTGGAGCAG CAGATTTCCC     537
hced-6 cDNA                TTTGGAGCAG AACCTTTTGA CCCATTTAAC TGTGGAGCAG CAGATTTCCC    1238
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  TTTGGAGCAG AACCTTTTGA CCCATTTAAC TGTGGAGCAG CAGATTTCCC    1250

The PCR fragment           T--------- ---------- -------AGAT NCAGGAGG-- ----------    597
hbc3123 EST clone.         TCCAGATATT CAATCAAAAT TAGATGAGAT GCAGGAGGGG TTCAAAATGG     587
hced-6 cDNA                TCCAGATATT CAATCAAAAT TAGATGAGAT GCAGGAGGGG TTCAAAATGG    1288
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  TCCAGATATT CAATCAAAAT TAGATGAGAT NCAGGAGGGG TTCAAAATGG    1300

The PCR fragment           ---------- ---------- ---------- ---------- ----------    597
hbc3123 EST clone.         GACTAACTCT TGAAGGCACA GTATTTTGTC TCGACCCGTT AGACAGTAGG     637
hced-6 cDNA                GACTAACTCT TGAAGGCACA GTATTTTGTC TCGACCCGTT AGACAGTAGG    1338
5'/R65882/genbank          ---------- ---------- ---------- ---------- ----------    478
5'/AA159394/genbank copy   ---------- ---------- ---------- ---------- ----------    413
R65983 complement/genbank  ---------- ---------- ---------- ---------- ----------    401
Consensus                  GACTAACTCT TGAAGGCACA GTATTTTGTC TCGACCCGTT AGACAGTAGG    1350
```

Untitled-1 Formatted Alignment

```
The PCR fragment        ---------- ---------- ---------- ---------- ----------   597
hbc3123 EST clone.      TGTTACTATT CATTGGACAG ATATCATTTT ATGTATAAAT ACTGTTCACA  1137
hced-6 cDNA             TGTTACTATT CATTGGACAG ATATCATTTT ATGTATAAAT ACTGTTCACA  1838
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TGTTACTATT CATTGGACAG ATATCATTTT ATGTATAAAT ACTGTTCACA  1850

The PCR fragment        ---------- ---------- ---------- ---------- ----------   597
hbc3123 EST clone.      TCACTGGGAA AATGTAAACT TTAAACATAA TGCCACAAGG TCACTAATTT  1187
hced-6 cDNA             TCACTGGGAA AATGTAAACT TTAAACATAA TGCCACAAGG TCACTAATTT  1888
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TCACTGGGAA AATGTAAACT TTAAACATAA TGCCACAAGG TCACTAATTT  1900

The PCR fragment        ---------- ---------- ---------- ---------- ----------   597
hbc3123 EST clone.      CTAGCAGGTA AAATTATAAG GATATAAATT CCAATAATAA ACCAAATGTA  1237
hced-6 cDNA             CTAGCAGGTA AAATTATAAG GATATAAATT CCAATAATAA ACCAAATGTA  1938
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               CTAGCAGGTA AAATTATAAG GATATAAATT CCAATAATAA ACCAAATGTA  1950

The PCR fragment        ---------- ---------- ---------- ---------- ----------   597
hbc3123 EST clone.      TTTAGAGTAT TTATTAGTAA ATGCAAGGTG ATGTTAGTTA TGATCAGTTA  1287
hced-6 cDNA             TTTAGAGTAT TTATTAGTAA ATGCAAGGTG ATGTTAGTTA TGATCAGTTA  1988
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TTTAGAGTAT TTATTAGTAA ATGCAAGGTG ATGTTAGTTA TGATCAGTTA  2000

The PCR fragment        ---------- ---------- ---------- ---------- ----------   597
hbc3123 EST clone.      TACTCTAAAT ATTTAATTTG TTTTATAAAG GTAGTGAAAA AATGAAAATT  1337
hced-6 cDNA             TACTCTAAAT ATTTAATTTG TTTTATAAAG GTAGTGAAAA AATGAAAATT  2038
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TACTCTAAAT ATTTAATTTG TTTTATAAAG GTAGTGAAAA AATGAAAATT  2050

The PCR fragment        ---------- ---------- ---------- ---------- ----------   597
hbc3123 EST clone.      TGCTATTTAT TAAAAAACAT TAAATTTCAT TCCAAATGAG ATAAGTGATA  1387
hced-6 cDNA             TGCTATTTAT TAAAAAACAT TAAATTTCAT TCCAAATGAG ATAAGTGATA  2088
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TGCTATTTAT TAAAAAACAT TAAATTTCAT TCCAAATGAG ATAAGTGATA  2100

The PCR fragment        ---------- ---------- ---------- ---------- ----------   597
hbc3123 EST clone.      TTACTATAAC ATCTAAGCAT CATCTGATTT GATATTCCCT AAAAAACATT  1437
hced-6 cDNA             TTACTATAAC ATCTAAGCAT CATCTGATTT GATATTCCCT AAAAAACATT  2138
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TTACTATAAC ATCTAAGCAT CATCTGATTT GATATTCCCT AAAAAACATT  2150

The PCR fragment        ---------- ---------- ---------- ---------- ----------   597
hbc3123 EST clone.      TGGAATATAT GCTATCTATA GATTCAGTAT CTACTACCCA TATTTACTTT  1487
hced-6 cDNA             TGGAATATAT GCTATCTATA GATTCAGTAT CTACTACCCA TATTTACTTT  2188
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               TGGAATATAT GCTATCTATA GATTCAGTAT CTACTACCCA TATTTACTTT  2200

The PCR fragment        ---------- ---------- ---------- ---------- ----------   597
hbc3123 EST clone.      ACCAAATATA TTTCTCCTCA CTGCATAAGG ACTACTCTTC TCATATTTTC  1537
hced-6 cDNA             ACCAAATATA TTTCTCCTCA CTGCATAAGG ACTACTCTTC TCATATTTTC  2238
5'/R65882/genbank       ---------- ---------- ---------- ---------- ----------   478
5'/AA159394/genbank copy ---------- ---------- ---------- ---------- ----------  413
R65983 complement/genbank ---------- ---------- ---------- ---------- ----------  401
Consensus               ACCAAATATA TTTCTCCTCA CTGCATAAGG ACTACTCTTC TCATATTTTC  2250
```

FIG. 28E

Untitled-1 Formatted Alignment

```
The PCR fragment      ---------- ---------- ---------- ---------- ----------   597
hbc3123 EST clone.    TTCTTTGATG AAGATATTTT TCACCAAAGT TTATTTTGTG ATGCCCTCTT  1587
hced-6 cDNA           TTCTTTGATG AAGATATTTT TCACCAAAGT TTATTTTGTG ATGCCCTCTT  2288
5'/R65882/genbank     ---------- ---------- ---------- ---------- ----------   478
5'/AA159394/genbank copy  ---------- ---------- ---------- ---------- ----------   413
R65983 complement/genbank ---------- ---------- ---------- ---------- ----------   401
Consensus             TTCTTTGATG AAGATATTTT TCACCAAAGT TTATTTTGTG ATGCCCTCTT  2300

The PCR fragment      ---------- ---------- ---------- ---------- ----------   597
hbc3123 EST clone.    GGTTTTGATA CTTTAAAATC TGTGGCACCC GTTCTACATG AATTATCAAT  1637
hced-6 cDNA           GGTTTTGATA CTTTAAAATC TGTGGCACCC GTTCTACATG AATTATCAAT  2338
5'/R65882/genbank     ---------- ---------- ---------- ---------- ----------   478
5'/AA159394/genbank copy  ---------- ---------- ---------- ---------- ----------   413
R65983 complement/genbank ---------- ---------- ---------- ---------- ----------   401
Consensus             GGTTTTGATA CTTTAAAATC TGTGGCACCC GTTCTACATG AATTATCAAT  2350

The PCR fragment      ---------- ---------- ---------- ---------- ----------   597
hbc3123 EST clone.    ATTTGGTAAA TTCAATCTGT ATTTGTTTTG TTAAAGTCAA AAATCTCATT  1687
hced-6 cDNA           ATTTGGTAAA TTCAATCTGT ATTTGTTTTG TTAAAGTCAA AAATCTCATT  2388
5'/R65882/genbank     ---------- ---------- ---------- ---------- ----------   478
5'/AA159394/genbank copy  ---------- ---------- ---------- ---------- ----------   413
R65983 complement/genbank ---------- ---------- ---------- ---------- ----------   401
Consensus             ATTTGGTAAA TTCAATCTGT ATTTGTTTTG TTAAAGTCAA AAATCTCATT  2400

The PCR fragment      ---------- ---------- ----                              597
hbc3123 EST clone.    TTCCAAAAAA AAAAAAAAAA AAA-                             1710
hced-6 cDNA           TTCCAAAAAA AAAAAAAAAA AAAC                             2412
5'/R65882/genbank     ---------- ---------- ----                              478
5'/AA159394/genbank copy  ---------- ---------- ----                              413
R65983 complement/genbank ---------- ---------- ----                              401
Consensus             TTCCAAAAAA AAAAAAAAAA AAAC                             2424
```

FIG. 28F

ENGULFMENT GENE AND USES THEREOF

RELATED APPLICATION

This application claims the benefit of U.S. Provisional Application No. 60/072,324, entitled Adaptor Molecule CED-6 is Required for Engulfment of Apoptotic Cells, by *C. Elegans*, by Qiong Liu and Michael O. Hengartner (filed Jan. 23, 1998). The teachings of the referenced Provisional Application are incorporated herein in their entirety by reference.

GOVERNMENT SUPPORT

The invention was supported, in whole or in part, by Grant GM52540 from the National Institutes of Health. The Government has certain rights in the invention.

BACKGROUND TO THE INVENTION

Phagocytosis or engulfment, is a specialized form of endorytozis through which eukaryotes take up very lag particles, or even whole Cells. It is a fundamental biological process conserved from single-cell organisms, such as amoebae to mammals (Metchnikoff, E. 1891), Lectures on the comparative pathology of inflammation; delivered at the Pasteur Institute, 1891, 1968 Edition (New York: Dover Publication)), Initially used for the dual purpose of feeding and defense, phagocytosis evolved, following the emergence of mesoderm, into a mechanism used to protect the host against invading organisms and to clear up foreign particles and cell debris (Metchnikoff, 1891). Recently, the significance of phagocytosis has been extended due to its role in eliminating cells undergoing programmed cell death (apoptosis), Since apoptosis has been implicated in a number of human diseases elucidation of the regulation of this phagocytosis is highly desirable since it may lead to a new route of therapeutic intervention in these diseases.

SUMMARY OF THE INVENTION

Genetic studies in *C. elegans* have identified over a dozen genes that function in programmed cell death. The present inventors have used the positional method to clone and have functionally characterized the *C. elegans* gene ced-6. It is shown that the CED-6 protein contains a phosphotyrosine binding domain and several potential SH3 binding sites. It is further demonstrated that CED-6 acts within engulfing cells, and functions to promote the removal of both early and persistent cell corpses. Overexpression of ced-6 can partially suppress the engulfment defect of both ced-1 and ced-7, suggesting that ced-6 might function downstream of these two genes. It is concluded that CED-6 acts as an adaptor molecule in a signal transduction pathway that mediates the engulfment of apoptotic cells in *C. elegans*. The present inventors have also identified isolated and characterized human ced-6 homologue including a splice variant thereof, which it is shown is involved in a similar process in mammalian cells.

The invention provides, in isolated form, a protein which is the CED-6 protein of *C. elegans* or a protein which has equivalent function thereto and two human homologues of said protein, hereinafter referred to as h1 CED-6 and h2CED-6.

The invention further provides a functional fragment of CED-6, h1CED-6 and h2CED-6 for example, a fragment corresponding to the phosphotyrosine binding domain and/or the proline/serine rich region.

The invention further provides an isolated nucleic acid encoding CED-6 and two human homologues of CED-6, as well as nucleic acid encoding functional fragments of CED-6, h1CED-6 and h2-CED-6 as described above.

The invention further provides nucleic acid which is antisense to any of the nucleic acids described above or which is capable of hybridizing to any of the nucleic acids described above under conditions of low stringency or portions or fragments thereof.

The invention further provides expression vectors comprising nucleic acid encoding CED-6, h1CED-6, h2CED-6 or encoding functional fragments of said proteins as above.

The invention further provides mammalian cell-lines transfected with one or more nucleic acids encoding CED-6, h1CED-6 and h2CED-6.

The invention further provides assay methods using the proteins, nucleic acids and transfected cells described above to identify compounds which enhance or inhibit the signal transduction pathway in which CED-6, h1CED-6 and/or h2CED-6 participate.

The invention further provides assay methods using the transfected cells described above to identify compounds which enhance or inhibit the expression of the ced-6, h1ced-6 or h2ced-6 genes.

The invention further provides antibodies which react with an epitope of CED-6, h1CED-6 and/or h2CED-6.

The invention further provides a method of treating diseases the etiology of which may be attributed to failure of engulfment of apoptotic or other diseased cells such as inflammation autoimmune disease or cancer by administering to a patient one or more of the aforesaid proteins or nucleic acids or compounds which are enhancers of CED-6, h1CED-6 or h2CED-6.

The invention further provides a method of treating diseases which would benefit from a reduction in the engulfment of apoptotic cells, such as, neurodegenerative diseases stroke, or sickle-cell anaemia, by administering one or more of the aforesaid proteins, nucleic acids or compounds which are inhibitors of CED-6, h1CED-6 or h2CED-6.

The invention further provides a method of diagnosis of a human or animal disease using a nucleic acid encoding CED-6, h1 CED-6 or h2CED-6 or the complement thereof or an antibody to CED-6, h1CED-6 or h2CED-6 to detect a genetic defect.

The invention further provides a method of identifying proteins which interact with CED-6, h1CED-6 or h2CED-6 in the signal transduction pathway in which those proteins participate.

The invention further provides a fusion protein in which CED-6, h1CED-6 or h2CED-6 or a functional fragment thereof such as the phosphotyrosine binding domain or serine proline rich region, is fused to another protein such as an epitope tag or product of a reporter gene.

The invention further provides a method of determining whether a compound is an enhancer or Inhibitor of the signal transduction pathway in which CED-6 participates by observing the effect of the compound on *C. elegans* worms having altered CED-6 expression.

Figure 1A:
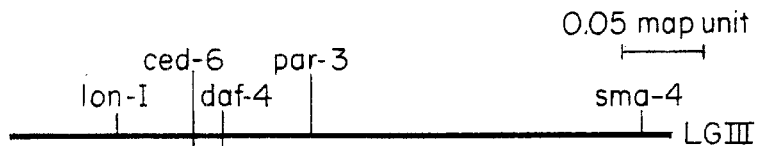
FIG. 1. The ced-6 Locus.
(A) Genetic Map of Ced-6.
  ced-6 and some genes close to and also used to map ced-6 are shown
(B) Cosmid Rescue.
  Transgenic animals carrying cosmids or subcloned DNA fragments (see C, D) were examined for cell corpses on three fold embryos. Those who gave embryos with partial or no cell corpses were counted as rescuing transgenic lines. Four out of tested thirteen cosmids are shown. Rescuing fragments are bold. Number represents # rescuing lines/# lines tested.
Figure 1B:
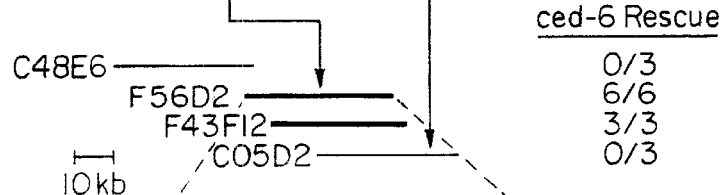
Figure 1C:
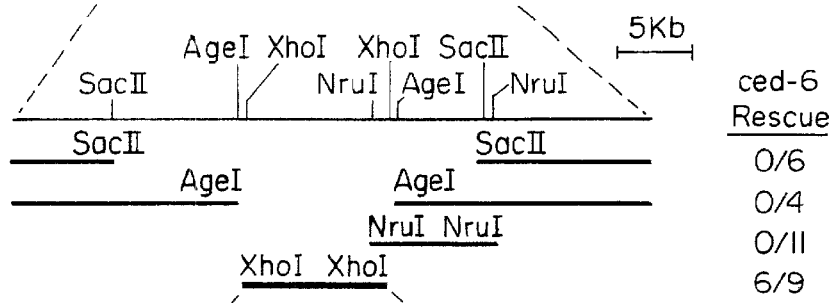
Figure 1D:
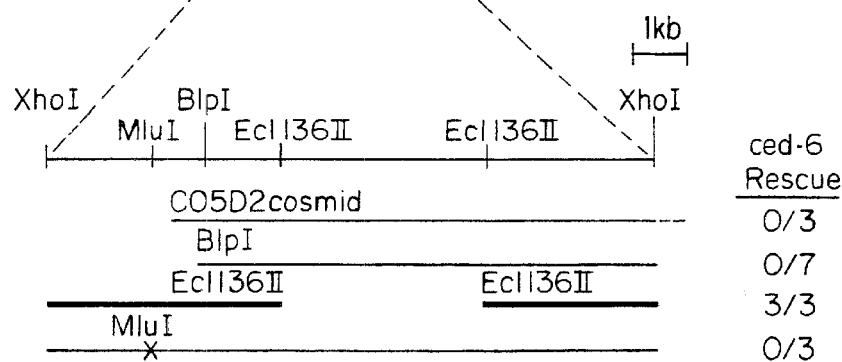

(C) Subcloning of F56D2 Cosmid and Rescue.

Restriction map of the ced-6 region is shown on the top. In the middle, several restriction fragments were tested for their ability to rescue the engulfment defect caused by ced-6(n1813).

(D) Subcloning of 10 kb Xho I Fragment and Rescue.

Restriction map of Xho I fragment is shown on the top, In the middle mutations made on the Xho I fragment and their rescuing ability are shown. An X indicates a frameshift mutation (see Experimental Procedures for details).

(E) Transcripts on Xho I Fragments

Intron/exon structure of the transcripts on Xho I fragment region. Boxes exons, V symbol: introns AAA: poly(A) tail. RT-PCR products of 5' end of F56D2.7 contain both SL1 and SL2.

FIG. 2. F56D2.7 Encodes CED-6(SEQ ID NO.: 2).

(A) F56D2.7 Full-length cDNA Sequence (SEQ ID NO.: 1).

Double underline indicates phosphotyrosine binding domain (nucleic acid: SEQ ID NO.: 3; amino acid: SEQ ID NO.: 4); single underline indicates proline/serine rich region (nucleic acid: SEQ ID NO.: 5; amino acid: SEQ ID NO.: 6). Dashed underline indicates charged region (nucleic acid: SEQ ID NO.: 7; amino acid: SEQ ID NO.: 8). Star identifies the prolines in the PxxP signature sequence, empty triangles the charged residues within the dashed region. Shaded box indicates polyadenylation signal, Both SL1 and SL2 could be added to transplicing acceptor site. The single base pair deletion identified in ced-6(n1813) is shown.

(B) Southern blot revealed a RFLP on 4.1 kb fragment from ced-6 (n2095).

Xho I probe identifies an allele-specific RFLP in ced-6 (n2095) that affect a 4.1 kb Hind III fragment containing F56D2.7. On the right bottom the genomic fragments digested by Hind III on the Xho I fragment region is shown. On the right top Xho I fragment and three genes covered on this region. Three Hind III fragments, 4.1 kb, 0.4 kb and 9.9 kb that should be lighted up on the Southern blot are indicated. On the left genomic DNA isolated independently from wild-type N2, ced-6(n1813) and ced-6(n2095) were probed with $^{32}$P-labeled Xho I fragment. n2095 allele showed the missing of the 4.1 kb fragment and the extra 2.1 kb fragment 0.4 kb fragments were not affected in both alleles (data on a separate gel, not shown here).

FIG. 3. CED-6 Contains a Phosphatyrosine Binding Domain.

(A) Alignment of CED-6 PTB with Other PTB Domain.

The PTB domain alignment was based on the NMR structure of Shc protein. Black boxes indicate identical amino acids showed by >50% of sequences. Grey boxes indicate similar amino acid showed by >50% of sequences. For this purpose, the following sets of amino acids are considered similar G, A, C, S, T; E, D, Q, N; R, K, H; V, M, L, I; F, Y, W α indicate the a helices suggested by the NMR structure of Shc, and β the β sheats, Invariant residues (found in all sequences shown) are highlighted by star, "*". The figure compares a portion of the amino acid sequence of C elegans CED-6 (SEQ ID NO.: 30) with C. Briggs (SEQ ID NO.: 31), a human amino acid sequence encoded by a Human EST (SEQ ID NO.: 32) Human SHC (SEQ ID NO.: 33), Drome SHC (SEQ ID NO.: 34), dNumb (SEQ ID NO.: 35), P96 (SEQ ID NO.: 36), Drome Disabled (SEQ ID NO.: 37), C. elegans M110.5 (SEQ ID NO.: 38), and Drome EST (SEQ ID NO.: 39).

(B) Comparison of CED-6 to Other PTB Domain Containing Proteins.

proline rich regions and charged regions next to PTB domains and other regions PTB domains were compared in the percentage of identity.

(C) Evolution Tree of the PTs Domains.

The alignment from (A) was displayed using Seqlab package in GCG program, and the evolution tree was grown graphically.

Figure 4:
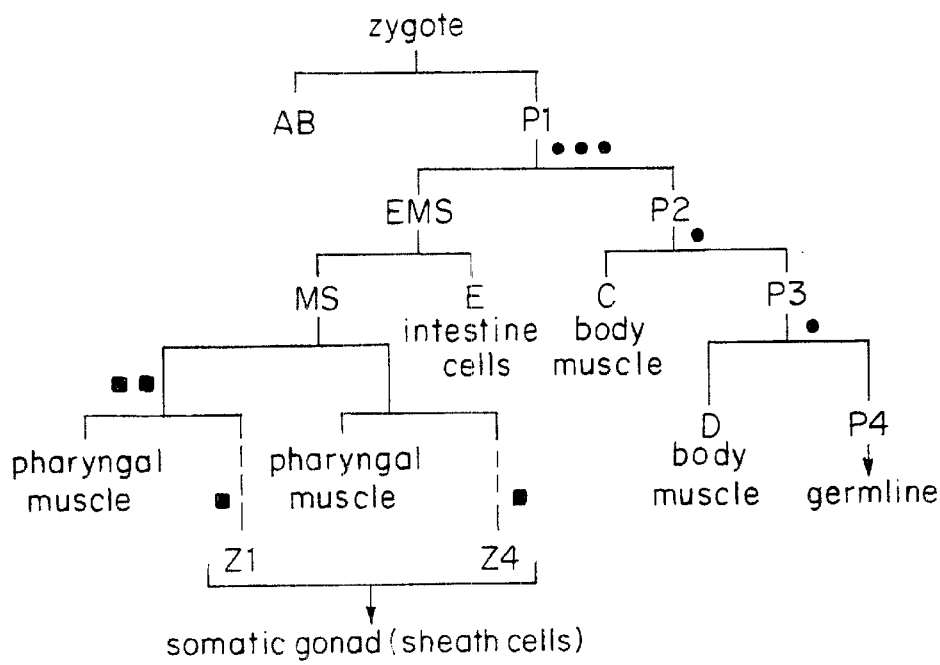

FIG. 4. The Genetic Mosaic Analysis for ced-6

Cell Lineage of C. elegans.

The descendence of both germline and somatic sheath cells are illustrated. Body wall muscles cells which were used to determine the loss of the duplication were also illustrated. The solid square indicates the duplication loss in germ cells, and the solid square indicates the duplication loss in the somatic sheath cells. The black arrow indicates the somatic sheath cell with the enlarged nucleoli in the distal arm of the anterior gonad. The white arrow indicates the cell corpses accumulated in the proximal arm of anterior gonad.

FIG. 5. Heat-shock overexpression of ced-6 cDNA rescued the engulfment defect in both soma and germline.

(A) Cell Death During the Embryonic Development.

Shaded box is a histogragh indicating the number of dying cells every 50 minutes during the embryonic development. The arrows indicates the timing of heat shock and the timing to observe the engulfment phenotype.

(B) Overexpression of ced-6 cDNA Promotes the Engulfment at Both the Early and the Late Stage of Cell Death.

Transgenic animals carrying the transgene, ced-6 cDNA driven by heat shock promoter were treated with heat before the cell death occurred at the indicated time. Cell Corpses in the head of young L1 larvae were examined. The animals without the heat treatment were also examined Other control experiments included N2, ced-6(n1613) with or without heat treatment, and ced-6(n1613) carrying lacZ transgene treated with heat. The solid circles indicate the experiments with the heat shock after the formation of cell corpses, and the empty circles with the heat shock before the cell death took place and the experiments without heat shock.

(C) Overexpression of ced-6 cDNA Rescue the Engulfment Defect in Germline.

The arrow indicates the timing for a heat shock when transgenic animals were at the development stage of the 24 hours after the L4 molt. Cell corpses were examined at the several time points between the time of heat shock and the 60 hours after the heat shock.

(D) Overexpression of ced-6 cDNA Promotes the Engulfment many Hours After the Formation of the Cell Corpses in Germline.

Adult transgenic animals were treated with heat as indicated. Cell corpses were examined in one gonad arm 12 hours after the heat shock. Control experiments including N2, and ced-6(n1813) are indicated in (C).

Figure 6A:
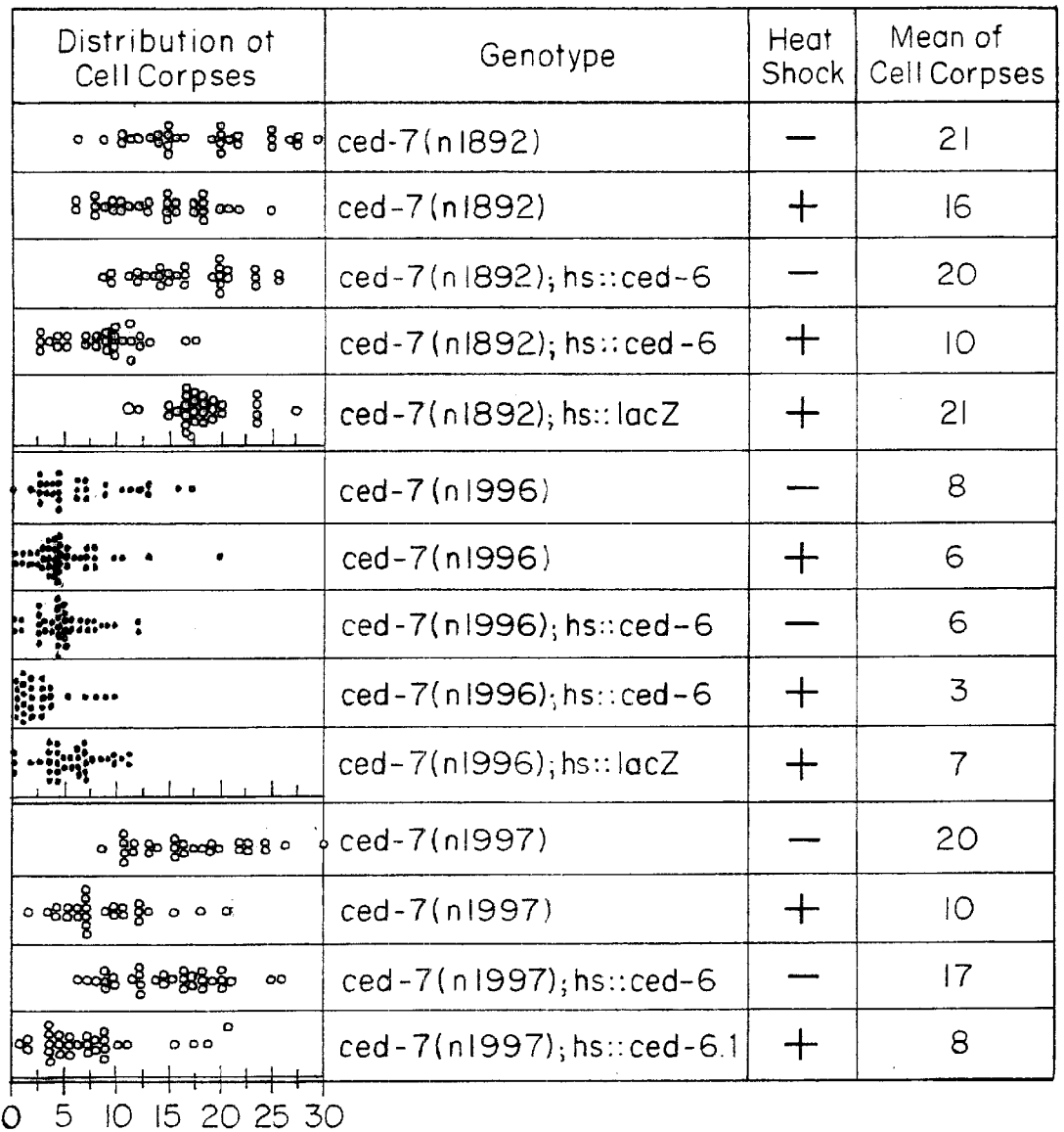
Figure 6B:
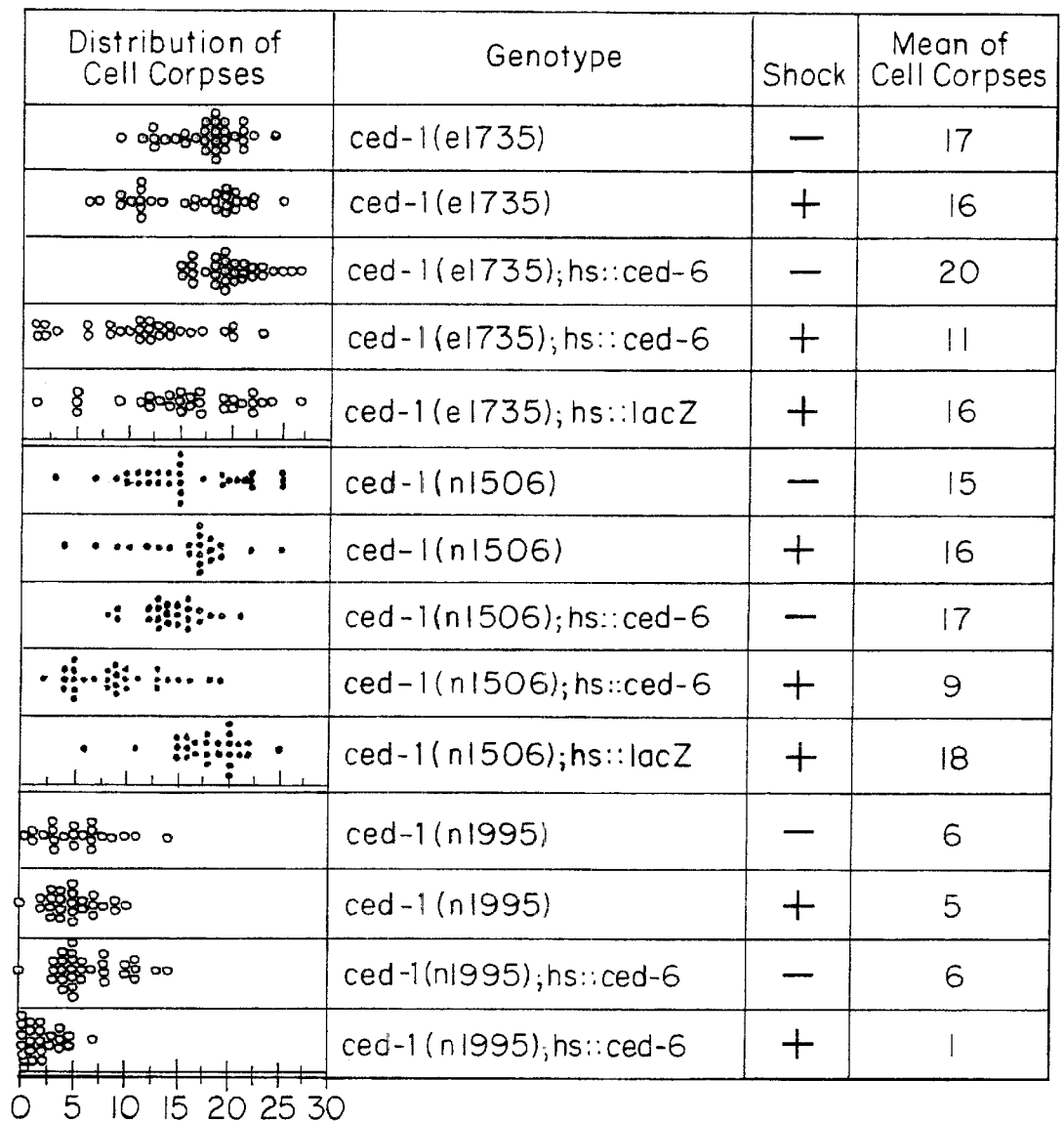

FIGS. 6A–6B. Overexpression of ced-6 Partially Suppresses the Engulfment Defect of both ced-1 and ced-7 During Embryonic Development ced-6 was overexpressed at the genetic background of three alleles of both ced-1 and ced-7.

Figures 5A, 5B:
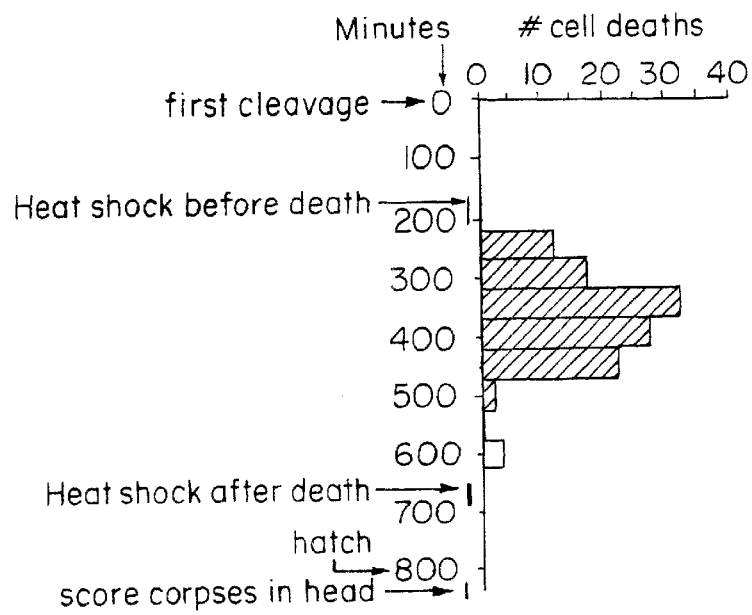

The timing for the heat shock and the timing for the examination of cell corpses are illustrated in FIG. 5A. Animals with each genetic background were treated with heat before the cell death occurred or without the heat treatment. Cell corpses were examined in head of young L1 larvae. LacZ was also expressed in the each genetic back ground. Each mutant was also treated with heat shock to Examine the effect of heat on the expression of cell corpses.

Figure 7:
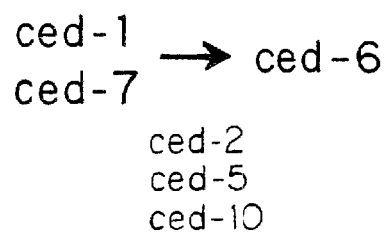

FIG. 7. Models
Epistatic Pathway for the Engulfment Genes

Overexpression of ced-6didn't have obvious effect on the cell corpses expression on ced-2, 5 and 10 but on ced-1 and ced-7. We propose that ced-6 might act downstream of both ced-1 and ced-7. And ced-2, 5 and 10 either act in the different pathway or act downstream of cede6.

FIG. 8.

Figure 8:
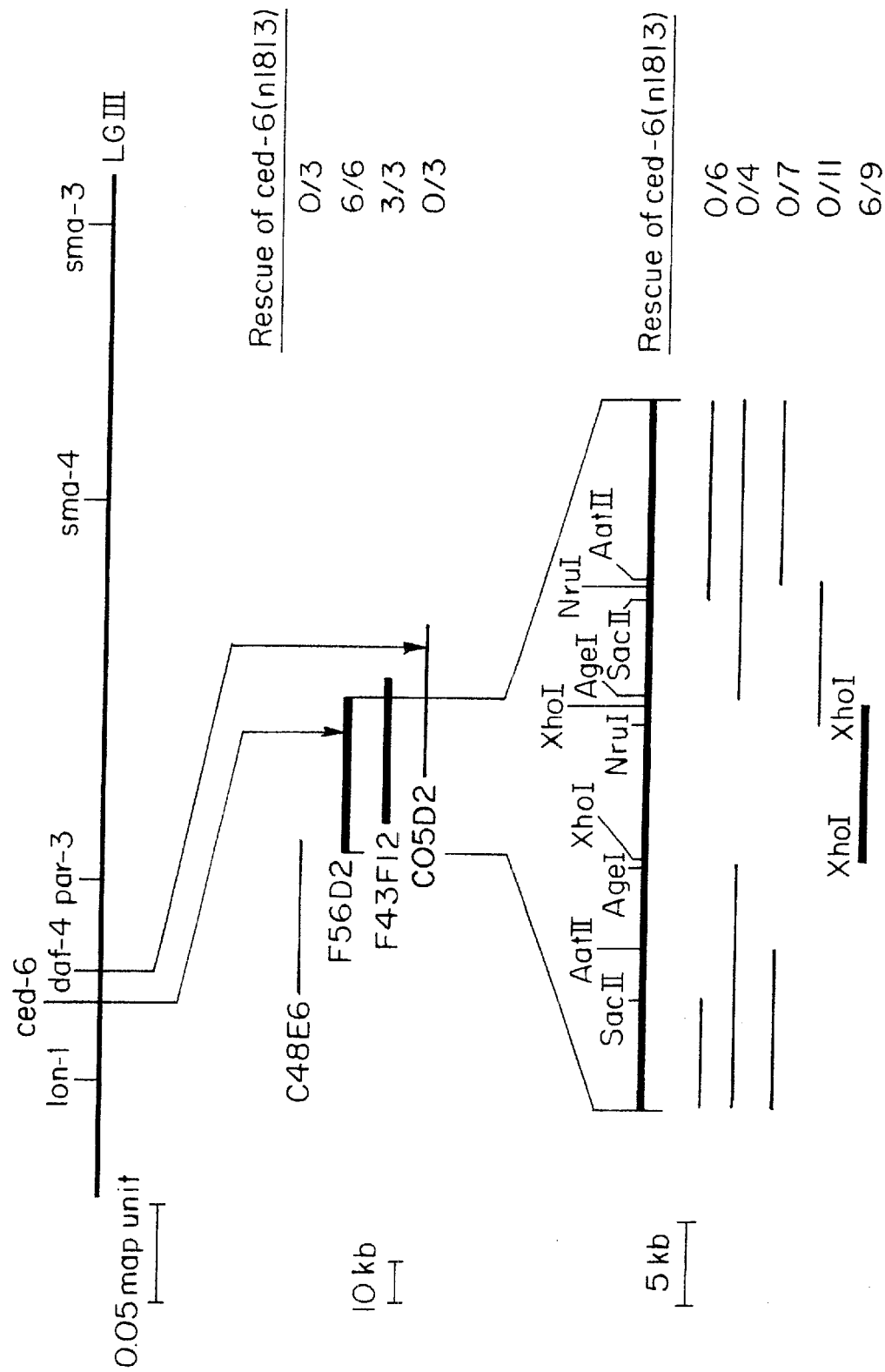

FIG. 8 is a flow chart illustrating a Xho I fragment from F56 cosmid rescues the ced-6 engulfment defect.

FIG. 9.

FIG. 9 illustrates that the C05D2.7 construct is ced-6, FIG. 9A shows the restriction Map of Xho I fragment and rescue. FIG. 9B shows the transcripts.

FIG. 10.

Figure 10:
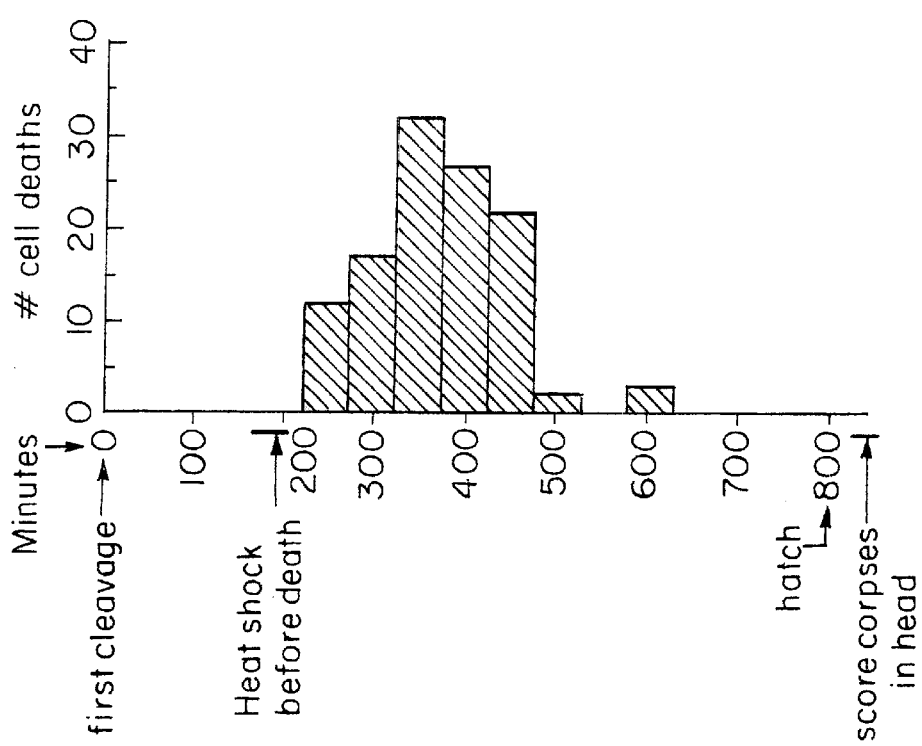

FIG. 10 is a bar graph illustrating that the over-expression of ced-6 rescues the engulfment defect of the ced-6 mutant.

FIG. 11.

Figure 11:
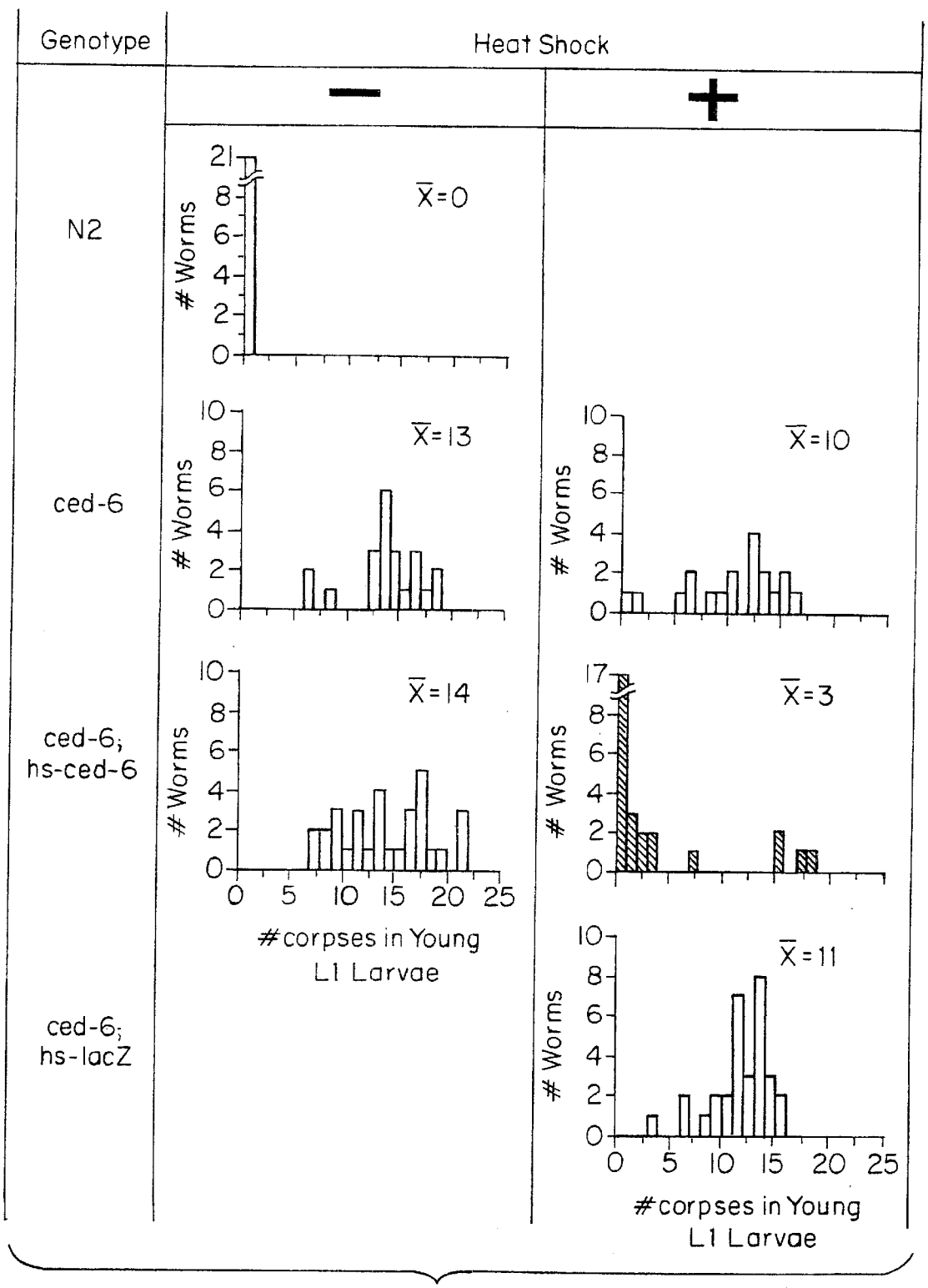

FIG. 11 contains graphs illustrating that the over-expression of ced-6 rescues the engulfment defect of ced-6 mutant during embryonic development.

FIG. 12.

Figure 12:
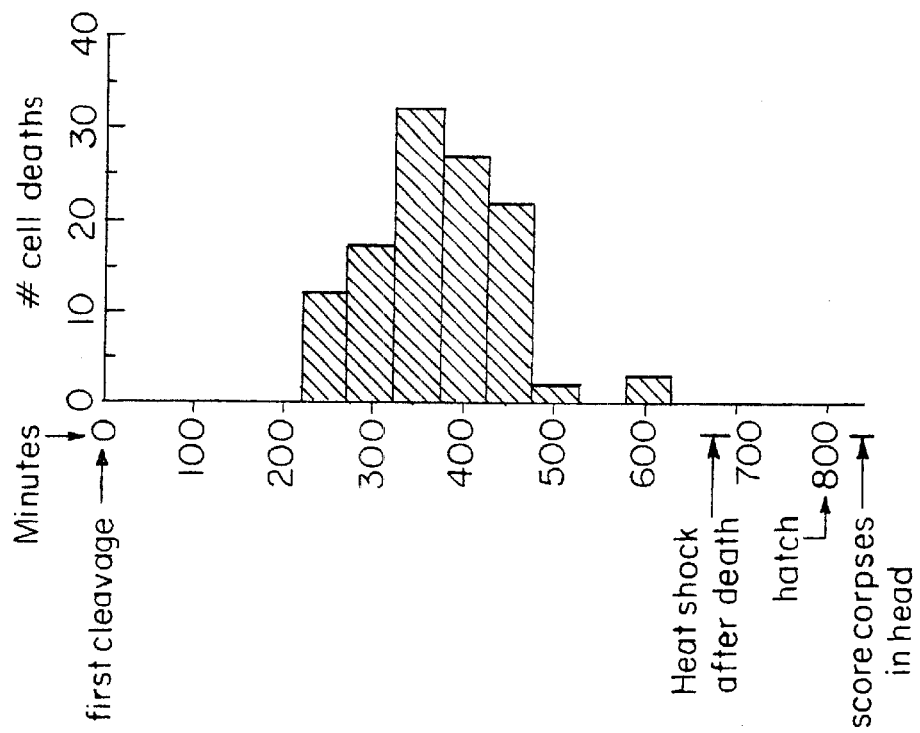

FIG. 12 is a bar graph illustrating that ced-6 may also promote the engulfment of persisting corpses.

FIG. 13.

Figure 13:
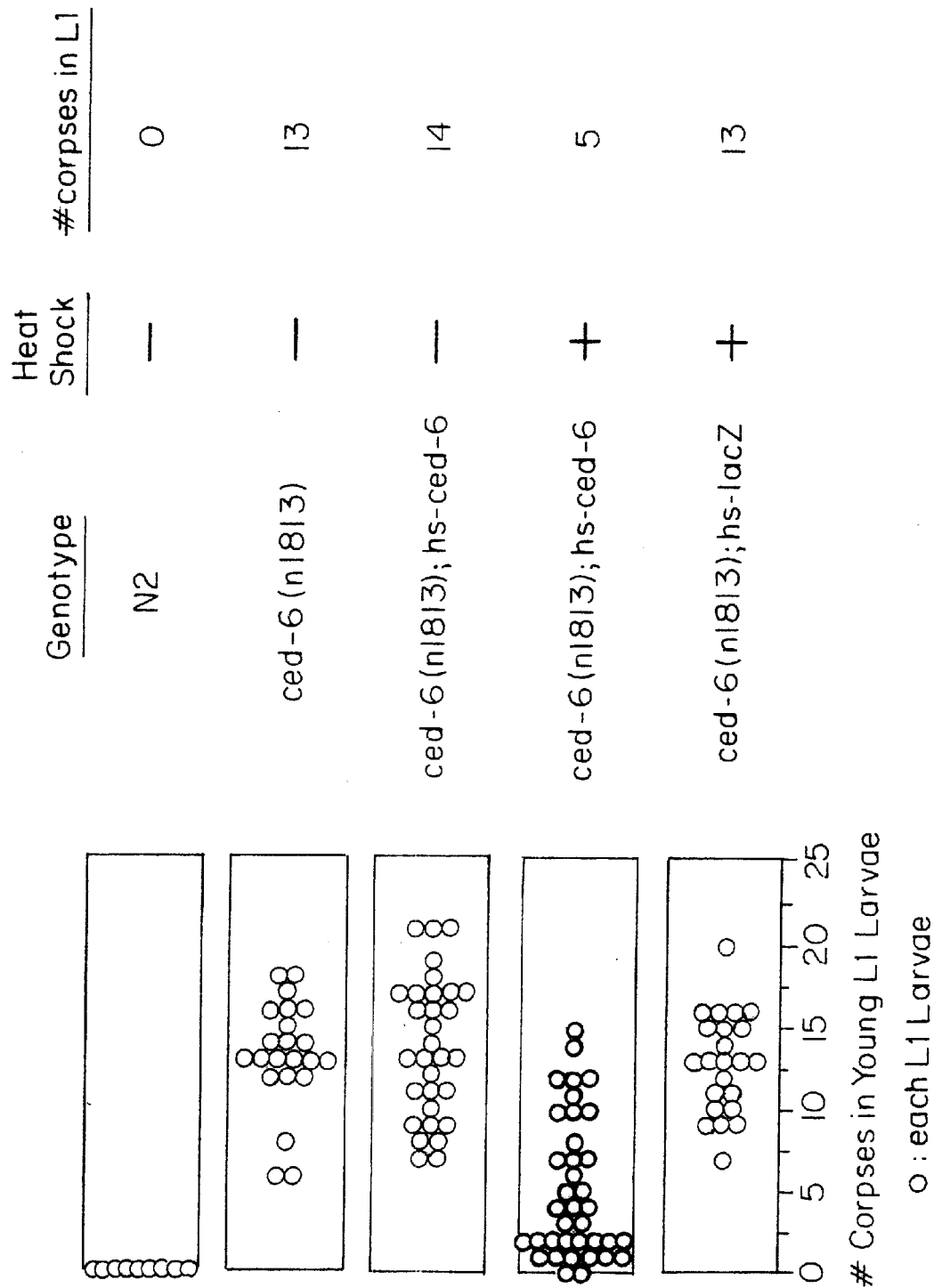

FIG. 13 shows that ced-6 promotes the engulfment of persistent cell corpses and probably acts within engulfing cells.

FIG. 14.

Figure 14:
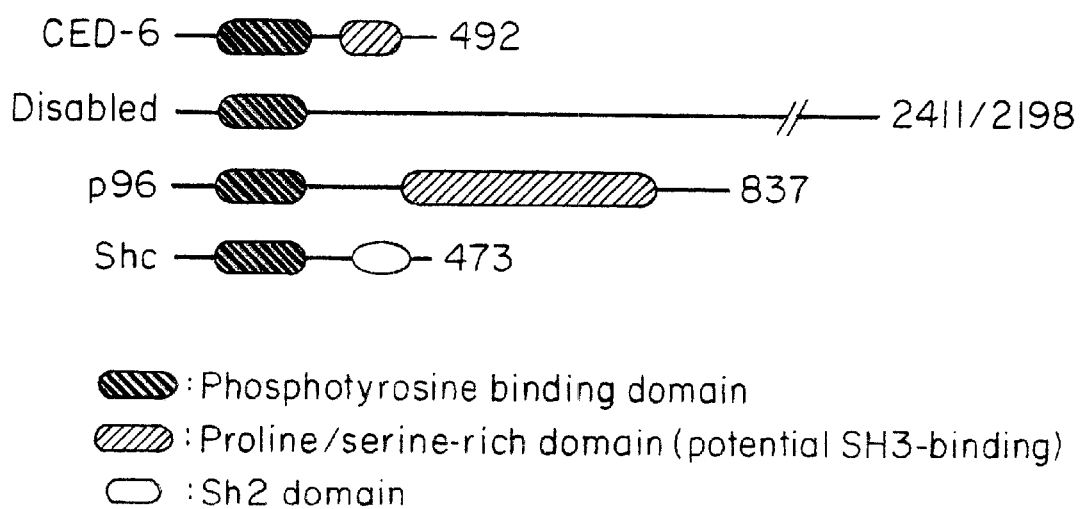

FIG. 14 shows that ced-6 may be an adaptor protein acting in signal transduction pathway.

FIG. 15.

Figure 15:
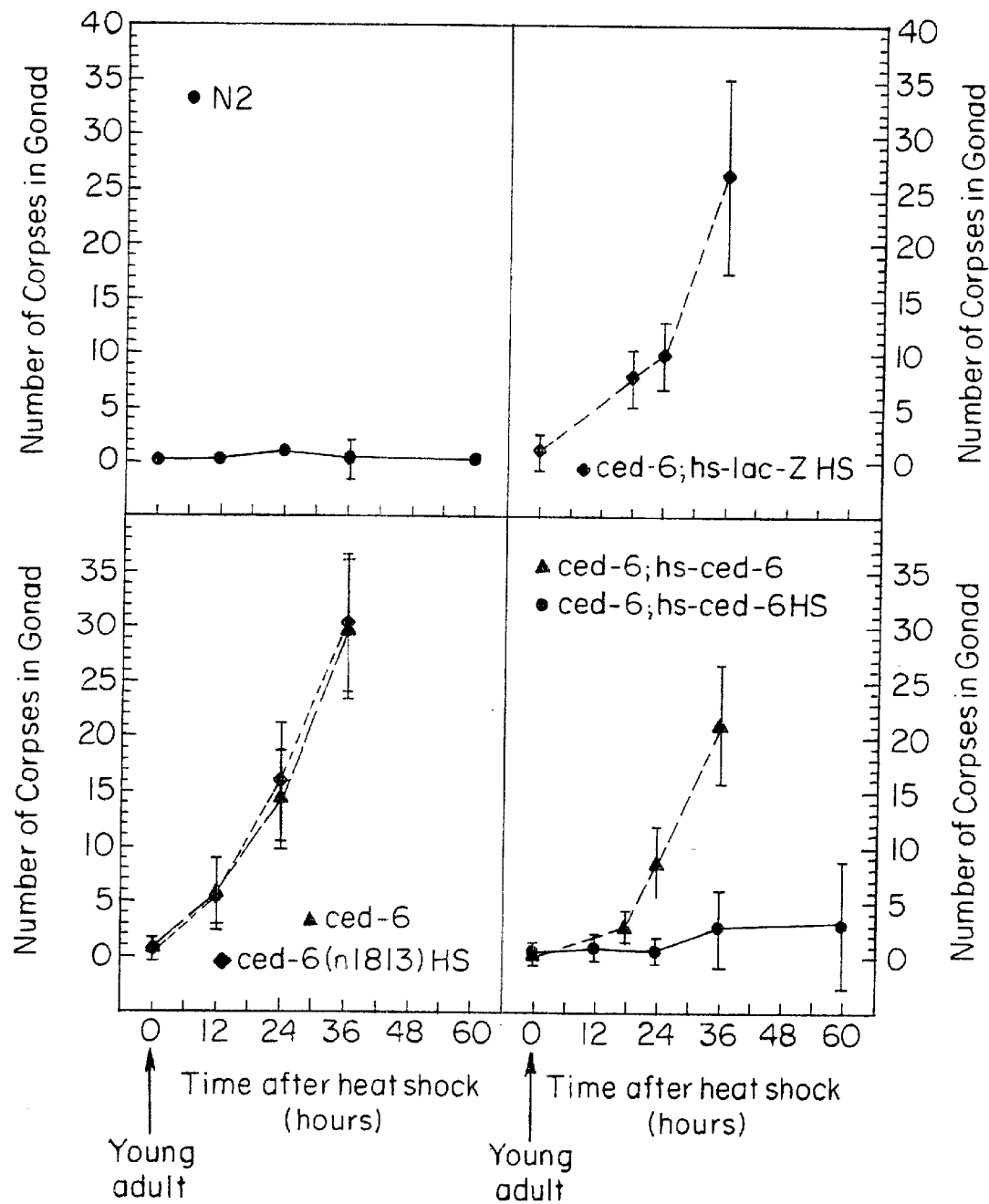

FIG. 15 shows graphs which indicate that over-expression of ced-6 rescues the engulfment defect in the adult gonad, and ced-6 might act in somatic sheath cells.

FIG. 16.

Figure 16:
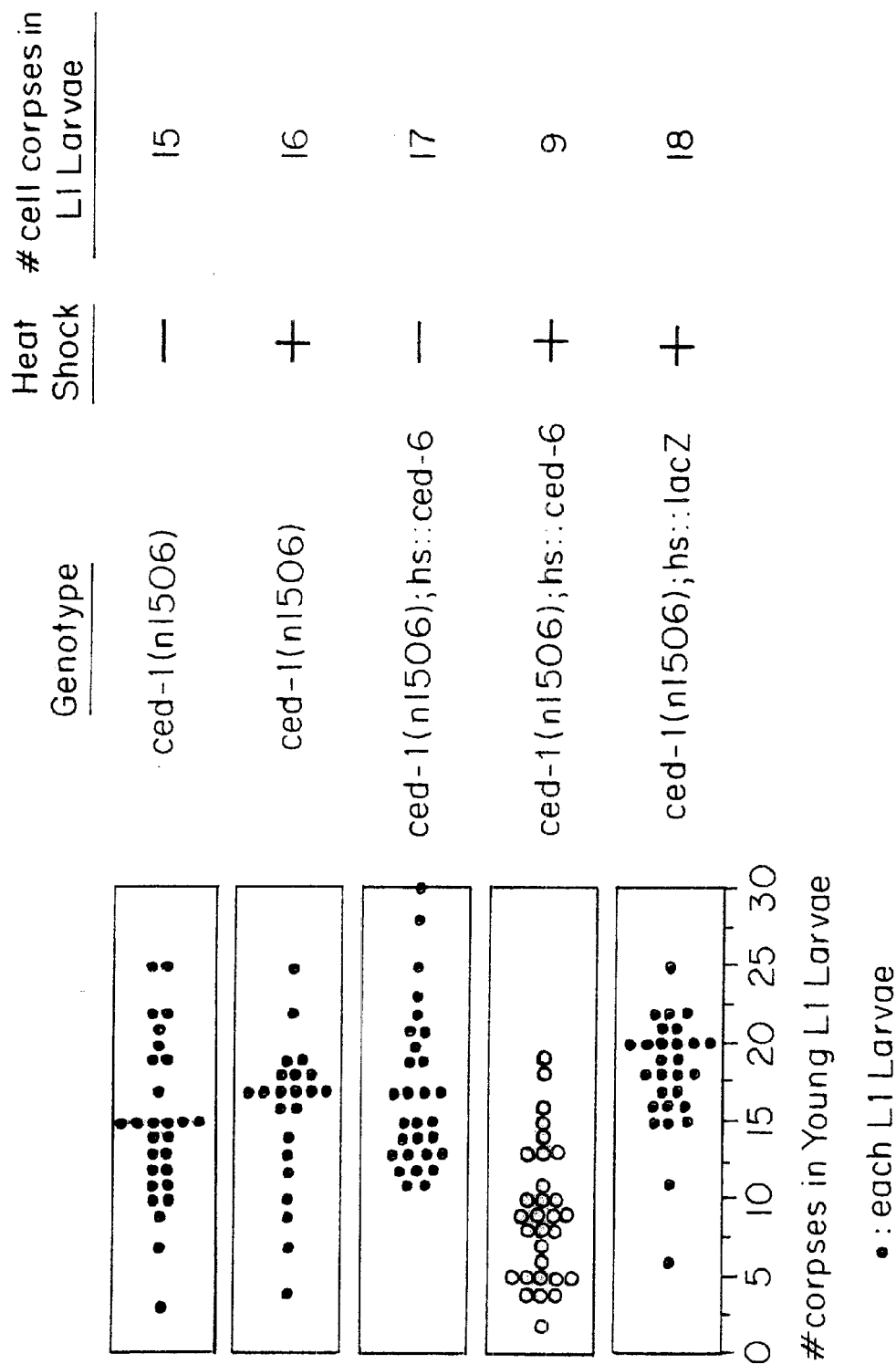

FIG. 16 illustrates that over-expression of ced-6 partially suppresses the engulfment defect of ced-1 mutants.

FIG. 17.

Figure 17:
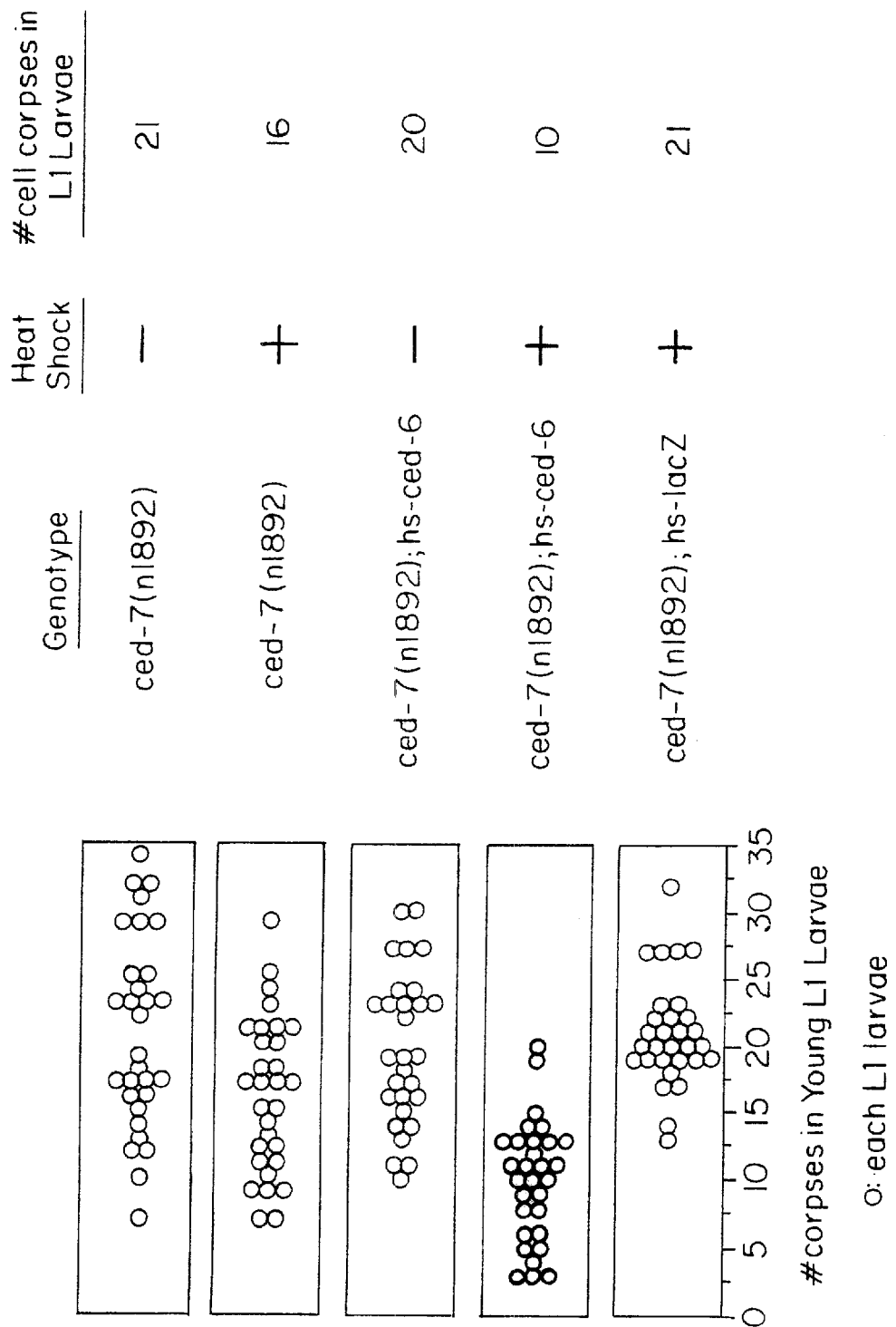

FIG. 17 shows that the over-expression of ced-6 cDNA suppresses the engulfment defect of ced-7 mutants.

FIG. 18 shows consensus DNA sequence of h1ced-6 (2416bp); SEQ ID NO.: 9 with start and stop codon in bold and alternatively spliced sequence underlined.

FIG. 19 shows DNA sequence of h2ced-6 (alternative splice; SEQ ID NO.: 17) with start and stop codons in bold.

FIG. 20 shows the amino acid sequence of h1CED-6 (SEQ ID NO.: 10) with alternatively spliced region underlined.

FIG. 21 shows the amino acid sequence of h2CED-6 (alternative splice; SEQ ID NO.: 18).

FIG. 22 shows h1ced-6 cDNA and h1CED-6 amino acid sequence with PTB (nucleic acid: SEQ ID NO.: 11; amino acid: SEQ ID NO.: 12) domain, charged region (nucleic acid: SEQ ID NO.: 15; amino acid: SEQ ID NO.: 16) and proline/serine rich region (nucleic acid: SEQ ID NO.: 13; amino acid: SEQ ID NO.: 14) indicated.

Figure 23:
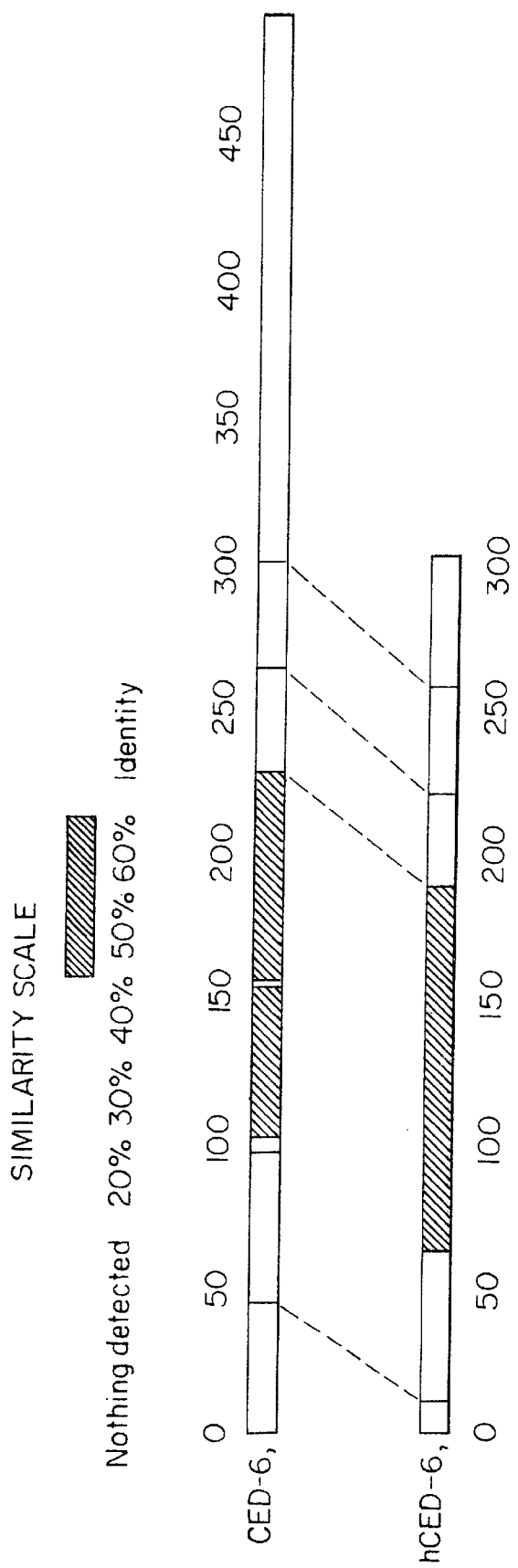

FIG. 23 shows an alignment of CED-6 and h1CED-6.

FIG. 24 shows an alignment of regions of 47.5% and 31.6% identity respectively.

FIG. 25 shows a Human Multiple Tissue Northern (MTN) Blot, a Human Multiple Tissue Northern (MTN) Blot II, and a Human Cancer Cell Line Multiple Tissue Northern (MTN™) Blot.

Figure 26:
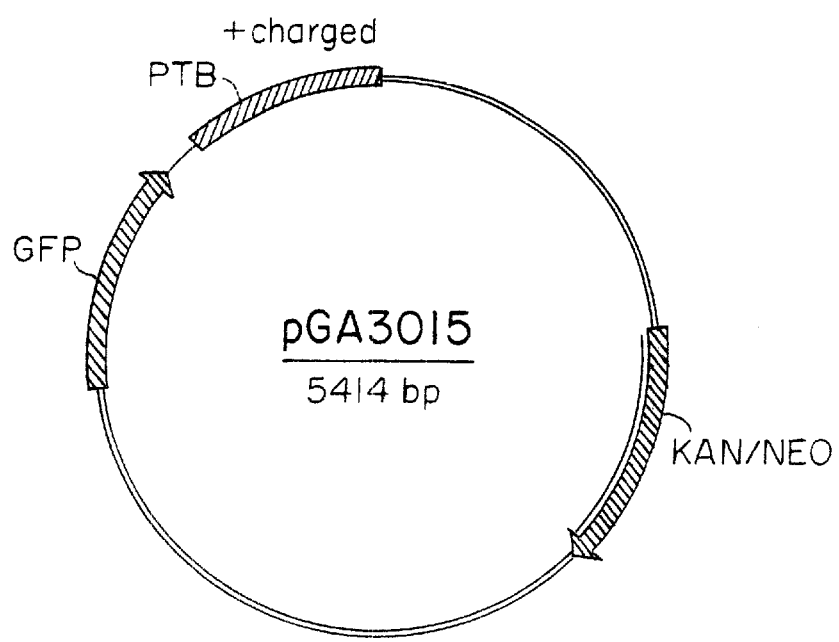

FIG. 26 is a map of plasmid pGA3015 in which a CED-6 fragment is cloned as a C-terminal fusion to GFP.

Figure 27:
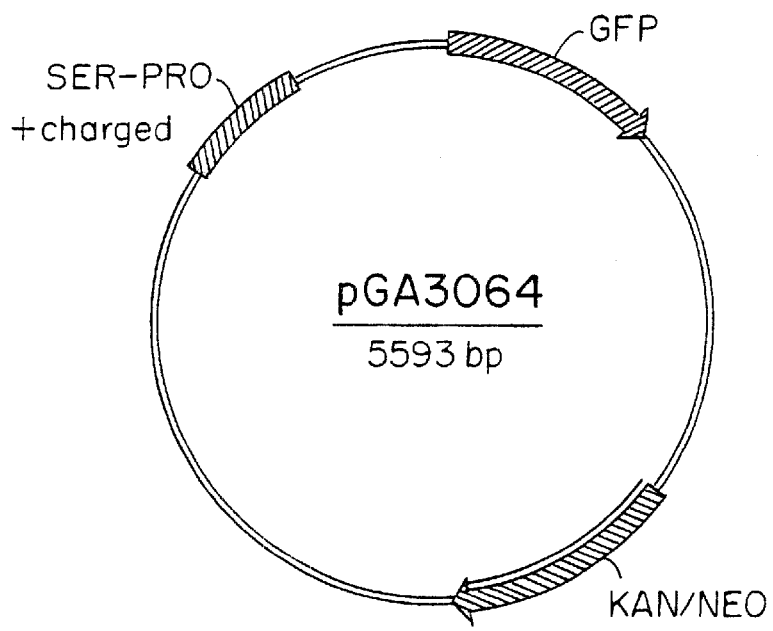

FIG. 27 is a map of plasmid pGA3O04 with CED-6 cloned as a C-terminal fusion of GFP.

FIGS. 28A–28F is a DNA alignment (Genework) of sequenced hbc3123 EST clone, the PCR fragment I isolated from a cDNA library, and three EST sequences identified using the PCR fragment. The cDNA library (including eight human tissues) is a gift from Dr. Wigler's lab. hbc3123 EST clone was sequenced and analyzed in January 1997. The three EST clones were identified through searching the Genbank using the isolated PCR fragment. The figure aligns the following sequences: R65983 (SEQ ID NO.: 40), the PCR fragment (SEQ ID NO.: 41), hbc3123 EST (SEQ ID NO.: 42), R65882 (SEQ ID NO.: 43), and AA159394 (SEQ ID NO.: 44).

DEPOSITED MATERIAL cDNAs encoding the alternative splice h2CED-6 and the additional sequence required to constitute h1ced-6 from h2ced-6 have been deposited a the Belgian Coordinated Collections of Microorganisms (BCCM) at Laboratorium voor Moleculaire Biologie—plasmidencollsective (LMBP) B 9000, Gent, Belgium in accordance with the Budapest Treaty on Jun. 8, 1998 and have been accorded the Accession Nos. LMBP 3868 and LMBP 3869 respectively.

Primers which will assist in obtaining the relevant inserts from these deposits are shown in Example 14.

AMINO ACID AND NUCLEOTIDE SEQUENCES DISCLOSED HEREIN ARE AS FOLLOWS

Figure 2A:
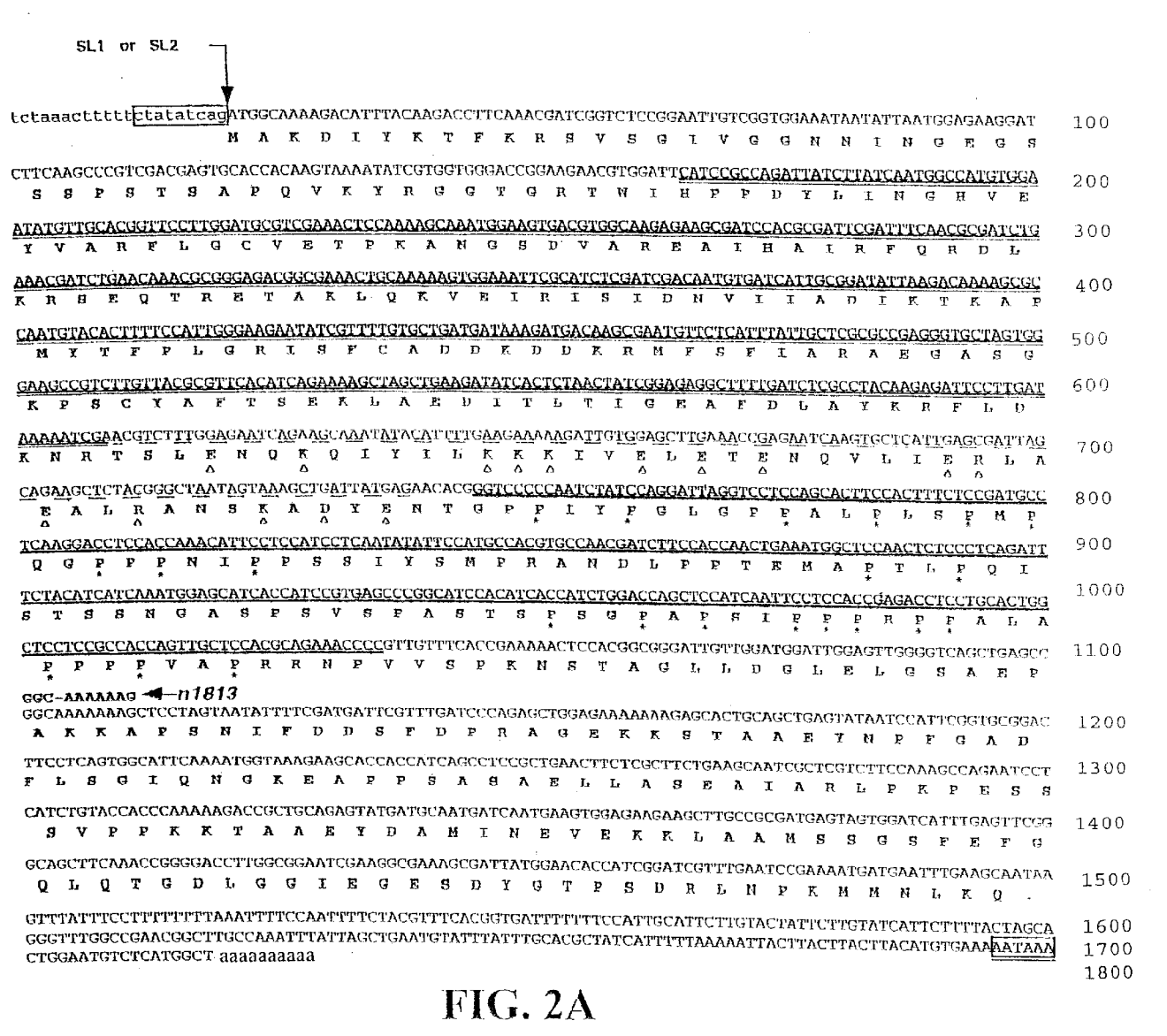

| | |
|---|---|
| SEQ. ID NO. 1 | Nucleotide sequence of C. elegans CED-6, as Shown in FIG. 2A |
| SEQ. ID NO. 2 | amino acid sequence of C. elegans, as shown in FIG. 2A |
| SEQ. ID NO. 3 | Nucleotide sequence a10 FIG. 2A |
| SEQ. ID NO. 4 | Amino acid sequence of PTB domain of C. elegans Ced-6 as Shown in FIG. 2A |
| SEQ. ID NO. 5 | a11 proline/serine rich region C. elegans Ced-6, as Shown in FIG. 2A |
| SEQ. ID NO. 6 | a12 |
| SEQ. ID NO. 7 | Nucleotide sequence encoding the Charged region of C. elegans Ced-6, as shown in FIG. 2A |
| SEQ. ID NO. 8 | Amino acid sequence of a13 |
| SEQ. ID NO. 9 | Nucleotide sequence encoding human CED-6(h1CED-6), as shown in FIG. 18 and 22 |
| SEQ. ID NO. 10 | Amino acid sequence of A1 CED-6, as shown in FIG. 18 and 22 |
| SEQ. ID NO. 11 | Nucleotide acid sequence encoding PTB domain of h1CED-6/ as shown in FIG. 18 and 22 |
| SEQ. ID NO. 12 | Amino acid sequence encoding PTB domain of h1CED-6/as shown in FIG. 20 and 22 |
| SEQ. ID NO. 13 | a14 |
| SEQ. ID NO. 14 | a15 |
| SEQ. ID NO. 15 | a16 |
| SEQ. ID NO. 16 | a17 |

C. ELEGANS CED-6

Programmed cell death has traditionally been divided into two distinct, sequential processes: cell killing, and the removal of dead cells. However, these two events are very closely linked. In vivo, cells that present an apoptotic morphology are usually already engulfed by other cells (Wyllie A. H. et al. 1980 Int. Rev. Cytol 68, 251–306; Lockshin R. A. (1981) Cell Death in Biology and Pathology, R. A. Lockshin and I. D. Browen, eds. (London: Clapman and Hall), pp79–122; Duvall and Wyllie (1986). Immunol Today 7 pp 115–119 Robertson and Thompson (1982) J. Embryol. Exp. Morph. 67 pp 89–100: Hedgecock et al.

(1983) Science 222, 1277–1279; Ellis et al. (1991) Genetics 129 pp 79–94;). Engulfment is also a swift and efficient process in the nematode *Caenorhabditis elegans*: dying cells are engulfed and completely removed by their neighboring cells within an hour (Sulston and Horvitz, (1977); Dev. Biol 56pp 110–156; Robertson and Thomson, 1982). The engulfment is not necessarily by professional phagocytes. Rapid engulfment of apoptotic cells is important, as it prevents dying cells from releasing potentially harmful contents during their lysis, which could damage surrounding tissue and result in an inflammatory response (Duvall et al., (1985) Immunology 56 pp 351–358; Savill et al., (1989) J. Clin. Invest. 83 pp 865–875; Grigg et al., (1991) Lancet 358 pp 720–722; Savill et al., (1993) Immunol. Today 14, pp 131–136).

The nematode *C. elegans* has been used extensively for the study of programmed cell death (reviewed by Hengartner, (1997) Cell Death in *C. elegans* II, Plain View, Cold Spring Harbour Laboratory Press, pp 383–415). Genetic studies have identified over a dozen genes that function in the regulation and execution of apoptosis in *C. elegans*. Six genes—ced-1, ced-2, ced-5, ced-6, ced-7, and ced-10—function in the engulfment of all dying ceals (Hedgecock et al., 1983; Ellis et al., 1991; Horvitz et al., (1994) Cold Spring Harbour Symp. Quant Biol (1994) 59 pp 377–385). In animals mutant for any one of these genes, many apoptotic cells fail to be engulfed and persist for many hours as highly refractile disks that can be readily identified under differential interference contrast (DIC) optics (Hedgecock et al., 1983; Ellis et al., 1991). None of the six engulfment genes is absolutely essential for engulfment, as many dying cells are still properly removed in these mutants. Genetic analysis of various double mutants has suggested that these six genes might form two partially redundant groups, one being comprised of ced-1, ced-6, and ced-7; the other of ced-2, ced-5, and ced-10 (Ellis et al., 1991). The number of persistent cell corpses is increased dramatically in double mutants crossing groups, but not in those within the same group. Understanding how these genes are involved in regulating engulfment requires the elucidation of their molecular nature.

In other species, several candidate apoptotic receptors have been identified over the past few years; these include the ATP-binding cassette transporter ABC1 (Luciani and Chimini, (1996), EMBO J. 15 pp 226–235) adhesion molecules such as the vitronectin receptor (Savill et al. (1990). Nature 343 pp 170–173) and CD36 (Asch et al. (1987) J. Clin. Invest 79 pp 1054–1061; Savill et al. (1992) J. Clin. Invest. 90 pp 1513–1522; Ren et al (1995) J. Exp. Med. 18 1857–1862), Drosophila croquemort (Franc et al., (1996), Immunity 4, pp 431–443 class A scavenger receptors (Platt et al., (1996), Proc. Natl. Acad. Sci. USA 93 pp 12456–12460) lectins (Duvall et al., (1985), and a predicted receptor that can recognize phosphatidylserine on the outer leaflet of apoptotic ceils (Fadok et al., (1992) J. Immunol. 148 pp 2207–2216; Fadok et al. (1992) J. Immunol 149 pp 4029–4035). Currently little is known about the molecules used by engulfing cells to transduce signals from surface receptors to the cytoskelaton, or how these molecules regulate the local cytoplasmic rearrangements and dynamic extensions that are required for phagocytosis (Savill et al., 1993). A genetic analysis of engulfment in *C. elegans* could identify genes involved in these processes. Indeed Wu and Horvitz (1998) (Nature 392 pp 501–504) showed that *C. elegans* CED-5 is homologous to human DOCK180, and might regulate cytoskeleton rearrangement during engulfment.

The process of apoptosis has been implicated in the etiology—or associated with the pathology—of a wide range of diseases, including cancer, autoimmune diseases, various neurodegenerative diseases such as Amyotrophic Lateral Sclerosis, Huntington's Disease, and Alzheimer's Disease, stroke, myocardial heart infarct, and AIDS (Thompson, (1995) Science 267 pp 1456–1462). Thus, a better understanding of the molecular events that underlie apoptosis might lead to novel therapeutic interventions. While much of the current attention is centered on the genes and proteins that control the killing step of the death process, it is very likely that the removal of apoptotic cells will prove to also be crucial for the proper overall functioning of the apoptotic program, and will offer another entry point for therapeutic intervention (see below).

The process of recognition and engulfment of dying cells is extremely swift and efficient. In animals, it is essentially impossible to find a cell With apoptotic features that is not already within another cell. Such rapid recognition and phagocytosis of apoptotic cells is a crucial aspect of programmed cell death in vivo: unengulfed apoptotic bodies can undergo secondary necrosis, leading to inflammation. Failure to remove apoptotic bodies also exposes the body to novel epitopes (from erg., caspase-generated protein fragments), possibly encouraging the development of autoimmune disease Persistent apoptotic bodies can often be observed following chemotherapeutic intervention (which leads to extensive apoptosis) and are particularly abundant in solid tumors, in which clearance of cell corpses might be delayed.

In addition to their ability to recognize and engulf apoptotic cells, professional phagocytes carry specific surface receptors, such as the Fc (Ravetch, (1994) Cell 78 553–560; Greenberg et al., (1993) J. Exp. Med. pp 529–534) and C3 (Bianco et al., (1975) J. Exp. Med. 141 pp 1278–1290; Greenberg, (1995) Trends in Cell Biol. 5 pp 93–99) receptors, which recognize antigen-opsonized particles and trigger their phagocytosis. Inhibitor studies have shown that Fc receptor-mediated phagocytosis requires tyrosine phosphorylation (Greenberg et al., 1993; Greenberg, 1995). The work of the present inventors suggests that the engulfment of apoptotic cells could be also mediated by a tyrosine kinase signal transduction pathway. While these two pathways clearly use distinct receptors at the cell surface they must eventually converge on the same downstream engulfment machinery, and could thus share at least some common signal transduction molecules.

In accordance with the invention there is provided an isolated protein which is an adaptor molecule In a signal transduction pathway which regulates phagocytosis of apoptotic cells.

In a particular embodiment in accordance with the invention there is provided an isolated protein from the nematode worm *C. elegans* which is an adaptor molecule acting in a signal transduction pathway which promotes phagocytosis of apoptotic cells, which protein comprises the amino acid sequence shown in FIG. 2A (SEQ ID NO.: 2) or an amino acid sequence which differs from FIG. 2A only in conservative amino acid changes. As aforesaid the amino acid sequence shown in FIG. 2A is that of the *C. elegans* CED-6 protein with its encoding DNA also shown.

In another of the aspects the invention comprises a nucleic acid comprising a sequence of nucleotides which encodes the amino acid sequence of FIG. 2A, (SEQ ID NO: 1) for example, a sequence of nucleotides from about nucleotide position 22 to about nucleotide position 1500 of FIG. 2A or the entire sequence of nucleotides shown in FIG. 2A (SEQ ID NO: 1).

In a further embodiment of the invention there is provided an isolated protein which is a fragment or portion of a protein having the amino acid sequence of FIG. 2A or of a protein having an amino acid sequence which differs from that shown in FIG. 2A only in conservative amino acid changes. For example the portion may comprise an amino acid sequence corresponding to the phosphotyrosine binding domain (SEQ ID NO: 4) (about amino acid 46 to about amino acid 193 in FIG. 2A) or an amino acid sequence corresponding to the proline/serine rich region (SEQ ID NO: 6) (about amino acid 242 to about amino acid 339 in FIG. 2A) or an amino acid sequence of the charged region (SEQ ID NO.: 8).

Nucleic acids (SEQ ID NOS.: 3, 5 or 7) encoding the above portions are provided in accordance with the invention.

In yet a further aspect of the invention there is provided an isolated nucleic acid capable of hybridizing to the sequence of nucleotides of SEQ ID NOS:1, 3, 5 or 7 under conditions of low stringency. It is to be understood that low stringency means: 0.2 to 2×SSC: 0.1% SDS; 25° to 50° C.

In a further embodiment of the invention there is provided a fusion protein which comprises as part of the fusion a protein having an amino sequence of SEQ ID NOS: 2, 4, 6 or 8 or an amino acid sequence which differs from the amino acid sequence shown in SEQ ID NOS: 2, 4, 6 or 8 only in conservative amino acid changes. The protein may be fused to for example, an epitope tag or the expression product of a reporter gene.

In yet a further aspect the invention provides expression vectors comprising any of the nucleic acid sequences of SEQ ID NOS: 1, 3, 5 or 7. Preferably said vectors incorporate a reporter gene such as green fluorescent protein which is positioned relative to the nucleic acid of the invention such that expression of the nucleic acid results in expression of the reporter gene. Preferably, a fusion of CED-6 and the reporter gene is expressed.

It is to be understood that the term "nucleic acid" as used herein may include both DNA and RNA and genomic as well as cDNA.

As aforesaid the present inventors have used the positional cloning method to clone the C. elegans ced-6 gene and determine the nucleotide sequence. In addition they have functionally characterized the protein. By searching publicly available protein sequence databases it has been determined that the CED-6 protein has in the N-terminal half a putative phosphotyrosine binding domain and in the C-terminal half a proline/serine rich region which is a potential SH3 binding domain.

Genetic mosaic analysis, as well as rescue and overexpression experiments, have shown that ced-6 acts autonomously within engulfing cells and promotes engulfment of apoptotic cells. Further database searching has confirmed the functional regions to be surprisingly evolutionally conserved. Thus, the inventors have now cloned two human homologues of the C. elegans ced-6 gene and shown them to have equivalent function.

Molecular Cloning of C. elegans ced-6

Previous genetic mapping experiments by Ellis and Colleagues (Ellis et al., (1991) (Genetics 129 pp 79–94) have placed ced-6 gene lose to the daf-4 locus on chromosome three (FIG. 1A). The region around daf-4 has been mostly sequenced by the C. elegans genome sequence consortium (Wilson et al., (1994) Nature 368 pp 32–38). To determine the exact physical location of ced-6, the present inventors collected thirteen overlapping cosmids in this region which together are roughly 0.3 Mbp. Using the germline transformation method (Mello and Fire, (1995), methods in cell biology (San Diego Academic Press) pp 452–482)these cosmids were tested for their ability to rescue the engulfment defect of ced-6(n1813), by scoring threefold embryos laid by transgenic animals for the presence of persistent cell corpses. Three fold embryos were chosen for the initial study because cell corpses are numerous and easily seen at this stage of development, Two overlapping cosmids F56D2 and F43F12 were found to be able to rescue the engulfment defect of ced-6(n1813). The further rescuing experiments using the DNA fragments from F56D2 were identified to contain the rescuing activity.

Figure 1E:
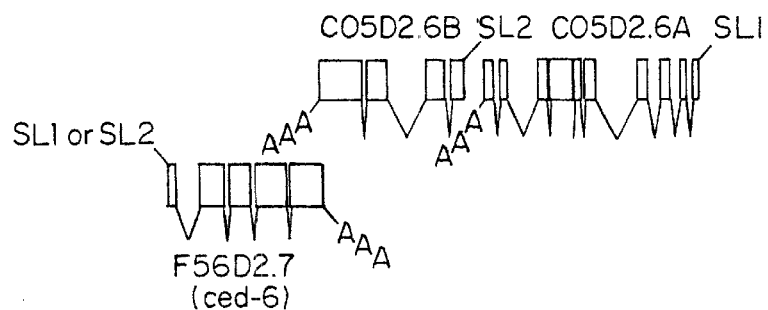

The gene prediction program GENEFINDER™ suggested that this region contains two genes, which the C. elegans genome sequence consortium submitted to Genbank under the names F56D2.7 and C05D2.6. Using a combination of RT-PCR and screening of cDNA libraries (see below) the existence and predicted intron/exon pattern of F56D2.7 was confirmed. However, the inventors found that C05D2.6, rather than corresponding to a single gene, actually corresponds to two genes and the short distance (>>>bp) between the end of the upstream transcript and the start of the downstream transcript suggested that C05D2.6A/B might be a two-gene operon (Zorio et al. (1994) Nature 372 pp 270–272.). In support of this hypothesis, it was found that C05D2.6B is trans-spliced to the "downstream" splice leader SL2, whereas the upstream transcript C05D2.6A is trans-spliced to the more common SL1 splice leader (FIG. 1E).

The ced-6 Locus

Figure 2B:
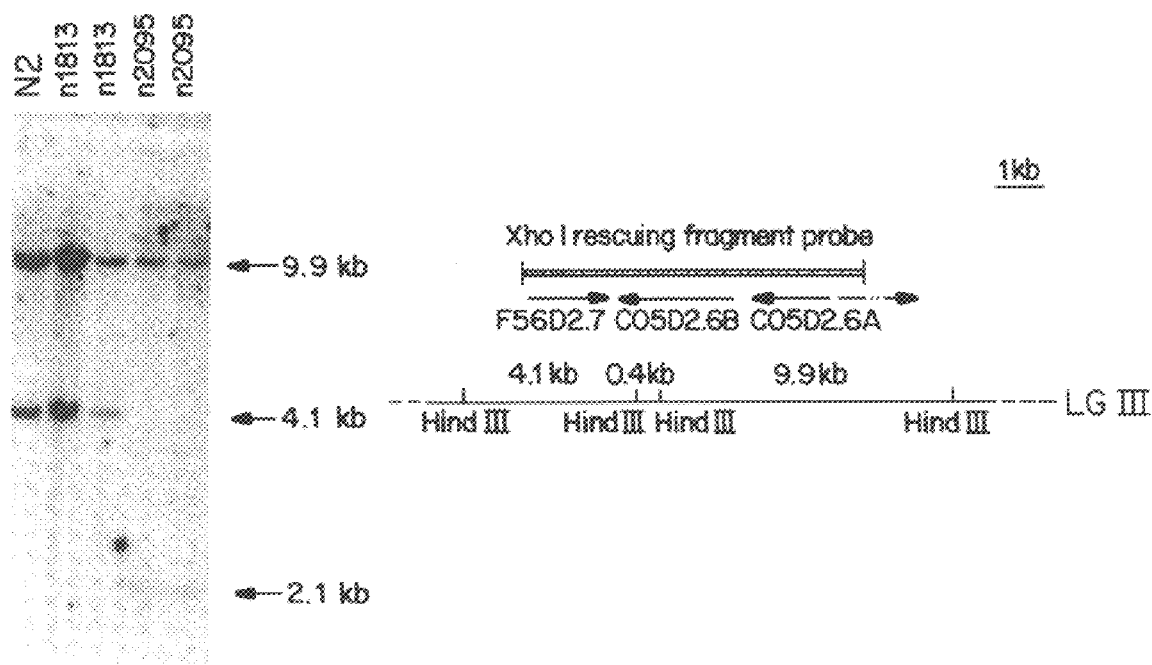

To determine which one of the three genes present on the Xho I fragment corresponds to ced-6, a number of constructs were generated containing internal deletions or point mutations. The present inventors found that the deletion of most of the C05D2.6A/B operon had no deleterious effect on ced-6 rescue, whereas the introduction of a frameshift mutation within exon 3 of F56D2.7 abolished the fragment's rescuing activity (FIG. 1E). To exclude the possibility that F56D2.7 might be a multicopy suppressor of ced-6, and to confirm suspicions that F56D2.7 might correspond to the ced-6 locus, the two known ced-6 alleles, n1813 and n2095 were analysed for any nucleotide changes within this region. Southern blot analysis revealed an allele-specific restriction fragment length polymorphism affecting F56D2.7 in ced-6 (n209) mutants (FIG. 2A). Based on the hybridization patterns observed in n2095, a single nucleotide deletion in exon 4 of F56D2.7 in ced-6(n1813) was also identified. This mutation should result in a reading frame shift and a truncated protein (FIG. 2B). Taken together, the genomic rescue and mutation data strongly suggested that F56D2.7 corresponded to ced-6.

Identification of Ced-6 Transcripts

To confirm the predicted intron/exon structure for ced-6, the present inventor screened a mixed-stage cDNA library and identified 10 clones corresponding the ced-6 gene, Several of these contained splice leader SL2 sequences at the 5' end, suggesting that ced-6 might also be a downstream gene in an operon. To test this hypothesis, RT-PCR was performed on mixed-stage RNA using both SL1 and S12 trans-splicing leaders as primers for the PCR step. Interestingly, sequence analysis of the PCR-amplified fragments revealed that both SL1 and SL2 trans-splicing leaders can be found at the 5' and of ced-6 transcripts (FIG. 2B, data not shown). It is suspected that the upstream gene in the ced-6 operon is the predicted gene F56D2.1. The presence of SL1-trans-spiced mRNA suggests that ced-6 might also be transcribed from a second downstream promoter, independently of the upstream gene. The existence of a downstream promoter could possibly explain why the Xho I fragment could rescue ced-6 mutants even though it does not contain the whole ced-6 operon.

Figure 3B:
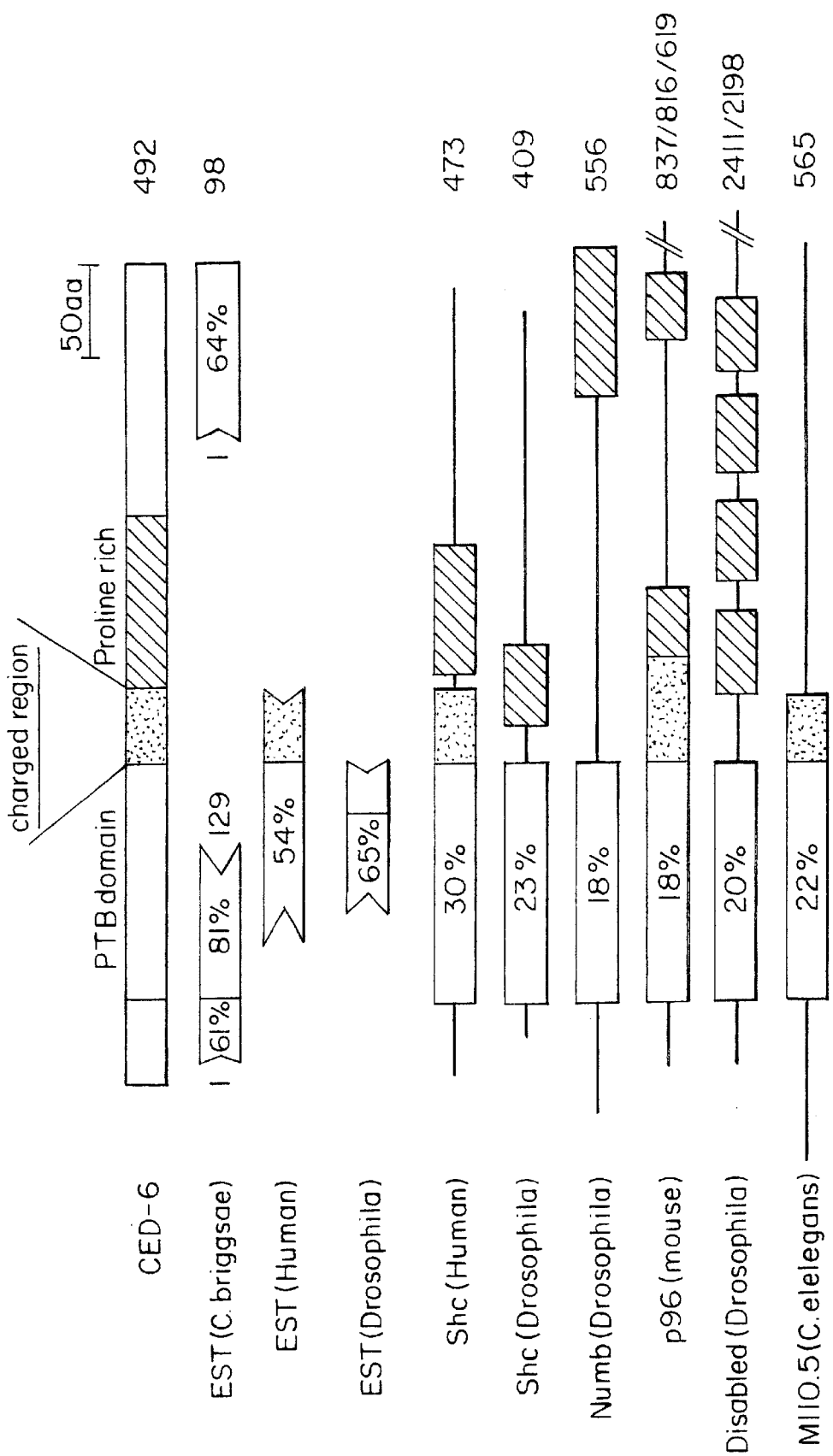

CED-6 Protein Contains a Phosphotyrosine Binding (PTB) Domain and a Proline/Serine Rich Region The full-length ced-6 cDNA is predicted to code for a 492 amino acid protein (FIG. 2B). A search of public sequence database with the predicted CED-6 sequence indicated that the N-terminal half of CED contains a putative phosphotyrosine binding (PTB) domain PTB domains can promote binding to phorphorylated tyrosine residues located within an appropriate primary sequence context The PTB domain is similar in function, but distinct in structure from the SH2 domain. The present inventors have aligned the CED-6 PTB domain with the PTB domains found in a number of other proteins (FIG. 3A). Secondary structure prediction programs suggest that most of these structural elements also exist in the CED-6 PTB domain. In addition to its similarity to known proteins, the inventors found that the CED-6 PTB domain also showed significant sequence similarity to the predicted translation products of a number of expressed sequence tags (ESTs: FIGS. 3A, B), In fact, the degree of similarity between CED-6 and a number of these ESTs was much higher than between CED-6 and any previously characterized protein (FIGS. 3A, 3B). Furthermore, in several cases, the sequence similarity between CED-6 and ESTs extended beyond the PTB domain (FIG. 3B). CED-6 also contains a proline/serine rich region at its C-terminal half, with 42% serine over a 24 amino acids stretch and clusters of proline-rich regions (FIG. 2B, FIG. 3B). These proline-rich regions were characterized by several sequence signatures of PxxP (FIG. 2A), which has been shown to promote interaction with SH3 domains (Ren et al., (1993); Yu et al. (1994) Cell 76 pp 933–945,; Grabs et al. (1997) J. Biol, Chem. 272 pp 13419–13425). Between the PTB and proline-rich regions is a short stretch rich in charged residues(41% charged amino acids over 46 amino acids). This highly charged region is also found in several other PTB domain containing proteins, including mouse p96, Shc, and *C. elegans* M110.5 (FIG. 3B).

Conservation of CED-6 Amongst Species

Figure 3C:
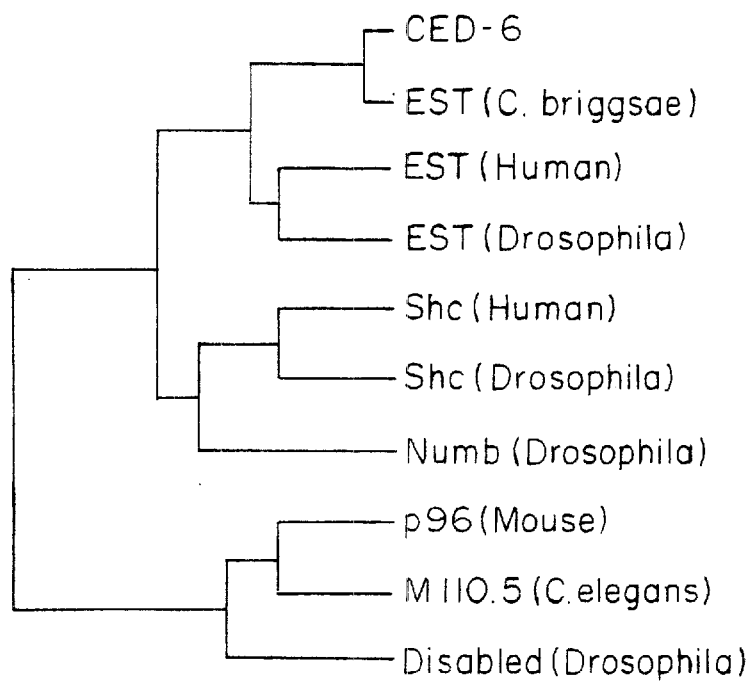

It was found that these EST clones also shared the homology region beyond the PTB domain with the CED-6 protein. A *C. Briggsae* EST clone has 72% identity to CED-6 over 132 amino acids at the N-terminus, and 64% identity to CED-6 over 103 amino acids at the C-terminus (FIG. 3B). Three overlapping human EST clones were also obtained and constructed into one sequence. The human EST fusion sequence showed −54% identity to PTB domain of CED-6, and also contains a highly charged region right after the PTB domain. The evolution tree based on the alignment of PTB domains showed that CED-6 formed a subgroup with EST clones from human, Drosophila, and *C. Briggsae*, suggesting that these proteins might be functionally conserved. Mouse p96, Drosophila Disabled, and *C. elegans* M110.5 formed another subgroup (FIG. 3C). The tree also indicated that the Shc subgroup is more similar than the p96 subgroup to CED-6 subgroup.

Ced6 Acts Cell-autonomously Within Engulfing Cells

The present inventors have performed genetic mosaic analysis to determine if ced-6 acts within engulfing cells or dying cells. For convenience, we concentrated on a pair of cells on adult gonad, germ cells and somatic sheath cells (FIG. 4). During oogenesis large number of oocytes undergo programmed cell death, and normally these dying cells are engulfed by somatic sheath cells (Hengartner, 1997). In this analysis a mosaic pattern of genetic background for ced-6 and wild type between germ cells and somatic sheath cells was generated. Ncl-1 mutant was used for the identification of the mosaic pattern in the single-cell resolution since in the Ncl-1 mutant somatic cells of animals exhibit abnormal enlarged nucleoli, which can be easily identified under Normaski optics (Herman, 1984; Genetics 108 pp 165–189; Hedgecock and Herman, 1995 Genetics 141 pp 989–1006). A strain was constructed dpy-17(e164) ced-6 (n1813) mec-14(u55) ncl-1(e1865) unc-36(e251)III; sDp3. This worm strain showed a wild type phenotype since the sDp3(III;f) duplication covers all these mutations (Roseabluth et al., (1985) Genetics 109 pp 493–511). To identify the animals with ced-6 mutant germ cells and wild-type somatic sheath cells, animals must be found with the duplication loss from any of P2, P3 and P4 lineages but not from EMS, MS or any lineages below the MS which would lead to the loss of the duplication in somatic sheath cells (FIG. 4). These animals can be obtained by looking through many animals of the constructed strain for the Pals laying only Dpy Unc progenies. The animals with the loss of the duplication in P1 lineage also lay only the Dpy Unc progenies, however these animals are not mosaic animals for the present purpose since the loss of the duplication in P1 lineage results in the ced-6 mutant background in both germ cells and somatic sheath cells. From 1,000 dpy-17(e164) ced-6(n1813)mec-14(u55) ncl-1(e1865) unc-36(e251)III; sDp3 animals, six animals were identified laying only Dpy Unc progenies. Observation of these six animals under Normaski optics indicated that one animal had the duplication lost in P4, one in P3, three in P2, and one in P1. All five animals displayed no cell corpses in gonad except the one with the duplication lost in P1, suggesting that ced-6 is not required in germline for engulfment. Since the chance for loss of the duplication in all cell divisions is approximately the same (Hedgecock and Herman, 1995), the rate of the sDp3 loss is 0.15% per cell division. Animals were then looked for with the ced-6 mutant somatic sheath cells and wild-type germ cells. From 500 animals four animals were identified with enlarged nucleoli in the somatic sheath cells in one arm of the gonad (FIG. 5B), and all four animals did not have the duplication lost in the lineage generating germ cells (FIG. 4). Three animals appeared to have the duplication lost in sheath cells in the anterior arm but not in the posterior arm. And the accumulated cell corpses were only observed within the anterior gonad arm, but not the posterior gonad am of these animals (FIG. 4, Table 1). One animal had the duplication lost in the sheath cells surrounding the posterior gonad arm, but not in that surrounding the anterior arm. This animal had cell corpses accumulated within the posterior arm but not the anterior arm (FIG. 4). These results suggest that ced-6 is required for somatic sheath cells, or engulfing cells to eliminate tie dying cells in adult gonad.

Ced-6 Promotes the Engulfment of Embryonic and Germ Cell Corpses

Figure 5C:
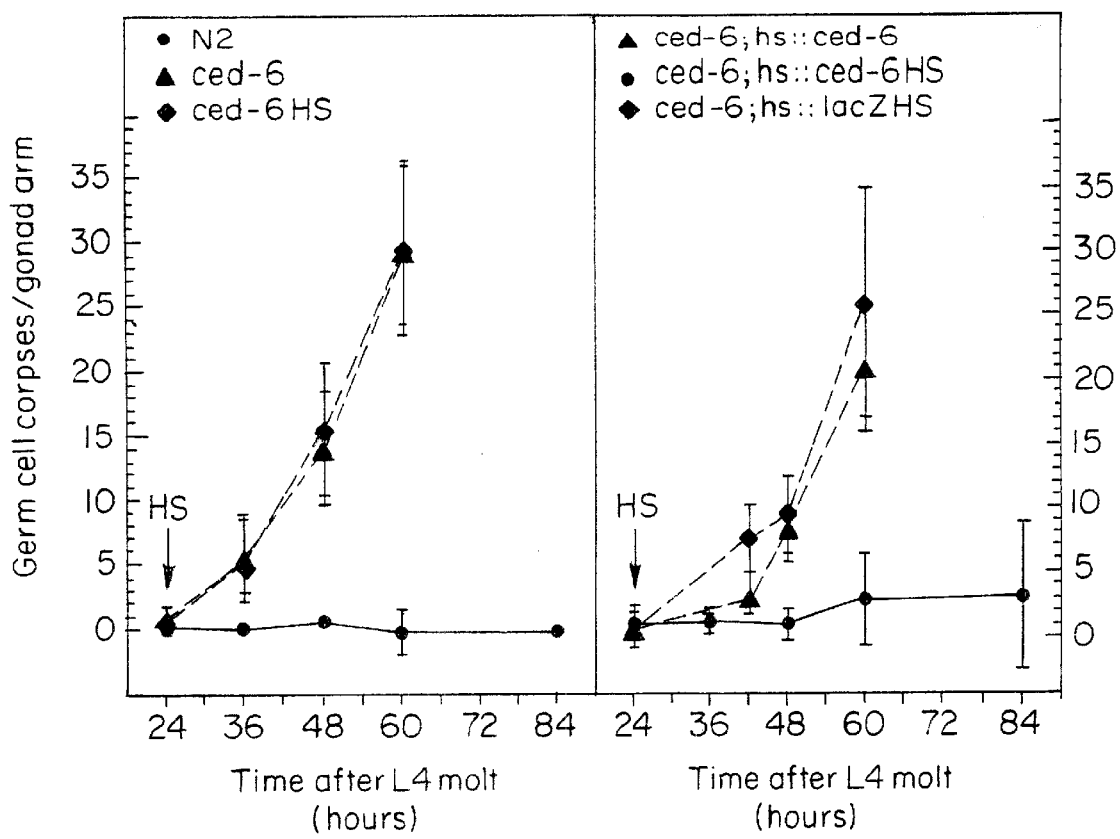

To unambiguously demonstrate that F56D2.7 cDNA indeed corresponds to ced-6, the inventors tested whether the full-length F56D2.7 cDNA can rescue the engulfment defect of ced-6 mutants, and transgenic animals were generated carrying the F56D2.7 cDNA under the control of the *C. elegans* heat shock promoters hsp-16.2 and hsp-16.48 (see Examples) Used together, these two promoters drive expression in almost all somatic cells, including both cells that normally undergo programmed cell death and cells that normally engulf the dying cells. To test for rescue, embryos laid by transgenic mothers were exposed to a brief heat shock pulse just prior to the appearance of the first developmental cell deaths, and scored the number of persistent corpses visible in the heat-shocked animals after hatching (FIG. 4A), As expected, over-expression of F56D2.7 cDNA significantly and specifically reduced the number of persistent cell corpses visible in ced-6 mutants, confirming that F56D2.7 is the relevant gene affected by the mutations that we detected in ced-6(n1813) and ced-6(n2095) mutants. Rescue of F56D2.7 cDNA in germline was also tested (FIG. 5C). Adult hermaphrodites were exposed to a brief heat shock pulse just prior to the appearance of the germline cell death, and scored the number of persistent cell corpses 12 hours and beyond after the heat shock. No cell corpses were found in gonads of the majority of animals, suggesting that ced-6 cDNA can also rescue the engulfment defect of ced-6 in germline.

Figure 5D:
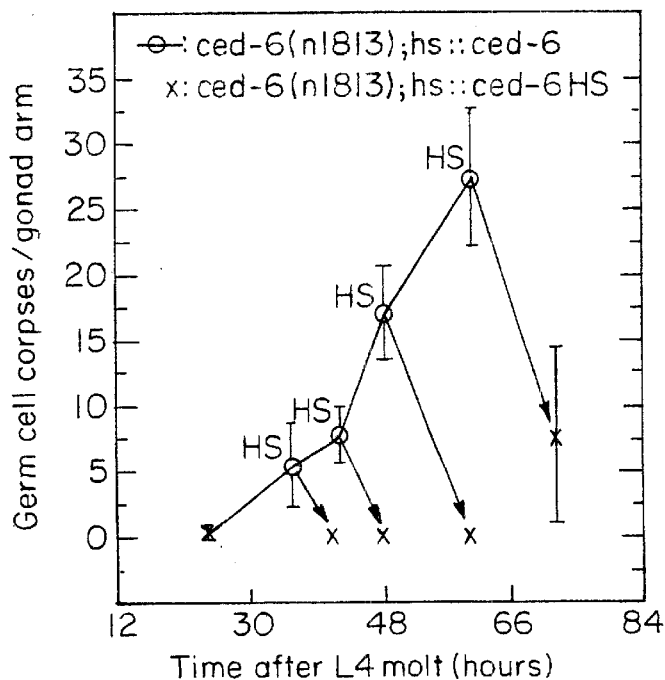

Recognition and engulfment of apoptotic cells is a very early event in *C. elegans*, programmed cell death (Robertson and Thomson, (1982)J. Embryol. Ex. Morph 67 pp 89–100). In ced-6 mutants, the extension of cytoplasm is blocked, resulting in the persistence of cell corpses (Ellis et al., 1991). These cell corpses, however disappeared from the animal eventually. To determine whether ced-6 acts only in a narrow time-window at the early stage of cell death or whether the signal transduction pathway can be used to engulf cell corpses formed many hours after cell death takes place, the present inventors tested whether F56D2.7 cDNA promotes the engulfment of persistent cell corpses. Ced-6 was over-expressed three hours before the embryos hatch, when most of cells dying by programmed cell death during the embryonic development have been dead approximately for five hours (FIG. 5A), and examined cell corpses three hours after the heat-shock on the head of L1 larvae. The number of cell corpses was found to be suppressed significantly (FIG. 5B). The control experiments with either no heat treatment, or over-expression of lacZ showed no obvious effect on the corpse expression, suggesting that over-expression of ced-6 can promote the engulfment of cell corpses in soma (FIG. 5B). The inventors also tested if over-expression of ced-6 could promote the engulfment of cell corpses formed hours after the cell death in the germline (FIG. 50). Adult transgenic animals carrying ced-6 cDNA driven by the heat shock promoters were heat structured at several time points after the accumulation of cell corpses in gonad and the number of cell corpses 12 hours after the heat shock were examined. It was found that cell corpses could be removed sufficiently at all time points suggesting that over-expression of ced-6 can promote the engulfment of cell corpses accumulated in germline for hours, even days (FIG. 5D). The present inventors have concluded that the signal transduction pathway in which ced-6 is involved can carry on the task of removing cell corpses, and there is no specific time-window for ced-6 to act during the process of programmed cell death.

Mosaic CED-6 Protein Expression Supports That Ced-6 Acts Within Engulfing Cells

The inventors have developed a simple way to detect quickly if ced-6 acts within engulfing cells. This method is based on dying cell's filing to express proteins so as to generate a mosaic pattern of protein expression. However, this idea can be only applied to the soma, but might not to the germline, since in germline all germ cells share one syncytial cytoplasm (Hirsh et al., (1976) Developmental Biology 49 pp 200–210), so those germ cells carrying the transgenes could contribute the expressed proteins into the cytoplasm, subsequently all newly formed oocytes. However the mosaic pattern of the protein expression can be generated in the germline because the transgenes have been found not. to be expressed well in germ cells. The expression pattern of heat shock promoters in gonad were examined (data not shown). Adult animals carrying the lacZ transgenes driven by heat shock promoter were applied heat shock 24 hours after L4 molts. The lacZ expression by beta-gal staining in both germ calls and sheath cells was subsquently examined. It was found that somatic sheath calls were stained blue and the stain could last 60 hours after the heat shock, but not the germline at any time point after the heat shock, the similar result was also observed in previous studies (Stringham et al., (1992) Molecular Biology of the cell 3 221–233). The expression of ced-6 in germline upon heat shock was also examined for three-fold embryos laid by heat-treated transgenic animals for the rescuing activity of the engulfment defect. It was found that the majority of embryos had the ced-6 mutant phenotype, suggesting that ced-6 is not expressed well in germline (Data not shown). That ced-6 transgene in gonad is not expressed very well provided a useful tool to test if ced-6 acts within the somatic sheath cells. As described in FIG. 4C, cell corpses were not observed in majority of animals in gonad at the different time point after the heat treatment, and the phenomenon lasted until 60 hours or beyond after the heat treatment (5C). In contrast to this result, without the heat treatment these transgenic animals had cell corpses accumulated in gonad, similar to that of the ced-6(n1813) mutant. Over-expression of lacZ didn't affect the expression of cell corpses of ced-6 mutant, either (5C). These results support the conclusion from the mosaic analysis that ced-6 might act within engulfing, cells, the somatic sheath cells. This method provides a simple way to detect if a gene acts within engulfing cells or dying calls.

Site of Active of Ced-6 in Relation to Ced-1 and Ced-7

To understand if ced-6 genetically interacts with any other engulfment genes, the present inventors over-expressed ced-6 at the genetic background of ced-1, 7, 2, 5, and 10. The extra-chromosomal arrays carrying ced-6 cDNA driven by heat shock promoters were transferred from ced-6(n1813) background to wild-type N2 background, and subsequently to ced-1, 7, 2, 5, and 10 mutant background, ced-6 was then over-exposed by following the method used for the rescue of ced-6 engulfment defect by the over-expression of ced-6 cDNA as described in FIG. 5A. It was found that over-expression of ced-6 could partially suppress the engulfment defect for ced-7(n1997). To understand if the suppression is allele-specific, two additional alleles, ced-7(n1996) and ced-7(n1892), were tested and similar results were achieved, suggesting that the suppression is not allele-specific (FIG. 6A). For the same purpose three alleles of ced-1, n1506. n1995. and n1735, were also tested it was found that over-expression of ced-6 could partially suppress the engulfment defect of three alleles of ced-1 (FIG. 6A). Several control experiments were performed to confirm that these rescue were specific for ced-6. Transgenic animals with ced-6 transgene without heat treatment were tested; over-expression of lacz at ced-1 or ced-7 engulfment mutant background was also tested. Results showed that the similar numbers of cell corpses were achieved as that of the ced-1 or ced-7 mutants. Heat treatment reduced the expression of cell corpses for ced-7(n1997). Over-expression of ced-6 reduced the expression of cell corpses even more. These data suggest that the partial suppression of the engulfment defect of both ced-1 and ced-7 are specific for ced-6. It was also observed that over-expression of ced-6 did not have obvious effect on the number of cell corpses for ced-2, 5 and 10 (data not shown) These results suggested that ced-6 might act downstream of both ced-1 and ced-7, and ced-2, 5 and 10 act either downstream of ced-1, 6, and 7 or in a different pathway (FIG. 6B).

The Regulation of the Ced-6 Expression

SL2 was detected at the 5' end of the ced-6 cDNA, suggesting that ced-6 is a downstream gene of an operon (Huang and Hirsh (1989); Proc. Natl. Acad. Sci. USA 86 pp 8640–8644: Spieth et al. (1993) Cell 73 pp 521–532; Zorio et al. (1994) Nature 372 pp 270–272; Blumenthal et al. (1995) TIG II pp 132–136). The inventors have shown previously that a 10 kb Xho I fragment can rescue the engulfment defect of the ced-6 mutant. The fragment, however contains only ced-6, the downstream gene of an operon, but not the upstream one. The expression of ced-6 might rely on the 1 kb upstream region of ced-6 gene, a intergenic region of the operon. The Intergenic region of a operon sometimes could be used as a promoter for the expression of the downstream gene (Blementhal and Steward, (1997 C.elegans II) (Cold Spring Harbor; Cold Spring Harbor Laboratory Press pp 117–145).

CED-6 is an Adaptor Molecule Acting in the Signal Transduction Pathway of the Engulfment Protein phosphorylation is a well-defined "switch" mechanism for cells to deliver signals from one protein to another, and it is essential to transduce extracellular signals inside cells. PTB domain is another domain besides the SH2 domain to be able to interact with a phosphorylated tyrosine residue (Kavanaugh and Williams, (1994) Science 266; Blaikie et al., (1994) J.Biol.Chem 269 32031–32034). Several proteins containing PTB domains have been found to act as adaptor molecules in the signal transduction pathway. These include Shc, Sck, Numb, FE65, disabled, DOC-2, P96 and IRS-1 (Bork and Margolis, (1995) Cell 80 pp 693–694); Geer and Pawson, (1995) TIBS 20 pp 277–280). The proline rich region from many proteins have been shown to form multiproline helix and interact with a SH3 domain (Ren et al., 1993; Gout et al., (1993) Cell 75 pp 25–46, Yu et al., 1994). Both biological analysis and analysis of the crystal structure of the SH3 binding domain suggested that the sequence signature, PxxP, was essential for its interaction with the SH3 domain (Ren et al., 1993; Yu et al., 1994; Grabs et al., 1997). As we have shown previously, CED-6 contained stretches of proline rich regions containing the PxxP signature, suggesting its potential to interact with the SH3 domain. It is believed by the inventor that CED-6 is an adaptor molecule directly or indirectly transducing the signal from receptors to effectors or cytoskeleton molecules to initiate the engulfment process.

The Interaction Partners of CED-6

The PTB domain has been shown to interact specifically with a NPXY(p) motif (Kavanaugh and Williams, 1994; Zhou et al., (1995) Nature 378 pp 584–592: Geer and Pawson. 1995). Many receptors such as EGF receptor, TrkA, insulin receptor, IGF-1 receptor contain this motif at the carboxyl terminal (Geer and Pawson, 1995). Signals from these receptors have been shown to be transduced through the interaction of a phosphotyrosine residue of this motif with PTB domains of adaptor molecules, such as Shc and insulin receptor substrate 1. The inventors found that in the intracellular region of CED-7 there was a NPXY(p) motif. Ced-7 has been suggested to act in the same genetic pathway with ced-6 (Ellis et al., 1991). The inventors have shown that ced-7 might act upstream of ced-6 (FIG. 7). Ced-7 encodes a ABC transporter, and its mammalian homologue, ABC1 was found to be required for the macrophage to engulf dying cells (Luciani and Chimini, 1996), suggesting that ced-7 might act within engulfing cells. It is possible for CED-6 to physically interact with CED-7 through a PTB domain with NPXY(p) motif of CED-7 to regulate the signal transduction of engulfment process.

CED-6 also contains a proline/serine rich region with several sequence signature PxxP, which might mediate its interaction with the SH3 domain. The SH3 domain has been suggested to mediate protein-protein interactions between signaling molecules downstream of membrane-bound receptors (Koch et al., (1991) Science 252 pp 252–673; Pawson and Schlessinger, (1993) Current Biology 3 pp 434–442. A SH3 domain containing protein is likely to interact with CED-6 and to regulate the signal transduction pathway of engulfment. Several proteins might directly or indirectly interact with CED-6 protein. The present inventors have shown that ced-1 might act upstream of ced-6(FIGS. 6 & 7A). The relationship between ced-1 and ced-6 will depend on the cloning of the gene. A protein with a phosphorylated tyrosine residue should exist to interact with the PTB domain of CED-6. This phosphorylated protein is either a tyrosine kinase or a substrate of a tyrosine kinase, and a tyrosine phosphatase should also be involved in the signal transduction pathway of engulfment to down-regulate the activity of the phosphorylated proteins. Some studies on phagocytosis in mammalian system have shown that a tyrosine kinase signal transduction pathway might play an essential role in the opsonin-mediated phagocytosis process (Roshenshine and Finlay, (1993) BioEssays 15 pp 17–24; Greenberg, (1995) Trends in Cell Biology 5 pp 93–99. The present results suggest that it might be the same case for the PCD triggered engulfment. These two types of phagocytosis might share some similarity at the end.

CED-6 Acts Within Engulfing Cells

A genetic mosaic analysis has been performed to determine that ced-6 acts within engulfing cells. This conclusion was drawn based on the observation of a pair of cells, germ cells and somatic sheath cells. We have shown previously that over-expression of ced-6 can promote the engulfment of cell corpses. Since cells that have been dead for many hours are very unlikely to maintain their ability for protein expression (Estus, 1994; Freeman, 1994), the rescue of cell corpses is most likely to be due to the expression of ced-6 within the engulfing cells. This result suggests that ced-6 also acts within the engulfing cells in the soma. Previously it has been shown by the inventors that over-expression of ced-6 could rescue the engulfment defect of ced-6 in both soma and germline (FIG. 5), suggesting that ced-6 acts in a similar mechanism in both places.

CED-6 Can Promote the Engulfment of Cell Corpses

The present inventors have shown that over-expression of ced-6 promotes the engulfment of dying cells at a very early stage of the cell death, and cell corpses formed hours after the cell death. Cell corpses have been shown to have a typical morphology of apoptotic cells, for instance, membrane blebing. The antigens presented on the membrane surface of cell corpses for their recognition by engulfing cells might be somewhat different from that on the membrane surface of the early dying cells. Irrespective of ligands on dying cells and receptors on the engulfing cells are the same or not in both situations, ced-6 is required for the engulfment. A few call corpses in the gonad were not removed upon heat shock for some animals later after the heat shock. These corpses tend to be located in between oocytes and closed to the spermatheca. The failure of the engulfment of these cell corpses might be due to their lack of contact with the sheath cells. It is concluded that cell corpses, just like dying cells at the early stage of the PCD, can trigger phagocytosis. In mec-4 mutant animals six touch sensory neurons die of necrotic death due to a channel defect leading to an impaired osmotic pressure in these cells (Driscoll and Chalfie, (1991) Nature 349 pp 588–593). Chung and Driscoll showed that the removal of the swelling dead cells was delayed significantly at the ced-6 background, implying that ced-6 is also Involved in the removal of necrotic dying cells. Thus, there might be similar signals presented on the surface of dead cells to allow them to be recognized by engulfing cells regardless the manner of the death; and the signal transduction pathway in which ced-6 is involved can be used to respond to these signals to cause engulfment. The fact that engulfment is triggered 50 early and is completed so swiftly is a clever design of nature, it is important especially for tissues with massive cell death.

Conservation of the Engulfment Program

The present inventors have shown previously in the alignment that an EST clone from *C. Briggsae* is highly conserved with CED-6 in both the N- and C-terminal region, suggesting that this EST clone might represent a real CED-6 homologue (FIG. 38). EST clones for Drosophila and human are also highly conserved to CED-6 but mainly in the region of PTB domain (FIGS. 3A & 3B). This result 5suggested the possibility for these PTB domain proteins to be functional homologues of CED-6 in those specimens. As a result the present inventors have cloned and characterized two human homologues of *C.elegans* ced-6 gene.

Expression Vectors and Transfected Mammalian Cells Expressing CED-6

The present inventors inserted fragments of *C.elegans* ced-6 DNA into commercially available vectors, including vectors having the reporter gene, green fluorescent protein (GFP), are set out in table 1 below;

The transfected MCF7 cells as above are useful for conducting assays to identify compounds which inhibit and enhance CED-6 or ced-6 as will be discussed hereafter.

Human Homologues of *C. Elegans* CED-6

In accordance with the invention there is provided an isolated protein which is an adaptor molecule in a signal transduction pathway which regulates phagocytosis of apoptotic cells.

In accordance with another embodiment of the invention there is provided an isolated protein which is a human homologue of *C.elegans* CED-6 which comprises an amino acid sequence as shown in FIG. 20 (SEQ ID NO: 10) or an amino acid sequence which differs from that shown in FIG. 20 only in conservative amino acid changes (h1CED-6).

Also provided is a nucleic acid (DNA RNA, cDNA or genomic DNA) encoding h1CED-6 (SEQ ID NO: 9) or a functional equivalent thereof, for example a nucleic acid comprising the sequence of nucleotides from about nucleotide position 430 to about nucleotide position 1344 shown in FIG. 19 or the entire sequence of nucleotides shown in FIG. 18 (SEQ ID NO: 9).

The invention also provides a protein which is a fragment of the protein with the amino acid sequence shown in FIG. 20 (SEQ ID NO: 10). The fragment may comprise a sequence of amino acids corresponding to the phosphotyrosine binding domain of FIG. 20 (SEQ ID NO: 12) which is from about amino acid 11 to 190 in FIG. 20. A nucleic acid encoding said fragment is also provided (SEQ ID NO: 11). The invention includes the nucleic acid (SEQ ID NO: 13) and amino acid (SEQ ID NO.: 14) of the proline/serine rich region of human CED-6 (h1and 112 CED-6). Also, the

TABLE 1

GFP-CED-6 expression in MCF7
Cloning of CED-6 fragments in pEGFP

| | from . . . (bp) - to . . . (bp) | | | | | | |
|---|---|---|---|---|---|---|---|
| Vector | 2–1581 | 22–1494 | 598–1581 | 598–1494 | 22–745 | 744–1581 | 744–1494 |
| TA-PCR | pGA1 | pGA2 | pGA3 | pGA4 | pGA5 | pGA6 | pGA7 |
| pAS2 | pGA1011 | | pGA1013 | | | | |
| pGAD42+ | | | | | | | |
| pEGFP-C1(*) | pGA3011 | | pGA3013 | | pGA3015 | | |
| pEGFP-C3(*) | | | | | | pGA3036 | |
| pEGFP-N2(*) | | | | | pGA3045 | | |
| pEGFP-N3(*) | | pGA3062 | | pGA3064 | | | pGA3067 |

(*)are commercially available from Clontech

Visualization GFP Fluorescence in MCF7 Cells

Human breast cancer cells, MCF7 (ATCC: HTB-22), were seeded in Lab Tek chambered coverglass (Nalge Nunc Intentional) and transfected using lipofectAMINE (GibcoBRL). After 18 hours, the chambered coverglasses where placed on a inverted microscope, and GFP fluorescence could be visualized.

Expression of GFP-CED-6

Subcellular localization of worm CED-6 was assayed using GFP fusion proteins. By using different fragments the inventors showed that CED-6 has a clear cytoplasmic localization, This localization was abolished when only the PTB of CED-6 was used indicating that the C-terminal part might be implicated in proper targeting. Since the actual expression level varies from cell to cell one can observe an apoptotic phenotype in highly expressing cells and an elevated level of phagocytosis in strong expressing cells. In addition localization to the lamelli was observed in some cells which perform engulfment.

invention includes the nucleic acid (SEQ ID NO.: 15) and the amino acid (SEQ ID NO.: 16) of the highly charged region of human CED-6 (h1and h2 CED-6).

There is also identified herein a splice variant of h1CED-6 (referred to herein as h2CED-6) which variant comprises an amino acid sequence as shown in FIG. 21 (SEQ ID NO: 18) or an amino acid sequence which differs from that shown in FIG. 21 only in conservative amino acid changes. Also provided is a nucleic acid (DNA, RNA, cDNA or genomic DNA) encoding h2CED-6 (SEQ ID NO: 17) or a functional equivalent thereof, for example a nucleic acid comprising from about nucleotide position 430 to about nucleotide position 1206 in FIG. 19 or the entire nucleotide sequence shown in FIG. 19. (SEQ ID NO: 17).

The invention also provides a fusion protein in which one part of the fusion is a protein having an amino acid sequence as shown in any of SEQ ID NOS: 10, 12, 14, 16 or 18 or a sequence differing from acid sequences only In conservative amino acid changes. The protein may be fused with for example, an epitope tag or expression product of a reporter gene.

In particular, biologically active derivatives or analogs of the above described proteins, including fragments and functional domains from CED-6 as well as h1CED-6 and h2CED-6, referred to herein as peptide mimetics can be designed and produced by techniques known to those of skill in the art (see e.g. U.S. Pat. Nos. 4,612,132; 5,643,873 and 5,654,276, the teachings of which are incorporated herein by reference). These mimetics can be based, for example, on a specific CED-6, h1or h2 CED-6 amino acid sequence and maintain the relative position in space of the corresponding amino acid sequence. These peptide mimetics possess biological activity similar to the biological activity of the corresponding peptide compound, but possess a "biological advantage" over the corresponding CED-6 amino acid sequence with respect to one, or more, of the following properties: solubility, stability and susceptibility to hydrolysis and proteolysis.

Methods for preparing peptide mimetics include modifying the N-terminal amino group, the C terminal carboxyl group, and/or changing one or more of the amino linkages in the peptide to a non-amino linkage. Two or more such modifications can be coupled in one peptide mimetic molecule. Modifications of peptides to produce peptide mimetics are described in U.S. Pat. Nos. 5,643,873 and 5,654,276, the teachings of which are incorporated herein by reference. Other forms of the h1 or h2 CED-6 proteins, encompassed by the claimed invention, include those which are "functionally equivalent." This term, as used herein, refers to any nucleic acid sequence and its encoded amino acid which mimics the biological activity of the h1 or h2 CED-6 proteins and/or functional domains thereof. Biologically active is used to describe a protein capable of regulating the phagocytosis of apoptotic cells.

A polypeptide can be in the form of a conjugate or a fusion protein which can be manufactured by known methods, Fusion proteins can be manufactured according to known methods of recombinant DNA technology. For example fusion proteins can be expressed from a nucleic acid molecule comprising sequences which code for a biologically active portion of the protein and its fusion partner, for example a portion of an immunoglobulin molecule. For example, some embodiments can be produced by the intersection of a nucleic acid encoding immunoglobulin sequences into a suitable expression vector, phage vector, or other commercially available vectors. The resulting construct can be introduced into a suitable host cell for expression. Upon expression, the fusion proteins can be isolated or purified from a cell by means of affinity matrix.

Expression vectors incorporating any of the above mentioned nucleic acids including those designated SEQ ID NOS: 9, 11, 13, 15 or 17, optionally with a reporter gene as a foresaid, are also provided by the invention.

Cloning of h1CED-6 and h2CED-6

Following the cloning of the *C. elegans* ced-6 gene and the full sequencing of the open reading frame the present inventors undertook extensive searches against public domain human databases. These revealed statistically significant homologues to a number of ESTs at the carboxy terminal region of the protein and one EST showed homology to the carboxy terminal of the PTB domain and at the beginning of the charged region. These ESTs were used for construction of primers for 5' RACE using a Marathon-ready cDNA colorectal adenocarinoma library from Clontech. Subsequent additional sequence analysis and rounds of database searching revealed additional ESTs which enabled construction of a concensus sequence of approximately 2400 bp for h1ced-6 (FIG. 6). Further sequence analysis has revealed a splice variant of the sequence shown in FIG. 18 (h2CED-6), the portion which is alternatively spliced being underlined. The DNA of h2CEd-6 is shown in FIG. 19 and the amino acid sequence in FIG. 21. The amino acid sequence of h2CEd6 is consistent with it being a dominant negative version of h1CED-6 which antagonizes active of h1CED-6.

Assays for the Identification of Inhibitors and Enhancers of CED-6 h1CED-6 and h2CED-6

The cloning and functional Characterization of *C.elegans* CED-6 and its two human homologues have permitted assay methods to the developed which allow identification of compounds which might inhibit or enhance CED-6, h1CED-6 or h2CED-6 activity or inhibit or enhance the transcription of these proteins. These may involve detection of the level of phagocytosis of apoptotic particles, measurement of level of actin-cytoskeleton rearrangement or detection of the level of transcription of the CED-6 proteins via a reporter gene such as GFP.

An assay for the identification of inhibitors and/or enhancers of phagocytosis may consist of a cell line stably or transiently transfected with ced-6, h1ced-6 or h2ced-6 or any other member of the CED-6 signal transduction pathway. Cell lines may also be microinjected with purified protein or vectors expressing antisense RNA. The expression product may be a fusion protein with GAP. Non transfected cells can be used in the assay too. The cell line may be a fibroblast cell line such as COSI, BHK 21, L929, CV1, Swiss 3T3, HT144, IMR32 or another fibroblast cell line. The cell line may also be an epithelial cell line such as HEPG2, MDCK, MCF7, 293, Hela, A549, SW48, G361, or any other epithelial cell, line. The cell line may a primary line, such as human dermal FIBs, dermal keratinocytes, leucocytes, monocytes, macrophages, or any other primary cell line. Cells may be double transfected with other genes (like lectin, CD14, SRA, CD36 ABC1, ced-5, DOCK180...) being from vertebrate (human fish, mouse, ...) or invertebrate origin (*C.elegans*).

Phagocytosis assays consist of the addition of and uptake of particles and/or apoptotic cells, by these cell lines. The particle may be opsonized heat or chemically killed bacteria and yeast in a variety of sizes, shapes and natural antigenicities. The particle or cell may be an opsonized, fluorescently labeled, heat or chemically killed bacteria and yeast in a variety of sizes, shapes and natural antigenicities. The cell may be a apoptotic neutrophils, apoptotic lymphocytes, apoptotic erythrocytes or any other apototic cell. These apoptotic cells may be opsonized and/or labeled with dyes or fluorescent dyes. The killed bacteria or yeast cells and the apoptotic cells are referred to as herein apoptotic particles.

Assay 1

Cells, transfected with ced-6 or any other gene described herein, for example, nucleic acids of SEQ ID NOS: 1, 3, 5, 7, 9, 11, 13, 15 or 17, can be grown in monolayer or in suspension. The apoptotic particles are added to the transfected cell. Phagocytosis can be followed by the uptake rate of the apoptotic particles. This can be measured by microscopy, by fluorescence microscopy, by quantitative spectrofluorometry and by flow cytometry. Cells and or particles may additionally be labeled with dyes, fluorescent dyes, antibodies and dyes of fluorescent dyes linked to antibodies prior to detection and measurement. Decrease or increase of the uptake of the apoptotic particles is a measurement for the influence of the transfected gene or genes in the phagocytosis.

Assay 2

Compounds can be added to assay 1 to test their influence on the genes that are involved in the phagocytosis pathway. Transiently or stably transfected cells are grown in suspension or in monolayer. A series of compounds is added to the cells prior to the addition of the apoptotic particles. The influence of the compounds can be measured by comparing the uptake rate of the apoptotic particles with and without the addition of the compound. Measurements are described in Assay 1.

Assay 3

Cells are able to phagocytose apoptotic particles by engulfment of particles. This involves the reorganization of the actin cytoskeleton. Mammalian cells, may be transiently or stably transfected with CED-6 or any gene involved in the CED-6 phagocytosis signal transduction pathway, for example, with a nucleic acid have the sequence of nucleotides shown in any one of SEQ ID NOS: 1, 3, 5, 7, 9, 11, 13, 15 or 17 Cells can be any cell as described in Assay 1. The genes may be expressed as a GPF fusion product. Cells may be double transfected (see Assay 1). The reorganization of the actin cytoskeleton can be visualized with fluorescent dyes linked to phalloidine, which interacts with F-actin. Reorganization of the cytoskeleton is an measurement for the engulfment induction by the transfected gene or genes. Transfected cells may be treated with particles or apoptotic calls as described in Assay 1. Reorganization of the cytoskeleton is visualized by microscopy or fluorescence microscopy.

Assay 4

Compounds can be added to Assay 3 to test their influence on the genes, that are involved in the cytoskeleton reorganization related to the phagocytosis pathway and engulfment. These compounds may enhance or inhibit the engulfment or cytoskeleton reorganization induced by the introduced genes. Transiently or stably transfected cells are grown in suspension or in monolayer. A series of compounds is added to the cells. The influence of the compounds can be measured by comparing the reorganization of actin cytoskeleton with and without the addition of the compound. Measurements as are described in Assay 1, Assay 2 and Assay 3. Apoptotic particles may be added in this test to induce phagocytosis, as described in Assay 2.

Assay 5

Non-transfected or transfected cell-lines such as those described above may be microinjected with purified CED-6 protein, for example, a protein having the amino acid sequence as shown in SEQ ID NOS: 2, 4, 6, 8, 10, 12, 14, 16 or 18 or any protein from the ced-6 pathway or a fusion protein comprising any of said proteins. Microinjection can be done on the primary cell lines or the fibroblast cell lines or the other epithelial cells lines. The cell lines can be transfected with another gene prior to microinjections. Assays 1 through Assay 4 can be performed on these microinjected cells.

Assay 6

Transfected or non-transfected cell-lines as described above may be microinjected with a vector expressing CED-6 antisense RNA including antisense RNA in respect of any of the aforementioned proteins or any antisense RNA for genes involved in the ced-6 pathway. Microinjection can be done on the primary cell lines or the fibroblast cell lines or the epithelial cell lines. The cell lines can be transfected with another gene prior to microinjection. Assays 1 through Assay 5 can be performed on these microinjected cells.

Assay 7

Cell lines, as described in Assay 6 may be micro-injected with a vector expressing CED-6 antisense RNA or any antisense RNA for genes involved in the ced-6 pathway. Microinjection can be done on the macrophages. Inhibitory effects of the antisense RNA by inhibition of the CED-6 gene or genes involved in the CED-6 pathway can be followed and detected as described in Assay 1 through Assay 6. Compounds can be isolated which rescue the negative phenotype.

Phagocytosis Assays to Screen for Ced-6 Inhibitor/enhancers In *C.elegans*

The *C.elegans* ced-6 gene promotes the engulfment of dying embryonic and germ cells and persistent cell corpses. *C.elegans* may be used for detection and isolation of compounds that have an enhancing or inhibitory influence on phagocytosis and engulfment. In particular mutant worms lacking CED-6 activity or with otherwise altered CED-6 activity may be used or alternatively a transgenic worm transfected or transferred with CED-6, h1CED-6 or h2CED-6 DNA may be used.

Assay 8

A series of compounds may be applied on ced-6 mutant worms or on worms harboring mutations in the ced-6 pathway. Restoration of engulfment induced by the compounds can be visualized using Nomarski microscopy by counting cell corpses remaining in the head region of L1 larvae and in the gonads of the worms.

Assay 9

A series of compounds may be applied an humanized ced-6 mutant worms. Humanized worms are worms expressing the human ced-6 gene and are mutated for the *C.elegans* gene Human ced-6 rescues the mutant phenotype. Compounds inhibiting or enhancing the ced-6 phenotype can be selected by visualization of the engulfment phenotype using Nomarski microscopy and looking for cell corpses as aforesaid.

Medical Applications

The process of apoptosis has been implicated in the etiology—or associated with the pathology—of a wide range of diseases, including cancer, autoimmune diseases, various neurodegenerative diseases such as Amyotrophic Lateral Sclerosis, Huntington's Disease, and Alzheimer's Disease, stroke, myocardial heart infarct, and AIDS (Thompson, 1995). Thus a better understanding of the molecular events that underlie apoptosis might lead to novel therapeutic interventions. While much of the current attention is centered on the genes and proteins that control the killing step of the death process, it is very likely that the removal of apoptotic cells will prove to also be crucial for the proper overall functioning of the apoptotic program, and will offer another entry point for therapeutic intervention (see below).

The process of recognition and engulfment of dying cells is extremely swift and efficient. In animals, it is essentially impossible to find a cell with apoptoic features that is not already within another cell. Such rapid recognition and phagocytosis of apoptotic cells is an crucial aspect of programmed cell death in vivo: unengulfed apoptotic bodies can undergo secondary necrosis, leading to inflammation. Failure to remove apoptotic bodies also exposes the body to novel epitopes (from e.g., caspase-generated protein fragments), possibly encouraging the development of autoimmune disease. Persistent apoptotic bodies can often be observed following chemotherapeutic intervention (which leads to extensive apoptosis) and are particularly abundant in solid tumors, in which clearance of cell corpses might be delayed.

It is likely that failure to properly dispose of apoptoic cells leads to human disease. Genes involved in phagocytosis could therefore correspond to currently uncloned human inherited disease genes. Restoring proper phagocytosis would be a valid therapy for certain types of inflammation and autoimmune diseases.

Conversely, In some cases, cells that should be maintained are inappropriately recognized by the engulfment machinery and cleared from the body. Preventing the engulfment of such cells could be of great therapeutic value Examples of such diseases might include neurodegenerative diseases and stroke, as well as sickle cell aenemia.

In addition activation of engulfment could be used for the same cases for which it is proposed to use activation of apoptosis, e.g., cancer, Indeed, specific activation within the cancer cells of the pro-engulfing signal would lead to the cells+ removal—(and death)—without needing to activate the rest of the apoptotic machinery, This could be particularly useful for highly resistant tumors in which crucial elements of the central apoptotic machinery have already been inactivated.

Thus, in accordance with another of its aspects the invention provides a method of treating, for example inflammation, autoimmune disease and cancer by administering to a patient an effective amount of a substance which enhances phagocytosis of apoptoic cells, in particular a substance which enhances the activity of h1-CED-6 or the signal transduction pathway in which it participates. Such substances includes h1-CED 6 itself, a nucleic acid encoding h1-CED-6, an anti-sense nucleic acid to h2ced 6 or compounds identified in any of the aforementioned assays as enhancers of CED-6 or h1-CED-6 or of transcription of ced-6 or h1ced-6.

In addition the invention also enables a method of treatment of, for example, neurodegenerative diseases, stroke and sickle-cell anaemia by administering to a patient an effective amount of a substance which inhibits phagocytosis of apoptotic cells, in particular a substance which inhibits the activity of h1-CED-6 or the signal transduction pathway in which it participates. Such substances include h2 CED-6, a nucleic acid encoding h2CED-6 an anti-sense nucleic acid to h1ced-6 or compounds identified in any of the aforementioned assays as inhibitors of CED-6 or h1CED-6 or of transcription of ced-6 or h1 ced-6.

Pharmaceutical compositions comprising any of the above-mentioned therapeutic substances and a pharmaceutically acceptable carrier are also envisaged by the invention.

To accomplish the various therapeutic treatments as described herein, a nucleic acid which encodes h1 or h2 CED-6 or a functional portion or domain thereof must be introduced into a mammalian cell (e.g., mammalian somatic cell, mammalian germ line cell (sperm and egg cells)). This can be accomplished by inserting the isolated nucleic acid that encodes either the full length protein, or the domains described herein, or a functional equivalent thereof, into a nucleic acid vector, e.g., a DNA vector such as a plasmid, virus or other suitable replicon (e.g., a viral vector), which can be present in a single copy or multiple copies. The nucleic acid may be transfected or transformed into cells using suitable methods known in the art such as electroporation, microinjection, infection, and lipoinfection and direct uptake. Such methods are described in more detail, for example, in Sambrook et al., "Molecular Cloning. A Laboratory Manual, " 2nd ED. (1989), Ausubel, F. M., et al., Current Protocols in Molecular Biology, (Current Protocol, 1994) and Sambrook et al., "Molecular Cloning: A Laboratory Manual, " 2nd ED. (1989).

h1 or h2 CED-6 can be delivered to a cell by the use of viral vectors comprising one or more nucleic acid sequences encoding those proteins. Generally, the nucleic acid sequence has been incorporated into the genome of the viral vector. In vitro, the viral vector containing h1 or h2 CED-6 protein described herein or nucleic acid sequences encoding the protein can be contacted with a cell and infectivity can occur. The cell can then be used experimentally to study phagocytosis of apoptotic cells or for assays as aforesaid or be implanted into a patient for therapeutic use. The cell can be migratory, such as hematopoietic cells, or non-migratory such as a solid tumor or fibroblast. The cell can be present in a biological sample obtained from the patient (e.g., blood, bone morrow) and used in the treatment of disease, or can be obtained from cell culture.

After contact with the viral vector comprising the h1 or h2 CED-6 protein or a nucleic acid sequence encoding them, the sample can be returned or readministered to a cell culture or patient according to methods known to those practiced in the art. In the case of delivery to a patient or experimental animal model (e.g., rat, mouse, monkey, chimpanzee), such a treatment procedure is sometimes referred to as ex vivo treatment or therapy. Frequently, the cell is targeted from the patient or animal and returned to the patient or animal once contacted with the viral vector comprising the activated mutant of the present invention. Ex vivo gene therapy has been described, for example, in Kasid, et al., *Proc. Natl. Acad. Sci. USA* 87:473 (1990); Rosenberg, et al., *New Engl. J. Med.* 323:570 (1990); Williams, et al., *Nature* 310476 (1984); Dick, et al., Cell 42:71 (1985); Keller, et al., *Nature* 318:149 (1985) and Anderson,. et al., U.S. Pat. No. 5,399, 346 (1994).

Where a cell is contacted In vitro, the cell incorporating the viral vector comprising a nucleic acid sequence of h1CED-6 or h2 CED-6 can be implanted into a patient or experimental animal model for delivery or used in In vitro experimentation to study cellular events mediated by h1 or h2 CED-6.

Various viral vectors can be used to introduce the nucleic acid into mammalian cell. Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-typ6, B-type viruses, D-type viruses, HTLV-BLV group, lentivirus, spumavirus (Coffin, J. M., Retroviridae: The viruses and their replication, *In Fundamental Virology*, Third Edition, B.N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

A preferred method to introduce nucleic acid that encodes h1 or h2 CED-6 into cells is through the use of engineered viral vectors. These vectors provide a means to introduce nucleic acids into cycling and quiescent cells, and have been modified to reduce cytotoxicity and to improve genetic stability. The preparation and use of engineered Herpes simplex virus type 1 (D. M. Krisky, et al., Gene Therapy 4(10):1120–1125. (1997)), adenoviral (A. Amalfitanl, et al., Journal of Virology 72(2).926–933. (1998), attenuated lentiviral (R. Zufferey, et al., Nature Biotechnology 15(9) 871–875 (1997)) and adenoviral/retroviral chimeric (M. Feng,.et al., Nature Biotechnology 15(9):866–870 (1997)) vectors are known to the skilled artisan.

Hence, the claimed invention encompasses various therapeutic uses as aforesaid for the h1 or h2 CED-6 protein or nucleic acid.

The protein may be administered using methods known in the art. For example, the mode of administration Is preferably at the location of the target cells. As such, the administration can be nasally (as in administering a vector expressing ADA) or by injection (as in administering a vector expressing a suicide gene tumor). Other modes of administration (parenteral, mucosal, systemic, implant, intraperitoneal, etc.) are generally known in the art. The agents can, preferably, be, administered in a pharmaceutically acceptable carrier, such as saline, sterile water, Ringer's solution, and Isotonic sodium chloride solution.

The invention also provides diagnostic reagents which may be used in the diagnosis of a disease associated with a defect in phagocytosis of apoptatic cells. For example, an antibody to an epitope of any of the proteins with an amino acid sequence as shown in SEQ ID NOS: 2, 4, 6, 8, 12, 14, 16 or 18 could be used as a diagnostic reagent to determine whether a patient has a defect in h1CED-6, h2CED-6 or in the expression thereof. In addition defects at the genetic level can be detected by using as a probe a nucleic acid having a sequence as shown in SEQ ID NOS: 1, 3, 5, 7, 9, 11, 13, 15 or 17 or portions thereof.

Identification of the other Proteins Active in the CED-6 Signal Transduction Pathway CED-6, h1CED-6 or h2CED-6 can be used to identify other members of the signal transduction pathway promoting phagocytosis of apoptotic cells. There are number of possible methods by which this can be done but a preferred method is the so-called "two hybrid" system developed in yeast by Chien et al. (994, Proc. Natl. Acad Sci. USA 88 pp 9578–9582) which allows identification of proteins which bind to a particular protein of interest.

This technique is based on functional in vivo reconstruction of a transcription factor which activates a reporter gene. More particularly the technique comprises providing an appropriate host cell, preferably yeast, with a DNA construct comprising a reporter gene under the control of a promoter regulated by a transcription factor having a DNA binding domain and an activating domain, expressing in the host cell a first hybrid DNA sequence encoding a first fusion of a fragment or all of a nucleic acid sequence according to the invention and either said DNA binding domain or the activating domain of the transcription factor, expressing in the host cell at least one second hybrid DNA sequence encoding putative binding proteins to be investigated together with the DNA binding domain or activating domain of the transcription factor which is not incorporated in the first fusion; detecting any binding of the protein being investigated with a protein according to the invention by detecting for the production of any reporter gene product in the host cell; optionally isolating second hybrid DNA sequence encoding the binding protein.

EXAMPLES

The N2 Bristol strain was used as the reference wild-type strain for this study. All strains were maintained as described by Brenner (Brenner, 1974), except that worms were raised on NGM-lite agar medium. Strains were maintained and raised at 20° C., unless otherwise noted. The following mutations were used In this study; LG I: ced-1(e1735), ced-1(n1995) and ced-1(n1506) (Ellis et al. 1991); LG III; dpy-17(e164) ced-6(n1813, n2095), mec-14(u55), ncl-1 (e1865) ced-7(n1997), ced-7(n1892), ced-7(n1996) (Ellis et al., 1991), unc-36(e251) (Brenner, 1974) and sDp3(III, f) (Rosenbluth et al., 1985), on LG IV: ced-2(e1752) (Hedgecock et al., 1983), ced-5(n1812) and ced-10(n1993) (Ellis et al., 1991). All mutations are described in Hodgkin (1997).

EXAMPLE 1

Analysis and Quantifying of Engulfment

Animals were anesthetized with 30mM NaN3 and mounted on agar pads to observation using Normarski optics microscope (Sulston & Horvitz, 1977; Avery and Horvitz, 1987). To quantify engulfment of call corpses generated during embryonic development, the number of persistent cell corpses that were visible in the head region of young L1 larvae that still had only four cells in gonad (i.e., had hatched in the previous four hours) were scored. To quantify the germ line engulfment defect cell corpses visible within both the distal arm (where the germ cell deaths occur) and the proximal arm (where persistent germ cell corpses can sometimes be observed as they are swept along by the developing oocytes) were counted.

EXAMPLE 2

Germline Transformation and Genomic Rescue of ced-6

Transgenic animals were generated using the germline microinjection procedure developed by Mello et al. Cosmids W03A5, F20F10, F48E8, R02F2, W02G12, T06H6, C48E6, C44D7, F56D2, F43F12, C05D2, T06C9, C05H8 were injected, either singly or in groups (final concentration 20 ng/ul for each cosmid), into ced-6(n1813) animals. Plasmid pRF4 was used (final concentration 50–80 ng/ul) as the dominant co-injection marker (Mello et al., 1991); pRF4 carries the mutated collagen gene rol-6(su1006 gf) and confers a dominant roller (Rol) phenotype. Transgenic lines carrying stably transmitting extrachromosomal arrays were kept for further analysis. To assay for rescue, three-fold embryos laid by transgenic animals were examined for cell corpses under Normaski optics. Transgenic lines that generated embryos with fewer or no corpses were Considered to be rescued. To further define the position of ced-6 within F56D2, a number of deletion constructs were created and other fragments subcloned into pBluescript SK(+) II. 50–90 ng/ul of these clones were co-injected with 80–100 ng/ul pRF4 injection marker into ced-6(n1813) worms, and their rescuing ability tested as described above.

EXAMPLE 3

Isolation of Ced-6 cDNAs

To isolate full-length ced-6 cDNAs, a mixed-stage C.elegans lambda Zap cDNA library was screened (gift of R. Barstead, Oklahoma Medical Research Foundation, Oklahoma City, Okla.) using established protocols (Sambrook et al., 1989). $^{32}$P-labeled probe was made using the rescuing 10 kb Xho I genomic fragment as template. Positive phage were transformed into plasmid clones using the in vivo excision protocol. The clones representing F56D2.7 gene from isolated plasmid clones were identified on a Southern blot. For this purpose a $^{32}$P-labeled probe was generated from RT-PCR product, which represents three exons of predicted F56D2.7. Primers used for RT-PCR: GAATGTTCTCATT-TATTG (SEQ ID NO.: 19) and GGATTCAAACGATC-CGATG (SEQ ID NO.: 20).

From about 300,000 plaques 10 plasmid clones corresponding F56D2.7 cDNAs were isolated, These clones were sequenced for both ends of the insert using the flanking T3 and T7 primers. Two clones with partial SL2 sequence at the 5' end and intact poly(A) tail were identified as full-length F56D2.7 cDNAs. Analysis of these sequence results and the pattern of restriction digestion by Sau3A I also suggested that these clones represent for one transcript.

EXAMPLE 4

Reverse Transcription-PCR

Reverse transcription (RT)-PCR experiments were performed to determine the 5' end of transcripts detected or predicted within the rescuing Xho I genomic fragment. Reverse transcription was performed with following primers: C05D2.6a; GAATCTGTCCATCGCATTGC (SEQ ID NO.: 21), GAATTTCTTTGGGTAGACA (SEQ ID NO.: 22); C05D2.6b: GCTCTGAAGAACTGTGA (SEQ ID NO.: 23), GACGAGGTGAAGCGATTGTG (SEQ ID NO.: 24): F56D2.7: GGGATCAAACGAATCATC (SEQ ID NO.: 25). These primers were then used in combination with SL1 (GTTTAATTACCCAAGTTTGAG (SEQ ID NO.: 26)) or SL2 (GGTTTTAACCCAGTTACTCAAG (SEQ ID NO.: 27)) primers for subsequent PCR amplification. Total *C. elegans* mixed stage RNA was isolated as described previously RT-PCR was performed using the Superscript Preamplication System (Gibco BRL).

EXAMPLE 5

Identification of Ced-6 Mutations

To determine whether either ced-6 allele resulted in a large physically detectable polymorphism, we generated Southern blots of N2, ced-6(n1813), and ced-6(n2095) genomic DNA digested with various restriction enzymes. A probe generated from the rescuing Xho I genomic fragment detected noval allele-specific bands in ced-6(n2095) using four different restriction enzymes. Analysis of the novel restriction patterns in ced-6(n2095) indicates that this allele carries a complex rearrangement in this region, that covers at least part of F56D2,7, but does not affect the neighboring C05D2.6b transcript.

To identify point mutations within F56D2.7, overlapping fragments of the F56D2.7 locus from N2, ced-6(n1813), and ced-6(n2095) mutants were PCR amplified and directly sequenced using the PCR Product Sequencing Kit (Amersham). The overlapping PCR fragments covered the entire F56D2.7 transcription unit and about 1 kb of upstream genomic sequence. Sequences of the primers used for PCR amplification and sequencing are available upon request.

EXAMPLE 6

Heat Shock Experiments

To test whether ced-6 cDNA can rescue the engulfment defect, Kpn I/Sal I fragment of full-length F56D2.7 cDNA was inserted in Kpn l/Sac I site of MCS II of both pPD49.78 and pPD49.83 vectors which carry hsp16-2 and hsp16-41 promoters, creating the constructs pLQhs 1 and pLQhs2. The two constructs were co-injected, at 50ng/ul each with 80 ng/ul pRF4, to generated stably transmitting extrachromosomal arrays. For our control experiments, we used pPD50.21 and pPD50.15, two derivatives of pPD49.78 and pPD49.83 in which the lacZ open reading frame has been placed under heat shock promoters. Transgenic lines carrying these constructs were generated as described above.

To overexpress ced-6 before cell death occurs during embryonic development, adult animals were put on a plate seeded with *E.coli* and allowed to lay eggs for one hour. Plates were subsequently parafilmed and subjected to heat shock by transfer to 33° C. waterbath for 45 minutes. Following a 75-minute recovery at 20° C., adult animals were removed from the plates. 12–14 hours after heatshock, hatching L1 larvae were scored for corpses in the head region.

To overexpress ced-6 after the formation of cell corpses during embryonic development, worm plates containing embryos at all developmental stages (but not larvae) were parafilmed and subjected to heat shock in a 33° C. waterbath for 45 minutes. Three hours after the heat shock, freshly hatched L1 larvae were scored, for corpses in the head region.

To determine the effect of ced-6 overexpression before cell death occurs on the engulfment of dying germ cells. L4 stage transgenic animals were transferred to new plates and stored at 20° C., Staffing 24 hours after the L4 molt, the worm plates were parafilmed and heat shocked for 45 minutes at 33° C. as described above. Animals were examined for germ cell corpses at 12 hours after heat shock, also 18, 24, 36, and 60 hours after heat shock.

To overexpress ced-6 after the formation of germ cell corpses, L4 stage transgenic animals were collected and put into several plates, a few for each plate. 24 hours after the L4 molt one plate of worms were heat shocked for 45 minutes as described above. Similarly, 36, 42, 48 and 60 hours after the L4 molt, each plate of worms at one time point were treated with heat. Animals were examined for germ cell corpses 12, hours after heat shock.

To overexpress ced-6 in the background of other engulfment mutants, the ced-6 or lacZ-expressing extrachromosomal arrays were transferred from ced-6(n1813) to a wild-type background, and crossed subsequently to ced-1(e1735) ced-1(n1506), ced-1(n1995), ced-7(1892), ced-7(n1996), ced-7(n1997), ced-2(n1752), ced-5(n1812) or ced-10 (n1993) to generate the corresponding transgenic mutant strains. Heat shock experiments were performed as described above.

EXAMPLE 7

Genetic Mosaic Analysis 1000 dpy-17(e164) ced-6(n1813) mec-14(u55) ncl-1 (e1865) unc-36(e25) III; sDp3(III,f) were put in worm plates individually. The progenies of these animals were examined to identify animals who laid only DPY UNC progenies under the dissecting microscope The adult animals were examined under the Normaski Optics immediately after being identified. First the somatic sheath cells were examined then the body wall muscle descended from D and C lineages. When all body wall muscle cells displayed wild-type, the duplication is lost in P4 lineage. When body wall muscle cells from D lineage are wild-type, while those from C lineage exhibit ncl phenotype, the duplication must be lost from P3 lineage. When body wall muscle cells from both D and C lineages show the ncl phenotype, the duplication must be lost from P2 lineage. The cell corpse in both arms of gonad were also examined for the engulfment phenotype. To find the animals with the duplication lost in the somatic sheath cells, but not in germ cells, dpy-17(e164) ced-6 (n1813) mec-14(u55) ncl-1(e1865) unc-36(e25) III; sDp3 (III,f) animals were. examined under the Normaski Optics for the loss of the duplication in somatic sheath cells. At the same time cell corpses in gonad were also examined for the engulfment phenotype.

EXAMPLE 8

Identification of a Human Homologue of CED-6

Extensive searches (tblastn) with the ced-6 sequence (FIG. 15 Consensus DNA Sequence of hCED-6) against the public domain databases (EST, Genbank, EMBL, Swissprot and PIR) revealed statistically significant homologues to some ESTS at the carboxyterminal region of the protein (AA443368, AA431995, R33389, R53881) One EST (T48513) showed homology to the Carboxyterminal of the PTB domain and the beginning of the charged region. For 5' RACE analyses a Marathon-ready cDNA colorectal adenocarcinoma, library was used from Clontech. The position of the primers used for RACE and sequencencing is indicated in FIG. 18. By subsequent cloning and sequence analysis additional sequence information was obtained. Using this additional sequence information and subsequent rounds of database searching (blastn) revealed additional EST, which enabled us to construct a consensus of approx 2400 hp. This sequence was further extended and verified by colony hybridization and sequencing additional RACE products.

EXAMPLE 9

RNA Blots (see FIG. 25 Expression Pattern of hCED-6 in Normal Human Tissues and Cancer Cell Lines by Northern Blotting A) Human Multiple Tissue Northern (MTN) Blot B) Human Multiple Tissue Northern (MTN) Blot II C) Human Cancer Cell Line Multiple Tissue Northern (MTN™) Blot)

A Human multiple tissue Northern (MTN-1, Clontech) containing in each lane 2 mg of poly A+RNA from eight different human tissues (heart, brain, placenta, lung, liver skeletal muscle, kidney, and pancreas) and a MTN-II human multiple tissue Northern, containing in each lane 2 mg of poly A+RNA from spleen, thymus, prostate, testis, ovary, small intestine, colon and peripheral leukocyte, were hybridized according to the manufacturer's instructions and washed out in 0.1×SSC, 0.2% SDS at 55° C., Also from Clontech, a poly A+RNA blot from human cancer cell lines (melanoma G361, lung carcinoma A549, colorectal adenocarcinoma SW480, Burkitt's lymphoma Raji Leukemia Molt 4, lympohoblastic leukemia K562, HeLa S3

EXAMPLE 10

In the ced-6 Cell paper, several human EST clones including hbc 123 have been identified through searching variety of database. The hbc3123 EST clone was completely sequenced. One pair of primers, P and Q have been designed on the region of PTB domain and subsequently tested for their specificity using human genomic DNA (from Wigler lab in Cold Spring Harbor) as a template. The result showed that the primers are specific. One set of λ.gt10 cDNA librarys (a gift from Wigler lab, which they purchased from Clonetech) including Brain, Heart, Kidney, Liver, Lung, Pancreas, Placenta, Skeletal Muscle tissues were tested using primers P and Q to detect whether ced-6 is expressed in any of these tissue.

EXAMPLE 11

To isolate the full-length human ced-6 cDNA. The primer Q and a primer against λ.gt10 vector were used to isolate several PCR fragments using brain and pancreas cDNA librarys. These PCR fragments were reamplified using the same primer set and sequenced The sequence analysis suggested that these PCR fragments allows the extension of cDNA 130 bp upstream of the initiation codon of human ced-6 coding region. The longest PCR fragment was then sent to human EST database to search for more EST clones which have overlapp with the isolated PCR fragments but not the hbc3123 EST clones. The Genbank name of these three EST clones are R65982, R65983 and AA159394. These 3ESTs together with the PCR fragment and hbc3123 constitutes the full-length coding sequence of human CED-6 and about 450 bp of 5' UTR. The human ced-6 cDNA sequenced is confirmed correctly by the sequencing data of hbc3123 EST clone, the sequencing data of the isolated PCR fragments and the sequence data of the many EST clones on the human cDNA region from human EST project. These human ced-6 cDNA data has suggested and guided any further experiments showed in both Example 8 and Example 9.

I. Information Obtained from cDNA Library

| Tissue | Presence of human ced-6 cDNA |
| --- | --- |
| Brain | ++ |
| Heart | ++ |
| Kidney | ++ |
| Liver | + |
| Lung | ++ |
| Pancreas | ++ |
| Placenta | ++ |
| Sketetal muscle | ++ |

II. Information Obtained from Human EST Project

| Tissue | EST clones from human EST project |
| --- | --- |
| Brain | 2 |
| Testis | 3 |
| Pancreas | 4 |
| HCC cell line | 1 |
| Aorta | 1 |
| Placenta | 13 |
| Fetus | 1 |
| Pooled sample | 2 |

EXAMPLE 12

The inventors have carried out the technique known as FISH and have localized the human ced-6 gene to chromosomal position 2q32.3–q33.

EXAMPLE 13

Functional Conservation Between C. Elegans and Human ced-6 Homologues

Given that signal transduction pathways are usually conserved through evolution, it is thought that the human ced-6 homologue (hereafter referred to as h1ced-6) might also be involved in promoting the phagocytic removal of apoptotic cells in mammals. To address this question, we tested the human and worm ced-6 genes for functional conservation by overexpressing h1ced-6 in *C. elegans* and determining whether it could functionally substitute for the endogenous ced-6 gene.

It is shown herein that overexpression of a *C. elegans* ced-6 cDNA under the control of the heat shock promoters hsp16-2 and hsp16–41 efficiently rescues the engulfment defect in transgenic ced-6 mutant embryos. The same assay was used to test h1ced-6 for biological activity in *C. elegans*; constructs were created carrying the h1ced-6 open reading frame under the control of hsp16-2 and hsp16-41, and ced-6(n1813) mutant animals transgenic for both constructs were tested for rescue of the engulfment defect in late embryos and young larvae (see Examples). It was found that heat-shocked embryos laid by transgenic mothers, but not non-heat shocked embryos, contained few cell corpses (Table 2). These observations suggest that h1ced-6 can substitute, albeit weakly in the current assay, for *C. elegans* ced-6, supporting the concept that *C. elegans* and human ced-6 are functionally conserved. h1ced-6 transgenic worms were tested for rescue of the engulfment defect in the adult germ line, but any significant difference was not observed between the transgenic worms and the control non-transgenic ced-6 mutants (Table 3). Given the evidence for rescue in embryos, the absence of rescue in the adult gonad is surprising. It is possible that h1ced-6 is less, well expressed or unstable in the somatic sheath cells. Alternatively, maybe the constellation of proteins involved in the engulfment of apoptotic cells are different in embryos compared to the adult germ line, such that h1CED-6 can function in one context but not the other, Partial rescue, or even absence of rescue in certain assays, has been observed previously, even in cases where functional conservation has been established. For example, Wu and Horvitz (1998a) Nature 1998a 392 501–504, have found that DOCK180, the mammalian homologue of *C. elegans* CED-5, efficiently rescued the engulfment defect of ced-5 mutants, but not the distal tip cell migration defect.

Experimental Procedures

The open reading frame of h1ced-6 was PCR-amplified using oligonucleotides flanking the start and stop codons, and subcloned into the heat shock vectors pPD49.78 and pPD49.83, previously digested with Kpn I and Sac I (see before). The two constructs were then injected into ced-6 (n1813) animals as described previously to establish stably transmitting transgenic lines.

To score for rescue of the engulfment defect in embryos and in the adult germ line, transgenic animals were submitted to heat-shock and the number of cell corpses quantified as described previously herein

TABLE 2

Overexpression of human ced-6 homologue reduces the number of persistent cell corpses in ced-6(n1813) late embryos.

| Genotype | Persistent cell corpses | |
|---|---|---|
| | −heatshock | +heatshock |
| Wild Type (N2) | − | − |
| ced-6(n1813) | +++ | ++ |
| ced-6(n1813); hs::hced-6 | +++ | + |

TABLE 3

Overexpression of human ced-6 homologue fails to reduce the number of persistent cell corpses in the germ line of adult hermaphrodites.

| Genotype | Germ cell corpses (mean ± sem) | |
|---|---|---|
| | −heatshock | +heatshock |
| Wild Type (N2) † | 1 | ND |
| ced-6(n1813) | ND | 29 ± 2 |
| ced-6(n1813); hs::hced-6 #1 | ND | 29 ± 1 |
| ced-6(n1813); hs::hced-6 #2 | ND | 28 ± 1 |
| ced-6(n1813); hs::hced-6 #3 | ND | 29 ± 1 |

† data from Liu and Hengartner (1998)
ND, not determined

EXAMPLE 14

Sequences can be obtained in both deposits Using T3 or T7 primers (either one or both can be used, they are at different sites of the actual insert) Both are commercially available from Clontech (#1227 and #1228) and sequence is shown below T7 primer: 5'(TAATACGACTCACTATAGGGAGA)3' (SEQ ID NO.: 28)

T3 primer; 5'(ATTAACCCTCACTAAAGGGA)3'(SEQ ID NO.: 29)

What is claimed is:

1. An isolated nucleic acid molecule that comprises:
   a) a nucleic acid sequence of SEQ ID NO: 1, 9 or 17; or
   b) the complementary strand of a).

2. An isolated nucleic acid molecule that comprises a nucleic acid sequence of SEQ ID NO: 1, 9 or 17, or the coding region of SEQ ID NO: 1, 9 or 17, and that which encodes a polypeptide having an amino acid sequence of SEQ ID NO: 2, 10 or 18; wherein the encoded polypeptide regulates the engulfment of apoptotic cells or cellular material.

3. An isolated nucleic acid molecule that comprises the coding region of SEQ ID NO: 1, 9, or 17; or the complementary strand of the coding region of SEQ ID NO: 1, 9 or 17; wherein the nucleic acid molecule encodes a polypeptide that regulates the engulfment of apoptotic cells or cellular material.

4. An isolated nucleic acid molecule that encodes a polypeptide having an amino acid sequence of SEQ ID NO: 2, 10 or 18; wherein the encoded polypeptide regulates the engulfment of apoptotic cells or cellular material.

5. An isolated nucleic acid molecule that comprises a nucleic acid sequence that hybridizes under high stringency conditions to a nucleic acid sequence of SEQ ID NO: 1, 9 or 17; wherein the high stringency conditions are 0.1×SSC, 0.2% SDS at 55° C., and the nucleic acid molecule encodes a polypeptide that regulates the engulfment of apoptotic cells or cellular material.

6. An isolated nucleic acid molecule that comprises a nucleic acid sequence that hybridizes under high stringency conditions to the coding region of SEQ ID NO; 1, 9 or 17, or to a nucleic acid sequence that encodes a polypeptide having an amino acid sequence of SEQ ID NO: 2, 10 or 18; wherein the high stringency conditions are 0.1×SSC, 0.2% SDS at 55° C., and the nucleic acid molecule encodes a polypeptide that regulates the engulfment of apoptotic cells or cellular material.

7. A RNA molecule transcribed from a nucleic acid molecule that comprises a nucleic acid sequence of SEQ ID NO: 1, 9 or, 17, or a nucleic acid molecule that encodes a polypeptide having an amino acid sequence of SEQ ID NO: 2, 10 or 18; wherein the encoded polypeptide regulates the engulfment of apoptotic cells or cellular material.

8. A probe that hybridizes under high stringency conditions to a nucleic acid molecule having a nucleic acid sequence of SEQ ID NO: 1, 9 or 17, or the complement of SEQ ID NO: 1, 9 or 17; wherein the high stringency conditions are 0.1×SSC, 0.2% SDS at 55° C., and The nucleic acid molecule encodes a polypeptide that regulates the engulfment of apoptotic cells or cellular material.

9. A vector that comprises a nucleic acid molecule having a nucleic acid sequence of SEQ ID NO: 1, 9 or 17, or e coding region of SEQ ID NO: 1, 9 or 17; a polypeptide that regulates the engulfment of apoptotic cells or cellular material.

10. A vector that comprises a nucleic acid molecule that encodes a polypeptide having an amino acid sequence of SEQ ID NO: 2, 10 or 18; wherein the encoded polypeptide regulates the engulfment of apoptotic cells or cellular material.

11. A vector that comprises a nucleic acid molecule that hybridizes under high stringency conditions to a nucleic acid sequence of SEQ ID NO: 1, 9 or 17 or to the coding region of SEQ ID NO: 1, 9 or 17; wherein the high stringency conditions are 0.1×SSC, 0.2% SDS at 55° C., and the nucleic acid molecule encodes a polypeptide that regulates the engulfment of apoptotic cells or cellular material.

12. A host cell that comprises a nucleic acid molecule having a nucleic acid sequence of SEQ ID NO: 1, 9 or 17 or the coding region of SEQ ID NO: 1, 9 or 17; wherein the nucleic acid molecule encodes a polypeptide that regulates the engulfment of apoptotic cells or cellular material.

13. A host cell that comprises a nucleic acid molecule that encodes a polypeptide having an amino acid sequence of SEQ ID NO: 2, 10 or 18; wherein the encoded polypeptide regulates the engulfment of apoptotic cells or cellular material.

14. A host cell that comprises a nucleic acid molecule that hybridizes under high stringency conditions to a nucleic acid sequence of SEQ ID NO: 1, 9 or 17 or to the coding region of SEQ ID NO: 1, 9, or 17; wherein the high stringency conditions are 0.1×SSC, 0.2% SDS at 55° C., and the nucleic acid molecule encodes a polypeptide that regulates the engulfment of apoptotic cells or cellular material.

15. An isolated nucleic acid molecule obtained from a clone deposited under Belgian Coordinated Collections of Microorganisms (BCCM) NO: LMBP3968, or a nucleic acid sequence obtained from both BCCM NOS: LMBP3868 and LMBP3869, wherein the nucleic acid sequence encodes ced-6.

* * * * *

UNITED STATES PATENT AND TRADEMARK OFFICE
CERTIFICATE OF CORRECTION

PATENT NO. : 6,489,454 B1  
DATED : December 3, 2002  
INVENTOR(S) : Qiong Liu et al.

Page 1 of 1

It is certified that error appears in the above-identified patent and that said Letters Patent is hereby corrected as shown below:

<u>Column 76,</u>
Line 67, delete "e" and insert therefor -- the --;

<u>Column 77,</u>
Lines 1-3, after "17;" add -- wherein the nucleic acid molecule encodes --; and <u>Column 78,</u>
Line 15, delete "NO: LMBP3968" and insert therefor -- NO: LMBP3868 --.

Signed and Sealed this

Ninth Day of March, 2004

JON W. DUDAS  
*Acting Director of the United States Patent and Trademark Office*

SEQUENCE LISTING

<160> NUMBER OF SEQ ID NOS: 44

<210> SEQ ID NO 1
<211> LENGTH: 1728
<212> TYPE: DNA
<213> ORGANISM: Caenorhabditis elegans
<220> FEATURE:
<221> NAME/KEY: CDS
<222> LOCATION: (22)...(1500)

<400> SEQUENCE: 1

-continued

```
tctaaactttt ttctatatca g atg gca aaa gac att tac aag acc ttc aaa     51
                        Met Ala Lys Asp Ile Tyr Lys Thr Phe Lys
                         1               5                  10 cga tcg gtc tcc gga att gtc ggt gga aat aat att aat gga gaa gga     99
Arg Ser Val Ser Gly Ile Val Gly Gly Asn Asn Ile Asn Gly Glu Gly
             15                  20                  25 tct tca agc ccg tcg acg agt gca cca caa gta aaa tat cgt ggt ggg    147
Ser Ser Ser Pro Ser Thr Ser Ala Pro Gln Val Lys Tyr Arg Gly Gly
             30                  35                  40 acc gga aga acg tgg att cat ccg cca gat tat ctt atc aat ggc cat    195
Thr Gly Arg Thr Trp Ile His Pro Pro Asp Tyr Leu Ile Asn Gly His
             45                  50                  55 gtg gaa tat gtt gca cgg ttc ctt gga tgc gtc gaa act cca aaa gca    243
Val Glu Tyr Val Ala Arg Phe Leu Gly Cys Val Glu Thr Pro Lys Ala
     60                  65                  70 aat gga agt gac gtg gca aga gaa gcg atc cac gcg att cga ttt caa    291
Asn Gly Ser Asp Val Ala Arg Glu Ala Ile His Ala Ile Arg Phe Gln
 75                  80                  85                  90 cgc gat ctg aaa cga tct gaa caa acg cgg gag acg gcg aaa ctg caa    339
Arg Asp Leu Lys Arg Ser Glu Gln Thr Arg Glu Thr Ala Lys Leu Gln
                 95                 100                 105 aaa gtg gaa att cgc atc tcg atc gac aat gtg atc att gcg gat att    387
Lys Val Glu Ile Arg Ile Ser Ile Asp Asn Val Ile Ile Ala Asp Ile
                110                 115                 120 aag aca aaa gcg cca atg tac act ttt cca ttg gga aga ata tcg ttt    435
Lys Thr Lys Ala Pro Met Tyr Thr Phe Pro Leu Gly Arg Ile Ser Phe
                125                 130                 135 tgt gct gat gat aaa gat gac aag cga atg ttc tca ttt att gct cgc    483
Cys Ala Asp Asp Lys Asp Asp Lys Arg Met Phe Ser Phe Ile Ala Arg
            140                 145                 150 gcc gag ggt gct agt ggg aag ccg tct tgt tac gcg ttc aca tca gaa    531
Ala Glu Gly Ala Ser Gly Lys Pro Ser Cys Tyr Ala Phe Thr Ser Glu
155                 160                 165                 170 aag cta gct gaa gat atc act cta act atc gga gag gct ttt gat ctc    579
Lys Leu Ala Glu Asp Ile Thr Leu Thr Ile Gly Glu Ala Phe Asp Leu
                175                 180                 185 gcc tac aag aga ttc ctt gat aaa aat cga acg tct ttg gag aat cag    627
Ala Tyr Lys Arg Phe Leu Asp Lys Asn Arg Thr Ser Leu Glu Asn Gln
            190                 195                 200 aag caa ata tac att ttg aag aaa aag att gtg gag ctt gaa acc gag    675
Lys Gln Ile Tyr Ile Leu Lys Lys Lys Ile Val Glu Leu Glu Thr Glu
        205                 210                 215 aat caa gtg ctc att gag cga tta gca gaa gct cta cgg gct aat agt    723
Asn Gln Val Leu Ile Glu Arg Leu Ala Glu Ala Leu Arg Ala Asn Ser
220                 225                 230 aaa gct gat tat gag aac acg ggt ccc cca atc tat cca gga tta ggt    771
Lys Ala Asp Tyr Glu Asn Thr Gly Pro Pro Ile Tyr Pro Gly Leu Gly
235                 240                 245                 250 cct cca gca ctt cca ctt tct ccg atg cct caa gga cct cca cca aac    819
Pro Pro Ala Leu Pro Leu Ser Pro Met Pro Gln Gly Pro Pro Pro Asn
                255                 260                 265 att cct cca tcc tca ata tat tcc atg cca cgt gcc aac gat ctt cca    867
Ile Pro Pro Ser Ser Ile Tyr Ser Met Pro Arg Ala Asn Asp Leu Pro
                270                 275                 280 cca act gaa atg gct cca act ctc cct cag att tct aca tca tca aat    915
Pro Thr Glu Met Ala Pro Thr Leu Pro Gln Ile Ser Thr Ser Ser Asn
            285                 290                 295 gga gca tca cca tcc gtg agc ccg gca tcc aca tca cca tct gga cca    963
Gly Ala Ser Pro Ser Val Ser Pro Ala Ser Thr Ser Pro Ser Gly Pro
```

-continued

```
         300                 305                 310
gct cca tca att cct cca ccg aga cct cct gca ctg gct cct ccg cca    1011
Ala Pro Ser Ile Pro Pro Arg Pro Pro Ala Leu Ala Pro Pro Pro
315                 320                 325                 330 cca gtt gct cca cgc aga aac ccc gtt gtt tca ccg aaa aac tcc acg    1059
Pro Val Ala Pro Arg Arg Asn Pro Val Val Ser Pro Lys Asn Ser Thr
                335                 340                 345 gcg gga ttg ttg gat gga ttg gag ttg ggg tca gct gag ccg gca aaa    1107
Ala Gly Leu Leu Asp Gly Leu Glu Leu Gly Ser Ala Glu Pro Ala Lys
            350                 355                 360 aaa gct cct agt aat att ttc gat gat tcg ttt gat ccc aga gct gga    1155
Lys Ala Pro Ser Asn Ile Phe Asp Asp Ser Phe Asp Pro Arg Ala Gly
        365                 370                 375 gaa aaa aag agc act gca gct gag tat aat cca ttc ggt gcg gac ttc    1203
Glu Lys Lys Ser Thr Ala Ala Glu Tyr Asn Pro Phe Gly Ala Asp Phe
    380                 385                 390 ctc agt ggc att caa aat ggt aaa gaa gca cca cca tca gcc tcc gct    1251
Leu Ser Gly Ile Gln Asn Gly Lys Glu Ala Pro Pro Ser Ala Ser Ala
395                 400                 405                 410 gaa ctt ctc gct tct gaa gca atc gct cgt ctt cca aag cca gaa tcc    1299
Glu Leu Leu Ala Ser Glu Ala Ile Ala Arg Leu Pro Lys Pro Glu Ser
                415                 420                 425 tca tct gta cca ccc aaa aag acc gct gca gag tat gat gca atg atc    1347
Ser Ser Val Pro Pro Lys Lys Thr Ala Ala Glu Tyr Asp Ala Met Ile
            430                 435                 440 aat gaa gtg gag aag aag ctt gcc gcg atg agt agt gga tca ttt gag    1395
Asn Glu Val Glu Lys Lys Leu Ala Ala Met Ser Ser Gly Ser Phe Glu
        445                 450                 455 ttc ggg cag ctt caa acc ggg gac ctt ggc gga atc gaa ggc gaa agc    1443
Phe Gly Gln Leu Gln Thr Gly Asp Leu Gly Gly Ile Glu Gly Glu Ser
    460                 465                 470 gat tat gga aca cca tcg gat cgt ttg aat ccg aaa atg atg aat ttg    1491
Asp Tyr Gly Thr Pro Ser Asp Arg Leu Asn Pro Lys Met Met Asn Leu
475                 480                 485                 490 aag caa taa gtttatttcc ttttttttaa attttccaat tttctacgtt           1540
Lys Gln tcacggtgat ttttttccat tgcattcttg tactattctt gtatcattct tttactagca  1600
gggtttggcc gaacggcttg ccaaatttat tagctgaatg tatttatttg cacgctatca  1660 ttttttaaaaa ttacttactt acttacatgt gaaaaataaa ctggaatgtc tcatggctaa 1720
aaaaaaaa                                                          1728
```

<210> SEQ ID NO 2
<211> LENGTH: 492
<212> TYPE: PRT
<213> ORGANISM: Caenorhabditis elegans

<400> SEQUENCE: 2

```
Met Ala Lys Asp Ile Tyr Lys Thr Phe Lys Arg Ser Val Ser Gly Ile
1               5                   10                  15

Val Gly Gly Asn Asn Ile Asn Gly Glu Gly Ser Ser Ser Pro Ser Thr
            20                  25                  30

Ser Ala Pro Gln Val Lys Tyr Arg Gly Gly Thr Gly Arg Thr Trp Ile
        35                  40                  45

His Pro Pro Asp Tyr Leu Ile Asn Gly His Val Glu Tyr Val Ala Arg
    50                  55                  60

Phe Leu Gly Cys Val Glu Thr Pro Lys Ala Asn Gly Ser Asp Val Ala
65                  70                  75                  80
```

-continued

```
Arg Glu Ala Ile His Ala Ile Arg Phe Gln Arg Asp Leu Lys Arg Ser
                 85                  90                  95
Glu Gln Thr Arg Glu Thr Ala Lys Leu Gln Lys Val Glu Ile Arg Ile
            100                 105                 110
Ser Ile Asp Asn Val Ile Ile Ala Asp Ile Lys Thr Lys Ala Pro Met
            115                 120                 125
Tyr Thr Phe Pro Leu Gly Arg Ile Ser Phe Cys Ala Asp Asp Lys Asp
            130                 135                 140
Asp Lys Arg Met Phe Ser Phe Ile Ala Arg Ala Glu Gly Ala Ser Gly
145                 150                 155                 160
Lys Pro Ser Cys Tyr Ala Phe Thr Ser Glu Lys Leu Ala Glu Asp Ile
                165                 170                 175
Thr Leu Thr Ile Gly Glu Ala Phe Asp Leu Ala Tyr Lys Arg Phe Leu
            180                 185                 190
Asp Lys Asn Arg Thr Ser Leu Glu Asn Gln Lys Gln Ile Tyr Ile Leu
            195                 200                 205
Lys Lys Lys Ile Val Glu Leu Glu Thr Glu Asn Gln Val Leu Ile Glu
            210                 215                 220
Arg Leu Ala Glu Ala Leu Arg Ala Asn Ser Lys Ala Asp Tyr Glu Asn
225                 230                 235                 240
Thr Gly Pro Pro Ile Tyr Pro Gly Leu Gly Pro Ala Leu Pro Leu
                245                 250                 255
Ser Pro Met Pro Gln Gly Pro Pro Asn Ile Pro Ser Ser Ile
            260                 265                 270
Tyr Ser Met Pro Arg Ala Asn Asp Leu Pro Pro Thr Glu Met Ala Pro
            275                 280                 285
Thr Leu Pro Gln Ile Ser Thr Ser Ser Asn Gly Ala Ser Pro Ser Val
            290                 295                 300
Ser Pro Ala Ser Thr Ser Pro Ser Gly Pro Ala Pro Ser Ile Pro Pro
305                 310                 315                 320
Pro Arg Pro Pro Ala Leu Ala Pro Pro Pro Val Ala Pro Arg Arg
                325                 330                 335
Asn Pro Val Val Ser Pro Lys Asn Ser Thr Ala Gly Leu Leu Asp Gly
            340                 345                 350
Leu Glu Leu Gly Ser Ala Glu Pro Ala Lys Lys Ala Pro Ser Asn Ile
            355                 360                 365
Phe Asp Asp Ser Phe Asp Pro Arg Ala Gly Glu Lys Lys Ser Thr Ala
370                 375                 380
Ala Glu Tyr Asn Pro Phe Gly Ala Asp Phe Leu Ser Gly Ile Gln Asn
385                 390                 395                 400
Gly Lys Glu Ala Pro Pro Ser Ala Ser Ala Glu Leu Leu Ala Ser Glu
                405                 410                 415
Ala Ile Ala Arg Leu Pro Lys Pro Glu Ser Ser Val Pro Pro Lys
                420                 425                 430
Lys Thr Ala Ala Glu Tyr Asp Ala Met Ile Asn Glu Val Glu Lys Lys
            435                 440                 445
Leu Ala Ala Met Ser Ser Gly Ser Phe Glu Phe Gly Gln Leu Gln Thr
            450                 455                 460
Gly Asp Leu Gly Gly Ile Glu Gly Glu Ser Asp Tyr Gly Thr Pro Ser
465                 470                 475                 480
Asp Arg Leu Asn Pro Lys Met Met Asn Leu Lys Gln
                485                 490
```

```
<210> SEQ ID NO 3
<211> LENGTH: 435
<212> TYPE: DNA
<213> ORGANISM: Caenorhabditis elegans
<220> FEATURE:
<221> NAME/KEY: CDS
<222> LOCATION: (1)...(438)
<221> NAME/KEY: misc_feature
<222> LOCATION: (0)...(0)
<223> OTHER INFORMATION: PTB domain

<400> SEQUENCE: 3 cat ccg cca gat tat ctt atc aat ggc cat gtg gaa tat gtt gca cgg      48
His Pro Pro Asp Tyr Leu Ile Asn Gly His Val Glu Tyr Val Ala Arg
 1               5                  10                  15 ttc ctt gga tgc gtc gaa act cca aaa gca aat gga agt gac gtg gca      96
Phe Leu Gly Cys Val Glu Thr Pro Lys Ala Asn Gly Ser Asp Val Ala
             20                  25                  30 aga gaa gcg atc cac gcg att cga ttt caa cgc gat ctg aaa cga tct     144
Arg Glu Ala Ile His Ala Ile Arg Phe Gln Arg Asp Leu Lys Arg Ser
         35                  40                  45 gaa caa acg cgg gag acg gcg aaa ctg caa aaa gtg gaa att cgc atc     192
Glu Gln Thr Arg Glu Thr Ala Lys Leu Gln Lys Val Glu Ile Arg Ile
     50                  55                  60 tcg atc gac aat gtg atc att gcg gat att aag aca aaa gcg cca atg     240
Ser Ile Asp Asn Val Ile Ile Ala Asp Ile Lys Thr Lys Ala Pro Met
65                  70                  75                  80 tac act ttt cca ttg gga aga ata tcg ttt tgt gct gat gat aaa gat     288
Tyr Thr Phe Pro Leu Gly Arg Ile Ser Phe Cys Ala Asp Asp Lys Asp
                 85                  90                  95 gac aag cga atg ttc tca ttt att gct cgc gcc gag ggt gct agt ggg     336
Asp Lys Arg Met Phe Ser Phe Ile Ala Arg Ala Glu Gly Ala Ser Gly
            100                 105                 110 aag ccg tct tgt tac gcg ttc aca tca gaa aag cta gct gaa gat atc     384
Lys Pro Ser Cys Tyr Ala Phe Thr Ser Glu Lys Leu Ala Glu Asp Ile
        115                 120                 125 act cta act atc gga gag gct ttt gat ctc gcc tac aag aga ttc ctt     432
Thr Leu Thr Ile Gly Glu Ala Phe Asp Leu Ala Tyr Lys Arg Phe Leu
    130                 135                 140 gat                                                                  435
Asp
145

<210> SEQ ID NO 4
<211> LENGTH: 145
<212> TYPE: PRT
<213> ORGANISM: Caenorhabditis elegans
<220> FEATURE:
<223> OTHER INFORMATION: PTB Domain

<400> SEQUENCE: 4

His Pro Pro Asp Tyr Leu Ile Asn Gly His Val Glu Tyr Val Ala Arg
 1               5                  10                  15

Phe Leu Gly Cys Val Glu Thr Pro Lys Ala Asn Gly Ser Asp Val Ala
             20                  25                  30

Arg Glu Ala Ile His Ala Ile Arg Phe Gln Arg Asp Leu Lys Arg Ser
         35                  40                  45

Glu Gln Thr Arg Glu Thr Ala Lys Leu Gln Lys Val Glu Ile Arg Ile
     50                  55                  60

Ser Ile Asp Asn Val Ile Ile Ala Asp Ile Lys Thr Lys Ala Pro Met
65                  70                  75                  80
```

```
Tyr Thr Phe Pro Leu Gly Arg Ile Ser Phe Cys Ala Asp Asp Lys Asp
                85                  90                  95

Asp Lys Arg Met Phe Ser Phe Ile Ala Arg Ala Glu Gly Ala Ser Gly
            100                 105                 110

Lys Pro Ser Cys Tyr Ala Phe Thr Ser Glu Lys Leu Ala Glu Asp Ile
        115                 120                 125

Thr Leu Thr Ile Gly Glu Ala Phe Asp Leu Ala Tyr Lys Arg Phe Leu
    130                 135                 140

Asp
145

<210> SEQ ID NO 5
<211> LENGTH: 291
<212> TYPE: DNA
<213> ORGANISM: Caenorhabditis elegans
<220> FEATURE:
<221> NAME/KEY: CDS
<222> LOCATION: (1)...(294)
<221> NAME/KEY: misc_feature
<222> LOCATION: (0)...(0)
<223> OTHER INFORMATION: Proline/Serine rich region

<400> SEQUENCE: 5 ggt ccc cca atc tat cca gga tta ggt cct cca gca ctt cca ctt tct        48
Gly Pro Pro Ile Tyr Pro Gly Leu Gly Pro Pro Ala Leu Pro Leu Ser
 1               5                  10                  15 ccg atg cct caa gga cct cca cca aac att cct cca tcc tca ata tat        96
Pro Met Pro Gln Gly Pro Pro Pro Asn Ile Pro Pro Ser Ser Ile Tyr
            20                  25                  30 tcc atg cca cgt gcc aac gat ctt cca cca act gaa atg gct cca act       144
Ser Met Pro Arg Ala Asn Asp Leu Pro Pro Thr Glu Met Ala Pro Thr
        35                  40                  45 ctc cct cag att tct aca tca tca aat gga gca tca cca tcc gtg agc       192
Leu Pro Gln Ile Ser Thr Ser Ser Asn Gly Ala Ser Pro Ser Val Ser
    50                  55                  60 ccg gca tcc aca tca cca tct gga cca gct cca tca att cct cca ccg       240
Pro Ala Ser Thr Ser Pro Ser Gly Pro Ala Pro Ser Ile Pro Pro Pro
65                  70                  75                  80 aga cct cct gca ctg gct cct ccg cca cca gtt gct cca cgc aga aac       288
Arg Pro Pro Ala Leu Ala Pro Pro Pro Pro Val Ala Pro Arg Arg Asn
                85                  90                  95 ccc                                                                    291
Pro

<210> SEQ ID NO 6
<211> LENGTH: 97
<212> TYPE: PRT
<213> ORGANISM: Caenorhabditis elegans
<220> FEATURE:
<223> OTHER INFORMATION: Proline/Serine rich region

<400> SEQUENCE: 6

Gly Pro Pro Ile Tyr Pro Gly Leu Gly Pro Pro Ala Leu Pro Leu Ser
 1               5                  10                  15

Pro Met Pro Gln Gly Pro Pro Pro Asn Ile Pro Pro Ser Ser Ile Tyr
            20                  25                  30

Ser Met Pro Arg Ala Asn Asp Leu Pro Pro Thr Glu Met Ala Pro Thr
        35                  40                  45

Leu Pro Gln Ile Ser Thr Ser Ser Asn Gly Ala Ser Pro Ser Val Ser
    50                  55                  60

Pro Ala Ser Thr Ser Pro Ser Gly Pro Ala Pro Ser Ile Pro Pro Pro
```

```
                65                  70                  75                  80
               Arg Pro Pro Ala Leu Ala Pro Pro Pro Val Ala Pro Arg Arg Asn
                                85                  90                  95

Pro

<210> SEQ ID NO 7
<211> LENGTH: 138
<212> TYPE: DNA
<213> ORGANISM: Caenorhabditis elegans
<220> FEATURE:
<221> NAME/KEY: CDS
<222> LOCATION: (1)...(138)
<221> NAME/KEY: misc_feature
<222> LOCATION: (0)...(0)
<223> OTHER INFORMATION: charged region

<400> SEQUENCE: 7 aaa aat cga acg tct ttg gag aat cag aag caa ata tac att ttg aag        48
Lys Asn Arg Thr Ser Leu Glu Asn Gln Lys Gln Ile Tyr Ile Leu Lys
 1               5                  10                  15 aaa aag att gtg gag ctt gaa acc gag aat caa gtg ctc att gag cga        96
Lys Lys Ile Val Glu Leu Glu Thr Glu Asn Gln Val Leu Ile Glu Arg
                20                  25                  30 tta gca gaa gct cta cgg gct aat agt aaa gct gat tat gag                138
Leu Ala Glu Ala Leu Arg Ala Asn Ser Lys Ala Asp Tyr Glu
            35                  40                  45

<210> SEQ ID NO 8
<211> LENGTH: 46
<212> TYPE: PRT
<213> ORGANISM: Caenorhabditis elegans
<220> FEATURE:
<223> OTHER INFORMATION: charged region

<400> SEQUENCE: 8

Lys Asn Arg Thr Ser Leu Glu Asn Gln Lys Gln Ile Tyr Ile Leu Lys
 1               5                  10                  15

Lys Lys Ile Val Glu Leu Glu Thr Glu Asn Gln Val Leu Ile Glu Arg
                20                  25                  30

Leu Ala Glu Ala Leu Arg Ala Asn Ser Lys Ala Asp Tyr Glu
            35                  40                  45

<210> SEQ ID NO 9
<211> LENGTH: 2412
<212> TYPE: DNA
<213> ORGANISM: Human
<220> FEATURE:
<221> NAME/KEY: CDS
<222> LOCATION: (430)...(1343)

<400> SEQUENCE: 9
ggtgatgagc ccttgggttc tcgctccgac tgctaaattc gcttggccgg gtccaccttc        60
tcgtggcctc actcgccaca cggatcagaa tccggagcag gcagttctct ctattctgag       120
gctcctgcgg ctgccggctg acttcccgt gtgcgggagg gaactctggg caggctggtt        180
ttcttggaat gtgtttacga tgttgaatgg gacttgaaca ggaagctgga cgctgcagct       240
ggaactagcg tgccaagtta tttatgattc catctgatat acataggaga gaaactgata       300
gaagaattct gatggcaact gtatgataga agctattata agtcaagtg tccattttct        360 ttcaactata tttgagcata cccaggattt aagtcgtgga actgaacatt tatttggctg       420 atcctcatc atg aac cgt gct ttt agc agg aag aaa gac aaa aca tgg atg       471
           Met Asn Arg Ala Phe Ser Arg Lys Lys Asp Lys Thr Trp Met
```

-continued

```
                 1                    5                         10
cat aca cct gaa gct tta tca aaa cat ttc att ccc tat aat gca aag      519
His Thr Pro Glu Ala Leu Ser Lys His Phe Ile Pro Tyr Asn Ala Lys
 15                  20                  25                  30 ttt ctt ggc agt aca gaa gtg gaa cag cca aaa gga aca gaa gtt gtg      567
Phe Leu Gly Ser Thr Glu Val Glu Gln Pro Lys Gly Thr Glu Val Val
                 35                  40                  45 aga gat gct gta agg aaa cta aag ttt gca aga cat atc aag aaa tct      615
Arg Asp Ala Val Arg Lys Leu Lys Phe Ala Arg His Ile Lys Lys Ser
             50                  55                  60 gaa ggc cag aaa att cct aaa gtg gag ttg caa ata tca att tat gga      663
Glu Gly Gln Lys Ile Pro Lys Val Glu Leu Gln Ile Ser Ile Tyr Gly
         65                  70                  75 gta aaa att cta gaa ccc aaa aca aag gaa gtt caa cac aat tgc cag      711
Val Lys Ile Leu Glu Pro Lys Thr Lys Glu Val Gln His Asn Cys Gln
     80                  85                  90 ctt cat aga ata tct ttt tgt gca gat gat aaa act gac aag agg ata      759
Leu His Arg Ile Ser Phe Cys Ala Asp Asp Lys Thr Asp Lys Arg Ile
 95                 100                 105                 110 ttc act ttc ata tgc aaa gat tct gag tca aat aaa cat ttg tgc tat      807
Phe Thr Phe Ile Cys Lys Asp Ser Glu Ser Asn Lys His Leu Cys Tyr
                115                 120                 125 gta ttt gac agc gaa aag tgt gct gaa gag atc act tta aca att ggc      855
Val Phe Asp Ser Glu Lys Cys Ala Glu Glu Ile Thr Leu Thr Ile Gly
            130                 135                 140 caa gca ttt gac ctg gca tac agg aaa ttt cta gaa tca gga gga aaa      903
Gln Ala Phe Asp Leu Ala Tyr Arg Lys Phe Leu Glu Ser Gly Gly Lys
        145                 150                 155 gat gtt gaa aca aga aaa cag atc gca ggg tta caa aaa aga atc caa      951
Asp Val Glu Thr Arg Lys Gln Ile Ala Gly Leu Gln Lys Arg Ile Gln
    160                 165                 170 gac tta gaa aca gaa aat atg gaa ctt aaa aat aaa gta caa gat ttg      999
Asp Leu Glu Thr Glu Asn Met Glu Leu Lys Asn Lys Val Gln Asp Leu
175                 180                 185                 190 gaa aac caa ctg aga ata act caa gta tca gca cct cca gca ggc agt     1047
Glu Asn Gln Leu Arg Ile Thr Gln Val Ser Ala Pro Pro Ala Gly Ser
                195                 200                 205 atg aca cct aag tcg ccc tcc act gac atc ttt gat atg att cca ttt     1095
Met Thr Pro Lys Ser Pro Ser Thr Asp Ile Phe Asp Met Ile Pro Phe
            210                 215                 220 tct cca ata tca cac cag tct tcg atg cct act cgc aat ggc aca cag     1143
Ser Pro Ile Ser His Gln Ser Ser Met Pro Thr Arg Asn Gly Thr Gln
        225                 230                 235 cca cct cca gta cct agt aga tct act gag att aaa cgg gac ctg ttt     1191
Pro Pro Pro Val Pro Ser Arg Ser Thr Glu Ile Lys Arg Asp Leu Phe
    240                 245                 250 gga gca gaa cct ttt gac cca ttt aac tgt gga gca gca gat ttc cct     1239
Gly Ala Glu Pro Phe Asp Pro Phe Asn Cys Gly Ala Ala Asp Phe Pro
255                 260                 265                 270 cca gat att caa tca aaa tta gat gag atg cag gag ggg ttc aaa atg     1287
Pro Asp Ile Gln Ser Lys Leu Asp Glu Met Gln Glu Gly Phe Lys Met
                275                 280                 285 gga cta act ctt gaa ggc aca gta ttt tgt ctc gac ccg tta gac agt     1335
Gly Leu Thr Leu Glu Gly Thr Val Phe Cys Leu Asp Pro Leu Asp Ser
            290                 295                 300 agg tgc tg acatcaagaa caagaaatcc tgattcatgt taaatgtgtt tgtatacaca   1393
Arg Cys tgtcatttat tattattact ttaagatagg tattattcat gtgtcaatgt ttttgaatat   1453
```

-continued

```
tttaatatttt tgaaaatttt ctcagttaaa tttcctcacc ttcactattg atctgtaatt      1513
tttattttaa aaacagctta ctgtaaagta gatcatactt ttatgttcct ttctgtttct      1573
actgtagatg aatttgtaat tgaaagacat attatacaaa tacctgcctt gtgtctgagt      1633
tctatttagt tagcatcttg aaatttgtat tcattttcca gatggctagt ttattaatga      1693
tttcccaaaa gccatacctt aaagataact ttttaaattc tgaagagaca tgccaatgtc      1753
aaactaaaca tgttctgttt ttaaaccaac aaacatgtta ctattcattg gacagatatc      1813
attttatgta taaatactgt tcacatcact gggaaaatgt aaactttaaa cataatgcca      1873
caaggtcact aatttctagc aggtaaaatt ataaggatat aaattccaat aataaaccaa      1933
atgtatttag agtatttatt agtaaatgca aggtgatgtt agttatgatc agttatactc      1993
taaatattta atttgtttta taaggtagt gaaaaaatga aaatttgcta tttattaaaa       2053
aacattaaat ttcattccaa atgagataag tgatattact ataacatcta agcatcatct      2113
gatttgatat tccctaaaaa acatttggaa tatatgctat ctatagattc agtatctact      2173
acccatattt actttaccaa atatatttct cctcactgca taaggactac tcttctcata      2233
ttttcttctt tgatgaagat attttttcacc aaagtttatt ttgtgatgcc ctcttggttt     2293
tgatacttta aaatctgtgg cacccgttct acatgaatta tcaatatttg gtaaattcaa      2353
tctgtatttg ttttgttaaa gtcaaaaatc tcattttcca aaaaaaaaaa aaaaaaaac      2412
```

<210> SEQ ID NO 10
<211> LENGTH: 304
<212> TYPE: PRT
<213> ORGANISM: Human

<400> SEQUENCE: 10

```
Met Asn Arg Ala Phe Ser Arg Lys Lys Asp Lys Thr Trp Met His Thr
  1               5                  10                  15

Pro Glu Ala Leu Ser Lys His Phe Ile Pro Tyr Asn Ala Lys Phe Leu
                 20                  25                  30

Gly Ser Thr Glu Val Glu Gln Pro Lys Gly Thr Glu Val Val Arg Asp
             35                  40                  45

Ala Val Arg Lys Leu Lys Phe Ala Arg His Ile Lys Lys Ser Glu Gly
         50                  55                  60

Gln Lys Ile Pro Lys Val Glu Leu Gln Ile Ser Ile Tyr Gly Val Lys
     65                  70                  75                  80

Ile Leu Glu Pro Lys Thr Lys Glu Val Gln His Asn Cys Gln Leu His
                 85                  90                  95

Arg Ile Ser Phe Cys Ala Asp Asp Lys Thr Asp Lys Arg Ile Phe Thr
            100                 105                 110

Phe Ile Cys Lys Asp Ser Glu Ser Asn Lys His Leu Cys Tyr Val Phe
        115                 120                 125

Asp Ser Glu Lys Cys Ala Glu Glu Ile Thr Leu Thr Ile Gly Gln Ala
    130                 135                 140

Phe Asp Leu Ala Tyr Arg Lys Phe Leu Glu Ser Gly Gly Lys Asp Val
145                 150                 155                 160

Glu Thr Arg Lys Gln Ile Ala Gly Leu Gln Lys Arg Ile Gln Asp Leu
                165                 170                 175

Glu Thr Glu Asn Met Glu Leu Lys Asn Lys Val Gln Asp Leu Glu Asn
            180                 185                 190

Gln Leu Arg Ile Thr Gln Val Ser Ala Pro Pro Ala Gly Ser Met Thr
        195                 200                 205
```

```
Pro Lys Ser Pro Ser Thr Asp Ile Phe Asp Met Ile Pro Phe Ser Pro
    210                 215                 220
Ile Ser His Gln Ser Ser Met Pro Thr Arg Asn Gly Thr Gln Pro Pro
225                 230                 235                 240
Pro Val Pro Ser Arg Ser Thr Glu Ile Lys Arg Asp Leu Phe Gly Ala
                245                 250                 255
Glu Pro Phe Asp Pro Phe Asn Cys Gly Ala Ala Asp Phe Pro Pro Asp
            260                 265                 270
Ile Gln Ser Lys Leu Asp Glu Met Gln Glu Gly Phe Lys Met Gly Leu
        275                 280                 285
Thr Leu Glu Gly Thr Val Phe Cys Leu Asp Pro Leu Asp Ser Arg Cys
    290                 295                 300
```

<210> SEQ ID NO 11
<211> LENGTH: 429
<212> TYPE: DNA
<213> ORGANISM: Human
<220> FEATURE:
<221> NAME/KEY: CDS
<222> LOCATION: (1)...(429)
<221> NAME/KEY: misc_feature
<222> LOCATION: (0)...(0)
<223> OTHER INFORMATION: PTB Domain

<400> SEQUENCE: 11

```
cat aca cct gaa gct tta tca aaa cat ttc att ccc tat aat gca aag      48
His Thr Pro Glu Ala Leu Ser Lys His Phe Ile Pro Tyr Asn Ala Lys
1               5                   10                  15 ttt ctt ggc agt aca gaa gtg gaa cag cca aaa gga aca gaa gtt gtg     96
Phe Leu Gly Ser Thr Glu Val Glu Gln Pro Lys Gly Thr Glu Val Val
            20                  25                  30 aga gat gct gta agg aaa cta aag ttt gca aga cat atc aag aaa tct    144
Arg Asp Ala Val Arg Lys Leu Lys Phe Ala Arg His Ile Lys Lys Ser
        35                  40                  45 gaa ggc cag aaa att cct aaa gtg gag ttg caa ata tca att tat gga    192
Glu Gly Gln Lys Ile Pro Lys Val Glu Leu Gln Ile Ser Ile Tyr Gly
    50                  55                  60 gta aaa att cta gaa ccc aaa aca aag gaa gtt caa cac aat tgc cag    240
Val Lys Ile Leu Glu Pro Lys Thr Lys Glu Val Gln His Asn Cys Gln
65                  70                  75                  80 ctt cat aga ata tct ttt tgt gca gat gat aaa act gac aag agg ata    288
Leu His Arg Ile Ser Phe Cys Ala Asp Asp Lys Thr Asp Lys Arg Ile
                85                  90                  95 ttc act ttc ata tgc aaa gat tct gag tca aat aaa cat ttg tgc tat    336
Phe Thr Phe Ile Cys Lys Asp Ser Glu Ser Asn Lys His Leu Cys Tyr
            100                 105                 110 gta ttt gac agc gaa aag tgt gct gaa gag atc act tta aca att ggc    384
Val Phe Asp Ser Glu Lys Cys Ala Glu Glu Ile Thr Leu Thr Ile Gly
        115                 120                 125 caa gca ttt gac ctg gca tac acg aaa ttt cta gaa tca gga gga         429
Gln Ala Phe Asp Leu Ala Tyr Thr Lys Phe Leu Glu Ser Gly Gly
    130                 135                 140
```

<210> SEQ ID NO 12
<211> LENGTH: 143
<212> TYPE: PRT
<213> ORGANISM: Human
<220> FEATURE:
<223> OTHER INFORMATION: PTB Domain

<400> SEQUENCE: 12

His Thr Pro Glu Ala Leu Ser Lys His Phe Ile Pro Tyr Asn Ala Lys

```
                1               5                    10                       15
          Phe Leu Gly Ser Thr Glu Val Glu Gln Pro Lys Gly Thr Glu Val Val
                                20                       25                  30

Arg Asp Ala Val Arg Lys Leu Lys Phe Ala Arg His Ile Lys Lys Ser
                        35                       40                  45

Glu Gly Gln Lys Ile Pro Lys Val Glu Leu Gln Ile Ser Ile Tyr Gly
                  50                       55                  60

Val Lys Ile Leu Glu Pro Lys Thr Lys Glu Val Gln His Asn Cys Gln
           65                       70                  75                  80

Leu His Arg Ile Ser Phe Cys Ala Asp Asp Lys Thr Asp Lys Arg Ile
                                85                  90                  95

Phe Thr Phe Ile Cys Lys Asp Ser Glu Ser Asn Lys His Leu Cys Tyr
                              100                     105                 110

Val Phe Asp Ser Glu Lys Cys Ala Glu Glu Ile Thr Leu Thr Ile Gly
                          115                     120                 125

Gln Ala Phe Asp Leu Ala Tyr Thr Lys Phe Leu Glu Ser Gly Gly
                      130                     135                 140
```

<210> SEQ ID NO 13
<211> LENGTH: 228
<212> TYPE: DNA
<213> ORGANISM: Human
<220> FEATURE:
<221> NAME/KEY: CDS
<222> LOCATION: (1)...(228)
<221> NAME/KEY: misc_feature
<222> LOCATION: (0)...(0)
<223> OTHER INFORMATION: Proline/Serine Rich Region

<400> SEQUENCE: 13

```
gca cct cca gca ggc agt atg aca cct aag tcg ccc tcc act gac atc        48
Ala Pro Pro Ala Gly Ser Met Thr Pro Lys Ser Pro Ser Thr Asp Ile
 1               5                      10                     15 ttt gat atg att cca ttt tct cca ata tca cac cag tct tcg atg cct        96
Phe Asp Met Ile Pro Phe Ser Pro Ile Ser His Gln Ser Ser Met Pro
                20                      25                     30 act cgc aat ggc aca cag cca cct cca gta cct agt aga tct act gag       144
Thr Arg Asn Gly Thr Gln Pro Pro Pro Val Pro Ser Arg Ser Thr Glu
            35                      40                  45 att aaa cgg gac ctg ttt gga gca gaa cct ttt gac cca ttt aac tgt       192
Ile Lys Arg Asp Leu Phe Gly Ala Glu Pro Phe Asp Pro Phe Asn Cys
        50                      55                  60 gga gca gca gat ttc cct cca gat att caa tca aaa                       228
Gly Ala Ala Asp Phe Pro Pro Asp Ile Gln Ser Lys
 65                     70                  75
```

<210> SEQ ID NO 14
<211> LENGTH: 76
<212> TYPE: PRT
<213> ORGANISM: Human
<220> FEATURE:
<223> OTHER INFORMATION: Proline/Serine Rich Region

<400> SEQUENCE: 14

```
Ala Pro Pro Ala Gly Ser Met Thr Pro Lys Ser Pro Ser Thr Asp Ile
 1               5                      10                     15

Phe Asp Met Ile Pro Phe Ser Pro Ile Ser His Gln Ser Ser Met Pro
                20                      25                     30

Thr Arg Asn Gly Thr Gln Pro Pro Pro Val Pro Ser Arg Ser Thr Glu
            35                      40                  45
```

```
Ile Lys Arg Asp Leu Phe Gly Ala Glu Pro Phe Asp Pro Phe Asn Cys
             50                  55                  60

Gly Ala Ala Asp Phe Pro Pro Asp Ile Gln Ser Lys
 65                  70                  75

<210> SEQ ID NO 15
<211> LENGTH: 105
<212> TYPE: DNA
<213> ORGANISM: Human
<220> FEATURE:
<221> NAME/KEY: CDS
<222> LOCATION: (1)...(105)
<221> NAME/KEY: misc_feature
<222> LOCATION: (0)...(0)
<223> OTHER INFORMATION: charged region

<400> SEQUENCE: 15 gaa aca aga aaa cag atc gca ggg tta caa aaa aga atc caa gac tta      48
Glu Thr Arg Lys Gln Ile Ala Gly Leu Gln Lys Arg Ile Gln Asp Leu
  1               5                  10                  15 gaa aca gaa aat atg gaa ctt aaa aat aaa gta caa gat ttg gaa aac      96
Glu Thr Glu Asn Met Glu Leu Lys Asn Lys Val Gln Asp Leu Glu Asn
             20                  25                  30 caa ctg aga                                                         105
Gln Leu Arg
        35

<210> SEQ ID NO 16
<211> LENGTH: 35
<212> TYPE: PRT
<213> ORGANISM: Human
<220> FEATURE:
<223> OTHER INFORMATION: charged region

<400> SEQUENCE: 16

Glu Thr Arg Lys Gln Ile Ala Gly Leu Gln Lys Arg Ile Gln Asp Leu
  1               5                  10                  15

Glu Thr Glu Asn Met Glu Leu Lys Asn Lys Val Gln Asp Leu Glu Asn
             20                  25                  30

Gln Leu Arg
        35

<210> SEQ ID NO 17
<211> LENGTH: 2273
<212> TYPE: DNA
<213> ORGANISM: Human
<220> FEATURE:
<221> NAME/KEY: CDS
<222> LOCATION: (430)...(1206)
<221> NAME/KEY: misc_feature
<222> LOCATION: (1)...(2278)
<223> OTHER INFORMATION: n=A,T,C or G
<220> FEATURE:
<221> NAME/KEY: misc_feature
<222> LOCATION: (1)...(2273)
<223> OTHER INFORMATION: n = A,T,C or G

<400> SEQUENCE: 17
ggtgatgagc ccttgggttc tcgctccgac tgctaaattc gcttggccgg gtccaccttc      60
tcgtggcctc actcgccaca cggatcagaa tccggagcag gcagttctct ctattctgag     120
gctcctgcgg ctgccgcgct gacttccctg tgtggngag ggaactctgg gcaggctggt     180
tttcttggaa tgtgtttacg atgttgaatg ggacttgaac aggaagctgg acgctgcagc     240
tggaactagc gtgccaagtt atttatgatt ccatctgata tacataggag agaaactgat     300
```

```
agaagaattc tgatggcaac tgtatgatag aagctatata aagtcaagtg tccattttct      360
ttcaactata tttgagcata cccaggattt aagtcgtgga actgaacatt tatttggctg      420 atcctcatc atg aac cgt gct ttt agc agg aag aaa gac aaa aca tgg atg      471
          Met Asn Arg Ala Phe Ser Arg Lys Lys Asp Lys Thr Trp Met
           1               5                  10 cat aca cct gaa gct tta tca aaa cat ttc att ccc tat aat gca aag        519
His Thr Pro Glu Ala Leu Ser Lys His Phe Ile Pro Tyr Asn Ala Lys
 15              20                  25                  30 ttt ctt ggc agt aca gaa gtg gaa cag cca aaa gga aca gaa gtt gtg        567
Phe Leu Gly Ser Thr Glu Val Glu Gln Pro Lys Gly Thr Glu Val Val
                 35                  40                  45 aga gat gct gta agg aaa cta aag ttt gca aga cat atc aag aaa tct        615
Arg Asp Ala Val Arg Lys Leu Lys Phe Ala Arg His Ile Lys Lys Ser
             50                  55                  60 gaa ggc cag aaa att cct aaa gtg gag ttg caa ata tca att tat gga        663
Glu Gly Gln Lys Ile Pro Lys Val Glu Leu Gln Ile Ser Ile Tyr Gly
         65                  70                  75 gta aaa att cta gaa ccc aaa aca aag gct gaa gag atc act tta aca        711
Val Lys Ile Leu Glu Pro Lys Thr Lys Ala Glu Glu Ile Thr Leu Thr
     80                  85                  90 att ggc caa gca ttt gac ctg gca tac agg aaa ttt cta gaa tca gga        759
Ile Gly Gln Ala Phe Asp Leu Ala Tyr Arg Lys Phe Leu Glu Ser Gly
 95                 100                 105                 110 gga aaa gat gtt gaa aca aga aaa cag atc gca ggg tta caa aaa aga        807
Gly Lys Asp Val Glu Thr Arg Lys Gln Ile Ala Gly Leu Gln Lys Arg
                115                 120                 125 atc caa gac tta gaa aca gaa aat atg gaa ctt aaa aat aaa gta caa        855
Ile Gln Asp Leu Glu Thr Glu Asn Met Glu Leu Lys Asn Lys Val Gln
            130                 135                 140 gat ttg gaa aac caa ctg aga ata act caa gta tca gca cct cca gca        903
Asp Leu Glu Asn Gln Leu Arg Ile Thr Gln Val Ser Ala Pro Pro Ala
        145                 150                 155 ggc agt atg aca cct aag tcg ccc tcc act gac atc ttt gat atg att        951
Gly Ser Met Thr Pro Lys Ser Pro Ser Thr Asp Ile Phe Asp Met Ile
    160                 165                 170 cca ttt tct cca ata tca cac cag tct tcg atg cct act cgc aat ggc        999
Pro Phe Ser Pro Ile Ser His Gln Ser Ser Met Pro Thr Arg Asn Gly
175                 180                 185                 190 aca cag cca cct cca gta cct agt aga tct act gag att aaa cgg gac       1047
Thr Gln Pro Pro Pro Val Pro Ser Arg Ser Thr Glu Ile Lys Arg Asp
                195                 200                 205 ctg ttt gga gca gaa cct ttt gac cca ttt aac tgt gga gca gca gat       1095
Leu Phe Gly Ala Glu Pro Phe Asp Pro Phe Asn Cys Gly Ala Ala Asp
            210                 215                 220 ttc cct cca gat att caa tca aaa tta gat gag atg cag gag ggg ttc       1143
Phe Pro Pro Asp Ile Gln Ser Lys Leu Asp Glu Met Gln Glu Gly Phe
        225                 230                 235 aaa atg gga cta act ctt gaa ggc aca gta ttt tgt ctc gac ccg tta       1191
Lys Met Gly Leu Thr Leu Glu Gly Thr Val Phe Cys Leu Asp Pro Leu
    240                 245                 250 gac agt agg tgc tga catcaagaac aagaaatcct gattcatgtt aaatgtgttt       1246
Asp Ser Arg Cys
255 gtatacacat gtcatttatt attattactt taagataggt attattcatg tgtcaatgtt     1306 tttgaatatt ttaatatttt gaaaattttc tcagttaaat ttcctcacct tcactattga     1366 tctgtaattt ttattttaaa aacagcttac tgtaaagtag atcatacttt tatgttcctt     1426 tctgtttcta ctgtagatga atttgtaatt gaaagacata ttatacaaat acctgccttg     1486
```

-continued

```
tgtctgagtt ctatttagtt agcatcttga aatttgtatt cattttccag atggctagtt    1546
tattaatgat ttcccaaaag ccataccta aagataactt tttaaattct gaagagacat     1606
gccaatgtca aactaaacat gttctgtttt taaaccaaca aacatgttac tattcattgg    1666
acagatatca ttttatgtat aaatactgtt cacatcactg ggaaaatgta aactttaaac    1726
ataatgccac aaggtcacta atttctagca ggtaaaatta taaggatata aattccaata   1786
ataaaccaaa tgtatttaga gtatttatta gtaaatgcaa ggtgatgtta gttatgatca   1846
gttatactct aaatatttaa tttgttttat aaaggtagtg aaaaaatgaa aatttgctat   1906
ttattaaaaa acattaaatt tcattccaaa tgagataagt gatattacta taacatctaa   1966
gcatcatctg atttgatatt ccctaaaaaa catttggaat atatgctatc tatagattca   2026
gtatctacta cccatattta ctttaccaaa tatatttctc ctcactgcat aaggactact   2086
cttctcatat tttcttcttt gatgaagata tttttcacca aagtttattt tgtgatgccc   2146
tcttggtttt gatactttaa aatctgtggc acccgttcta catgaattat caatatttgg   2206
taaattcaat ctgtatttgt tttgttaaag tcaaaaatct cattttccaa aaaaaaaaa    2266 aaaaaac                                                              2273
```

<210> SEQ ID NO 18
<211> LENGTH: 258
<212> TYPE: PRT
<213> ORGANISM: Human

<400> SEQUENCE: 18

```
Met Asn Arg Ala Phe Ser Arg Lys Lys Asp Lys Thr Trp Met His Thr
  1               5                  10                  15

Pro Glu Ala Leu Ser Lys His Phe Ile Pro Tyr Asn Ala Lys Phe Leu
                 20                  25                  30

Gly Ser Thr Glu Val Glu Gln Pro Lys Gly Thr Glu Val Val Arg Asp
             35                  40                  45

Ala Val Arg Lys Leu Lys Phe Ala Arg His Ile Lys Lys Ser Glu Gly
         50                  55                  60

Gln Lys Ile Pro Lys Val Glu Leu Gln Ile Ser Ile Tyr Gly Val Lys
 65                  70                  75                  80

Ile Leu Glu Pro Lys Thr Lys Ala Glu Glu Ile Thr Leu Thr Ile Gly
                 85                  90                  95

Gln Ala Phe Asp Leu Ala Tyr Arg Lys Phe Leu Glu Ser Gly Gly Lys
            100                 105                 110

Asp Val Glu Thr Arg Lys Gln Ile Ala Gly Leu Gln Lys Arg Ile Gln
        115                 120                 125

Asp Leu Glu Thr Glu Asn Met Glu Leu Lys Asn Lys Val Gln Asp Leu
    130                 135                 140

Glu Asn Gln Leu Arg Ile Thr Gln Val Ser Ala Pro Pro Ala Gly Ser
145                 150                 155                 160

Met Thr Pro Lys Ser Pro Ser Asp Ile Phe Asp Met Ile Pro Phe
                165                 170                 175

Ser Pro Ile Ser His Gln Ser Ser Met Pro Thr Arg Asn Gly Thr Gln
            180                 185                 190

Pro Pro Pro Val Pro Ser Arg Ser Thr Glu Ile Lys Arg Asp Leu Phe
        195                 200                 205

Gly Ala Glu Pro Phe Asp Pro Asn Cys Gly Ala Ala Asp Phe Pro
    210                 215                 220
```

```
Pro Asp Ile Gln Ser Lys Leu Asp Glu Met Gln Glu Gly Phe Lys Met
225                 230                 235                 240

Gly Leu Thr Leu Glu Gly Thr Val Phe Cys Leu Asp Pro Leu Asp Ser
                245                 250                 255

Arg Cys
```

<210> SEQ ID NO 19
<211> LENGTH: 18
<212> TYPE: DNA
<213> ORGANISM: Artificial Sequence
<220> FEATURE:
<223> OTHER INFORMATION: Primer

<400> SEQUENCE: 19
gaatgttctc atttattg                                            18

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20
ggattcaaac gatccgatg                                           19

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gaatctgtcc atcgcattgc                                          20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gaatttcttt gggtagaca                                           19

<210> SEQ ID NO 23
<211> LENGTH: 17
<212> TYPE: DNA
<213> ORGANISM: Artificial Sequence
<220> FEATURE:
<223> OTHER INFORMATION: Primer

<400> SEQUENCE: 23
gctctgaaga actgtga                                             17

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gacgaggtga agcgattgtg                                          20

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
gggatcaaac gaatcatc                                                  18

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
gtttaattac ccaagtttga g                                              21

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
ggttttaacc cagttactca ag                                             22

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
taatacgact cactataggg aga                                            23

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
attaaccctc actaaaggga                                                20

<210> SEQ ID NO 30
<211> LENGTH: 148
<212> TYPE: PRT
<213> ORGANISM: Caenorhabditis elegans
<220> FEATURE:
<221> NAME/KEY: VARIANT
<222> LOCATION: (1)...(107)
<223> OTHER INFORMATION: Xaa - any amino acid

<400> SEQUENCE: 30

His Pro Pro Asp Tyr Leu Ile Asn Gly His Val Glu Tyr Val Ala Arg
 1               5                  10                  15

Phe Leu Gly Cys Val Glu Thr Pro Lys Ala Asn Gly Ser Asp Val Ala
            20                  25                  30

```
Arg Glu Ala Ile His Ala Ile Arg Phe Gln Arg Asp Leu Lys Arg Ser
            35                  40                  45

Glu Gln Thr Arg Glu Thr Ala Lys Leu Gln Lys Val Glu Ile Arg Ile
 50                  55                  60

Ser Ile Asp Asn Val Ile Ile Ala Asp Ile Lys Thr Lys Ala Pro Met
 65                  70                  75                  80

Tyr Thr Phe Pro Leu Gly Arg Ile Ser Phe Cys Ala Asp Asp Lys Asp
                85                  90                  95

Asp Lys Arg Met Phe Ser Phe Ile Ala Arg Ala Glu Gly Ala Ser Gly
                100                 105                 110

Lys Pro Ser Cys Tyr Ala Phe Thr Ser Glu Lys Leu Ala Glu Asp Ile
            115                 120                 125

Thr Leu Thr Ile Gly Glu Ala Phe Asp Leu Ala Tyr Lys Arg Phe Leu
    130                 135                 140

Asp Lys Asn Arg
145

<210> SEQ ID NO 31
<211> LENGTH: 93
<212> TYPE: PRT
<213> ORGANISM: Caenorhabditis Briggsae

<400> SEQUENCE: 31

His Pro Pro Asp Phe Leu Ile Asn Gly His Val Glu Tyr Gly Ala Arg
 1               5                   10                  15

Phe Leu Gly Cys Val Glu Thr Ala Lys Glu Asn Gly Thr Ala Val Ala
                20                  25                  30

Arg Glu Ala Ile His Ala Ile Arg Phe Gln Arg Asp Leu Lys Arg Ser
            35                  40                  45

Glu Gln Thr Arg Glu Thr Ala Lys Leu Gln Lys Val Glu Ile Lys Ile
 50                  55                  60

Ser Ile Asp Tyr Val Arg Val Asp Asp Ala Lys Thr Lys Thr Met Met
 65                  70                  75                  80

Tyr Gln Phe Gln Leu Pro Arg Ile Ser Phe Cys Ala Asp
                85                  90

<210> SEQ ID NO 32
<211> LENGTH: 107
<212> TYPE: PRT
<213> ORGANISM: Human Est
<220> FEATURE:
<221> NAME/KEY: VARIANT
<222> LOCATION: (1)...(107)
<223> OTHER INFORMATION: Xaa - any amino acid
<220> FEATURE:
<221> NAME/KEY: VARIANT
<222> LOCATION: (1)...(107)
<223> OTHER INFORMATION: Xaa = Any Amino Acid

<400> SEQUENCE: 32

Phe Ala Arg His Ile Lys Lys Ser Glu Glu Gly Gln Lys Ile Pro Lys
 1               5                   10                  15

Val Glu Leu Gln Ile Ser Ile Tyr Gly Val Lys Ile Leu Glu Pro Lys
                20                  25                  30

Thr Lys Glu Val Gln Xaa Gln Leu Pro Asn Cys Gln Leu His Arg Ile
            35                  40                  45

Ser Phe Cys Ala Asp Asp Lys Thr Asp Lys Arg Ile Phe Thr Phe Ile
    50                  55                  60

Cys Lys Asp Ser Glu Ser Asn Lys His Leu Cys Tyr Val Phe Asp Ser
```

```
                65                  70                  75                  80
Glu Lys Cys Ala Glu Glu Ile Thr Leu Thr Ile Gly Gln Ala Phe Xaa
                    85                  90                  95

Leu Ala Tyr Arg Lys Phe Leu Glu Ser Gly Gly
            100                 105

<210> SEQ ID NO 33
<211> LENGTH: 171
<212> TYPE: PRT
<213> ORGANISM: Human SHC

<400> SEQUENCE: 33

His Pro Asn Asp Lys Val Met Gly Pro Gly Val Ser Tyr Leu Val Arg
 1               5                   10                  15

Tyr Met Gly Cys Val Glu Val Leu Gln Ser Met Arg Ala Leu Asp Phe
                20                  25                  30

Asn Thr Arg Thr Gln Val Thr Arg Glu Ala Ile Ser Leu Val Cys Glu
            35                  40                  45

Ala Val Pro Gly Ala Lys Gly Ala Thr Arg Arg Lys Pro Cys Ser
        50                  55                  60

Arg Pro Leu Ser Ser Ile Leu Gly Arg Ser Asn Leu Lys Phe Ala Gly
65                  70                  75                  80

Met Pro Ile Thr Leu Thr Val Ser Thr Ser Leu Asn Leu Met Ala
                85                  90                  95

Ala Asp Cys Lys Gln Ile Ile Ala Asn His His Met Gln Ser Ile Ser
            100                 105                 110

Phe Ala Ser Gly Gly Asp Pro Asp Thr Ala Glu Tyr Val Ala Tyr Val
        115                 120                 125

Ala Lys Asp Pro Val Asn Gln Arg Ala Cys His Ile Leu Glu Cys Pro
    130                 135                 140

Glu Gly Leu Ala Gln Asp Val Ile Ser Thr Ile Gly Gln Ala Phe Glu
145                 150                 155                 160

Leu Arg Phe Lys Gln Tyr Leu Arg Asn Pro Pro
                165                 170

<210> SEQ ID NO 34
<211> LENGTH: 165
<212> TYPE: PRT
<213> ORGANISM: Drosophila SHC

<400> SEQUENCE: 34

Tyr Pro Asp Asp Val Ile Met Gly Val Gly Val Ala Phe Asn Val Arg
 1               5                   10                  15

Tyr Thr Gly Cys Val Glu Val Lys Thr Ser Met Lys Ser Leu Asp Phe
                20                  25                  30

Glu Thr Arg Thr Gln Leu Ala Arg Glu Cys Ile Asn Arg Val Cys Glu
            35                  40                  45

Ala Ala Gly Leu Lys Ser Ala Gly Lys Arg Arg Leu Thr Asn Phe Ile
        50                  55                  60

Ser Asp Arg Pro Ser Met Gln His Ala Gly Thr Asn Ile Ile Ile Asn
65                  70                  75                  80

Val Ser Ser Arg Ala Leu Ser Leu Ser Asn Val Glu Thr Gly Glu Val
                85                  90                  95

Ile Ala Asn His Asn Met Pro Arg Ile Ser Phe Ala Ser Gly Gly Asp
            100                 105                 110

Asn Asp Thr Leu Asp Phe Leu Ala Tyr Ile Ala Lys Asn Glu Asp Glu
```

```
                    115                 120                   125
Trp Arg Ala Cys Tyr Val Leu Glu Cys Ala Gly Gly Gln Ser Glu Asp
            130                 135                 140

Leu Ile Val Thr Ile Gly Lys Ala Phe Ala Leu Arg Phe Asn Ala Leu
145                 150                 155                 160

Ser Arg Leu Asn Asp
                165

<210> SEQ ID NO 35
<211> LENGTH: 137
<212> TYPE: PRT
<213> ORGANISM: Drosophila Numb

<400> SEQUENCE: 35

Ala Asp Glu Glu Ala Val Arg Ser Ala Thr Cys Ser Phe Ser Val Lys
1               5                   10                  15

Tyr Leu Gly Cys Val Glu Val Phe Glu Ser Arg Gly Met Gln Val Cys
            20                  25                  30

Glu Glu Ala Leu Lys Val Leu Arg Gln Ser Arg Arg Pro Val Arg
        35                  40                  45

Gly Leu Leu His Val Ser Gly Asp Gly Leu Arg Val Val Asp Asp Glu
    50                  55                  60

Thr Lys Gly Leu Ile Val Asp Gln Thr Ile Glu Lys Val Ser Phe Cys
65                  70                  75                  80

Ala Pro Asp Arg Asn His Glu Arg Gly Phe Ser Tyr Ile Cys Arg Asp
                85                  90                  95

Gly Thr Thr Arg Arg Trp Met Cys His Gly Phe Leu Ala Cys Lys Asp
            100                 105                 110

Ser Gly Glu Arg Leu Ser His Ala Val Gly Cys Ala Phe Ala Val Cys
        115                 120                 125

Leu Glu Arg Lys Gln Arg Arg Asp Lys
    130                 135

<210> SEQ ID NO 36
<211> LENGTH: 141
<212> TYPE: PRT
<213> ORGANISM: P96

<400> SEQUENCE: 36

Tyr Leu Leu Ala Arg Phe Lys Gly Asp Gly Val Lys Tyr Lys Ala Lys
1               5                   10                  15

Leu Ile Gly Ile Asp Asp Val Pro Asp Ala Arg Gly Asp Lys Met Ser
            20                  25                  30

Gln Asp Ser Met Met Lys Leu Lys Gly Met Ala Ala Ala Gly Arg Ser
        35                  40                  45

Gln Gly Gln His Lys Gln Arg Ile Trp Val Asn Ile Ser Leu Ser Gly
    50                  55                  60

Ile Lys Ile Ile Asp Glu Lys Thr Gly Val Ile Glu His Glu His Pro
65                  70                  75                  80

Val Asn Lys Ile Ser Phe Ile Ala Arg Asp Val Thr Asp Asn Arg Ala
                85                  90                  95

Phe Gly Tyr Val Cys Gly Gly Glu Gly Gln His Gln Phe Phe Ala Ile
            100                 105                 110

Lys Thr Gly Gln Gln Ala Glu Pro Leu Val Val Asp Leu Lys Asp Leu
        115                 120                 125

Phe Gln Val Ile Tyr Asn Val Lys Lys Lys Glu Glu Asp
```

130          135          140

<210> SEQ ID NO 37
<211> LENGTH: 139
<212> TYPE: PRT
<213> ORGANISM: Drosophila Disabled

<400> SEQUENCE: 37

Asn Asp Pro Gly Arg Phe Phe Gly Asp Gly Val Gln Phe Lys Ala Lys
1               5                   10                  15

Leu Ile Gly Ile Leu Glu Val Gly Glu Ala Arg Gly Asp Arg Met Cys
            20                  25                  30

Gln Glu Ala Leu Gln Asp Leu Lys Met Ala Ile Arg Ala Ala Gly Glu
        35                  40                  45

His Lys Gln Arg Ile Thr Ile His Val Thr Ile Asp Gly Leu Arg Leu
    50                  55                  60

Arg Asp Glu Lys Thr Gly Asp Ser Leu Tyr His His Pro Val His Lys
65                  70                  75                  80

Ile Ser Phe Ile Ala Gln Asp Met Thr Asp Ser Arg Ala Phe Gly Tyr
                85                  90                  95

Ile Phe Gly Ser Pro Asp Ser Gly His Arg Phe Phe Gly Ile Lys Thr
            100                 105                 110

Asp Lys Ala Ala Ser Gln Val Val Leu Ala Met Arg Asp Leu Phe Gln
        115                 120                 125

Val Val Phe Glu Leu Lys Lys Lys Glu Ile Glu
    130                 135

<210> SEQ ID NO 38
<211> LENGTH: 139
<212> TYPE: PRT
<213> ORGANISM: Caenorhabditis elegans M110.5

<400> SEQUENCE: 38

Ser Asp Pro Phe Arg Phe Gln Asn Asn Gly Ile Ser Tyr Lys Gly Lys
1               5                   10                  15

Leu Ile Gly Glu Gln Asp Val Asp Lys Ala Arg Gly Asp Ala Met Cys
            20                  25                  30

Ala Glu Ala Met Arg Thr Ala Lys Ser Ile Ile Lys Ala Ala Gly Ala
        35                  40                  45

His Lys Thr Arg Ile Thr Leu Gln Ile Asn Ile Asp Gly Ile Lys Val
    50                  55                  60

Leu Asp Glu Lys Ser Gly Ala Val Leu His Asn Phe Pro Val Ser Arg
65                  70                  75                  80

Ile Ser Phe Ile Ala Arg Asp Ser Ser Asp Ala Arg Ala Phe Gly Leu
                85                  90                  95

Val Tyr Gly Glu Pro Gly Gly Lys Tyr Lys Phe Tyr Gly Ile Lys Thr
            100                 105                 110

Ala Gln Ala Ala Asp Gln Ala Val Leu Ala Ile Arg Asp Met Phe Gln
        115                 120                 125

Val Val Phe Glu Met Lys Lys Lys Gln Ile Glu
    130                 135

<210> SEQ ID NO 39
<211> LENGTH: 79
<212> TYPE: PRT
<213> ORGANISM: Drosophila EST

<400> SEQUENCE: 39

```
Lys Lys Leu Glu Ile Thr Ile Ser Ile Lys Gly Val Ala Ile Gln Glu
 1               5                  10                  15

Pro Arg Thr His Lys Ile Leu His Gln Phe Pro Leu Tyr Asn Ile Ser
             20                  25                  30

Tyr Cys Ala Asp Glu Lys Gly Val Lys Lys Phe Phe Ser Phe Ile Ala
         35                  40                  45

Glu Cys Phe Val Phe Ile Ser Asn Lys Leu Ala Ser Asp Ile Thr Leu
     50                  55                  60

Thr Ile Gly Gln Ala Phe Asp Leu Ala Tyr Arg Lys Tyr Met Asp
65                  70                  75
```

<210> SEQ ID NO 40
<211> LENGTH: 429
<212> TYPE: DNA
<213> ORGANISM: Human EST R65983
<220> FEATURE:
<221> NAME/KEY: misc_feature
<222> LOCATION: (1)...(429)
<223> OTHER INFORMATION: n = A,T,C or G

<400> SEQUENCE: 40

```
cttgaaacgg gnaaccgggc cnctgcaagc nggaactacc gtgcccaagt tatttatgan      60
ccccacctga tatacatggg agagaaactg atagaagaat tctgatggca actgtatgat     120
agaagctata taaagtcaag tgtccatttt ctttcaacta tatttgagca tacccaggat     180
ttaagtcgtg gaactgaaca tttatttggc tgatcctcat catgaaccgt gcttttagca     240
ggaagaaaga caaaacatgg atgcatacac ctgaagcttt atcaaaacat tcattccct      300
ataatgcaaa gtttcttggc agtacagaag tggaacagcc aaaaggaaca gaagttgtga     360
gagatgctgt aaggaaacta agtttgcaa gacatntcaa gaaatctgaa ggccaaaaaa      420
aaaaaaaag                                                            429
```

<210> SEQ ID NO 41
<211> LENGTH: 622
<212> TYPE: DNA
<213> ORGANISM: PCR Fragment

<400> SEQUENCE: 41

```
aagaattctg atggcaactg tatgatagaa gctattataa agtcaagtgt ccatttctt      60
tcaactatat ttgagcatac ccaggattta agtcgtggaa ctgaacattt atttggctga     120
tcctcatcat gaaccgtgct tttagcagga agaaagacaa acatggatg catacacctg      180
aagctttatc aaaacatttc attccctata atgcaaagtt tcttggcagt acagaagtgg     240
aacagccaaa aggaacagaa gttgtgagag atgctgtaag gaaactaaag tttgcaagac     300
atatcaagaa atctgaaggc cagaaaattc taaagtgga gttgcaaata tcaatttatg      360
gagtaaaaat tctagaaccc aaaacaaagg aagttcaaca caattgccag cttcatagaa     420
tatcttttg tgcagatgat aaaactgaca agaggatatt cactttcata tgcaaagatt      480
ctgagtcaaa taaacatttg tgctatgtat ttgacagcga aagtgtgct gaagagatca      540
ctttaacaat tggccaagca tttgacctgg catacaggaa atttctagaa tcaggaggaa     600
aagatgttga aacaagaaaa ca                                             622
```

<210> SEQ ID NO 42
<211> LENGTH: 1711
<212> TYPE: DNA
<213> ORGANISM: Artificial Sequence
<220> FEATURE:
<223> OTHER INFORMATION: Human Est hbc 3123

<400> SEQUENCE: 42

```
caattgccag cttcatagaa tatcttttg tgcagatgat aaaactgaca agaggatatt      60
cactttcata tgcaaagatt ctgagtcaaa taaacatttg tgctatgtat ttgacagcga    120
aaagtgtgct gaagagatca ctttaacaat tggccaagca tttgacctgg catacaggaa    180
atttctagaa tcaggaggaa aagatgttga acaagaaaa cagatcgcag ggttacaaaa     240
aagaatccaa gacttagaaa cagaaaatat ggaacttaaa aataaagtac aagatttgga    300
aaaccaactg agaataactc aagtatcagc acctccagca ggcagtatga cacctaagtc    360
gccctccact gacatctttg atatgattcc attttctcca atatcacacc agtcttcgat    420
gcctactcgc aatggcacac agccacctcc agtacctagt agatctactg agattaaacg    480
ggacctgttt ggagcagaac cttttgaccc atttaactgt ggagcagcag atttccctcc    540
agatattcaa tcaaaattag atgagatgca ggaggggttc aaaatgggac taactcttga    600
aggcacagta ttttgtctcg acccgttaga cagtaggtgc tgacatcaag aacaagaaat    660
cctgattcat gttaaatgtg tttgtataca catgtcattt attattatta ctttaagata    720
ggtattattc atgtgtcaat gttttgaat attttaatat tttgaaaatt ttctcagtta    780
aatttcctca ccttcactat tgatctgtaa tttttatttt aaaaacagct tactgtaaag    840
tagatcatac ttttatgttc ctttctgttt ctactgtaga tgaatttgta attgaaagac    900
atattataca aatacctgcc ttgtgtctga gttctattta gttagcatct tgaaatttgt    960
attcattttc cagatggcta gtttattaat gatttcccaa aagccatacc ttaaagataa   1020
cttttaat tctgaagaga catgccaatg tcaaactaaa catgttctgt tttaaacca      1080
acaaacatgt tactattcat tggacagata tcattttatg tataaatact gttcacatca   1140
ctgggaaaat gtaaacttta aacataatgc cacaaggtca ctaatttcta gcaggtaaaa   1200
ttataaggat ataaattcca ataataaacc aaatgtattt agagtattta ttagtaaatg   1260
caaggtgatg ttagttatga tcagttatac tctaaatatt taatttgttt tataaaggta   1320
gtgaaaaaat gaaaatttgc tatttattaa aaaacattaa atttcattcc aaatgagata   1380
agtgatatta ctataacatc taagcatcat ctgatttgat attccctaaa aaacatttgg   1440
aatatatgct atctatagat tcagtatcta ctacccatat ttactttacc aaatatattt   1500
ctcctcactg cataaggact actcttctca tattttcttc tttgatgaag atatttttca   1560
ccaaagttta ttttgtgatg ccctcttggt tttgatactt taaatctgt ggcacccgtt    1620
ctacatgaat tatcaatatt tggtaaattc aatctgtatt tgttttgtta aagtcaaaaa   1680
tctcattttc caaaaaaaaa aaaaaaaaa c                                   1711
```

<210> SEQ ID NO 43
<211> LENGTH: 478
<212> TYPE: DNA
<213> ORGANISM: Human Est r65882
<220> FEATURE:
<221> NAME/KEY: misc_feature
<222> LOCATION: (1)...(478)
<223> OTHER INFORMATION: n=A, T, C or G
<220> FEATURE:
<221> NAME/KEY: misc_feature
<222> LOCATION: (1)...(478)
<223> OTHER INFORMATION: n = A,T,C or G

<400> SEQUENCE: 43

-continued

```
gctaaattcg cttggccggg tccaccttct cgtggcctca ctcgccacac ggatcagaat    60
ccggagcagg cagttctctc tattctgagg ctcctgcggc tgccggctga cttccctgtg   120
tgcgggaggg aactctgggc aggctggttt tcttggaatg tgtttacgat gttgaatggg   180
acttgaacag gaagctggac gctgcagctg gaactagcgt gccaagttat ttatgattcc   240
atctgatata cataggagag aaactgatag aagaattctg atggcaactg tatgatagaa   300
gctatataaa gtcaagtgtc cattttcttt caactatatt tgagcatacc cagggtttaa   360
gtcgtggaac tgaacattta tttggctgat cctcatcatg gaaccgtgct tttagcagga   420
agaaagacaa aacatgggtg ctnacacctg aagnttatca aaacnttctt tccnattt    478
```

<210> SEQ ID NO 44
<211> LENGTH: 415
<212> TYPE: DNA
<213> ORGANISM: human est aa159394
<220> FEATURE:
<221> NAME/KEY: misc_feature
<222> LOCATION: (1)...(415)
<223> OTHER INFORMATION: n=A, T, C or G
<220> FEATURE:
<221> NAME/KEY: misc_feature
<222> LOCATION: (1)...(415)
<223> OTHER INFORMATION: n = A,T,C or G

<400> SEQUENCE: 44

```
ggtgatgagc ccttgggttc tcgctccgac tgctaaattc gcttggccgg gtccaccttc    60
tcgtggcctc actcgccaca cggatcagaa tccggagcag gcagttctct ctattctgag   120
gctcctgcgg cntgccngcg tgacttcccg tgtgtggngg agggaactct gggcaggctg   180
gttttcttgg aatgtgttta cgatgttgaa tgggacttga acaggaagct ggacgctgca   240
gctggaacta gcgtgccaag ttatttatga ttccatctgn tatacatagg agagaaactt   300
gatagaagaa ttctgatggc aactgtatga tagaagctat ataagtcaa gtgtccattt   360 tctttcaact atatttgagc atacccagga tttaagtcgt ggaactgaac attat       415
```